(12) United States Patent
Gardner et al.

(10) Patent No.: US 10,966,610 B2
(45) Date of Patent: Apr. 6, 2021

(54) ANGIOGENIC TREATMENT OF ISCHEMIC HEART DISEASE

(71) Applicant: CARDIOVASCULAR BIOTHERAPEUTICS, INC., Las Vegas, NV (US)

(72) Inventors: Vance Gardner, Irvine, CA (US); Kenneth Thomas, Chatham, NJ (US); John Jacobs, Berkeley, CA (US); Thomas Stegmann, Petersberg (DE); Mickael Flaa, Las Vegas, NV (US); Laurence R. Meyerson, Henderson, NV (US)

(73) Assignees: Venturis Therapeutics, Inc., Dallas, TX (US); Vance Gardner, Irvine, CA (US); John Jacobs, Berkley, CA (US); Thomas Stegmann, Petersburg (DE); Mickael Flaa, Las Vegas, NV (US); Kennth Thomas, Chatham, NJ (US)

( * ) Notice: Subject to any disclaimer, the term of this patent is extended or adjusted under 35 U.S.C. 154(b) by 0 days.

(21) Appl. No.: 15/641,649

(22) Filed: Jul. 5, 2017

(65) Prior Publication Data
US 2017/0296055 A1    Oct. 19, 2017

Related U.S. Application Data

(63) Continuation of application No. PCT/US2016/012241, filed on Jan. 5, 2016.
(Continued)

(51) Int. Cl.
*A61B 5/00* (2006.01)
*A61K 38/18* (2006.01)
(Continued)

(52) U.S. Cl.
CPC .......... *A61B 5/0013* (2013.01); *A61B 5/0024* (2013.01); *A61B 5/0044* (2013.01);
(Continued)

(58) Field of Classification Search
CPC ..................................................... A61K 38/18
See application file for complete search history.

(56) References Cited

U.S. PATENT DOCUMENTS

| | | | |
|---|---|---|---|
| 5,439,818 | A | 8/1995 | Fiddes et al. |
| 6,054,122 | A | 4/2000 | MacPhee et al. |
| (Continued) | | | |

FOREIGN PATENT DOCUMENTS

| | | |
|---|---|---|
| RU | 2247533 C1 | 3/2005 |
| RU | 2009122370 A | 12/2010 |
| (Continued) | | |

OTHER PUBLICATIONS

Palmen et al., Fibroblast Growth Factor-1 Improves Cardiac Functional Recovery and Enhances Cell Survival After Ischemia and Reperfusion, Sep. 2004, Journal of the American College of Cardiology, 44(5), 1113-1123. (Year: 2004).*
(Continued)

*Primary Examiner* — Rex R Holmes
*Assistant Examiner* — Jennifer L Ghand
(74) *Attorney, Agent, or Firm* — Edwin S. Flores; Daniel J. Chalker; Chalker Flores, LLP

(57) ABSTRACT

Devices, methods, systems and procedures for localized, targeted treatment of angiogenic-based therapy in at least one region of interest in one or more layers of cardiac tissue. Various methods can include diagnosing a patient with ischemic heart disease or "at-risk" of manifesting ischemic heart disease, placing the patient into a specific angiogenic-based treatment therapy group, collecting image data, confirming image data and other diagnostic test results, devel-
(Continued)

oping a preoperative plan to target region of interest, inserting the catheter into a heart chamber, monitoring the distal end of the catheter tip within the heart on a visual display, contacting at least one layer of cardiac tissue, creating one or more channels in the heart tissue and/or administering the angiogenic-based therapy.

15 Claims, 24 Drawing Sheets

Related U.S. Application Data

(60) Provisional application No. 62/100,246, filed on Jan. 6, 2015, provisional application No. 62/100,259, filed on Jan. 6, 2015, provisional application No. 62/116,757, filed on Feb. 16, 2015, provisional application No. 62/116,765, filed on Feb. 16, 2015, provisional application No. 62/159,913, filed on May 11, 2015.

(51) Int. Cl.
*A61P 9/10* (2006.01)
*G01N 21/31* (2006.01)
*G01N 21/359* (2014.01)
*A61K 47/02* (2006.01)
*A61B 8/12* (2006.01)
*A61B 8/08* (2006.01)
*A61B 8/06* (2006.01)
*A61K 9/00* (2006.01)
*G01N 21/00* (2006.01)

(52) U.S. Cl.
CPC .............. *A61B 5/742* (2013.01); *A61K 38/18* (2013.01); *A61K 38/1825* (2013.01); *A61P 9/10* (2018.01); *G01N 21/314* (2013.01); *G01N 21/359* (2013.01); *A61B 5/00* (2013.01); *A61B 5/6852* (2013.01); *A61B 8/06* (2013.01); *A61B 8/0883* (2013.01); *A61B 8/12* (2013.01); *A61K 9/0019* (2013.01); *A61K 9/0024* (2013.01); *A61K 47/02* (2013.01); *G01N 21/00* (2013.01)

(56) References Cited

U.S. PATENT DOCUMENTS

| | | | |
|---|---|---|---|
| 6,165,975 | A | 12/2000 | Adams et al. |
| 6,258,119 | B1* | 7/2001 | Hussein ................. A61F 2/06 606/108 |
| 6,414,027 | B1 | 7/2002 | Neal |
| 6,706,682 | B2 | 3/2004 | Shabsigh |
| 6,747,063 | B2 | 6/2004 | Adams et al. |
| 6,748,258 | B1 | 6/2004 | Mueller et al. |
| 6,852,323 | B2 | 2/2005 | Lue et al. |
| 8,575,111 | B2 | 11/2013 | Santos et al. |
| 9,498,516 | B2 | 11/2016 | Suh et al. |
| 9,968,292 | B2 | 5/2018 | Gardner et al. |
| 2002/0032153 | A1 | 3/2002 | Whitehouse |
| 2003/0105007 | A1 | 6/2003 | Beaulieu et al. |
| 2004/0098075 | A1* | 5/2004 | Lee ................. A61N 1/056 607/122 |
| 2004/0115769 | A1* | 6/2004 | Stegmann ............ C07K 14/501 435/69.1 |
| 2007/0283969 | A1 | 12/2007 | Yamasaki et al. |
| 2009/0012498 | A1* | 1/2009 | Sawa ................. A61K 48/005 604/522 |
| 2009/0076481 | A1* | 3/2009 | Stegmann .............. G01N 33/74 604/522 |
| 2013/0012813 | A1* | 1/2013 | Sakaguchi ............... A61B 6/12 600/431 |
| 2013/0184821 | A1 | 7/2013 | Hariri et al. |
| 2013/0230454 | A1 | 9/2013 | Gardner et al. |
| 2103/0230454 | | 9/2013 | Gardner et al. |
| 2014/0045751 | A1* | 2/2014 | Blaber .................. C07K 14/50 514/9.1 |
| 2014/0171908 | A1* | 6/2014 | Matheny ................. A61M 5/14 604/508 |
| 2014/0234419 | A1 | 8/2014 | McNulty et al. |
| 2017/0296625 | A1 | 10/2017 | Gardner et al. |

FOREIGN PATENT DOCUMENTS

| | | |
|---|---|---|
| WO | 199105320 A1 | 4/1991 |
| WO | 199116021 A1 | 10/1991 |
| WO | 0006190 A1 | 10/2000 |
| WO | 0113031 A2 | 2/2001 |
| WO | 0214487 A2 | 2/2002 |
| WO | 02064157 A2 | 8/2002 |
| WO | 2008037262 A1 | 4/2008 |
| WO | 2014099323 A1 | 6/2014 |

OTHER PUBLICATIONS

M. Simons et al: "Clinical Trials in Coronary Angiogenesis: Issues, Problems, Consensus :An Expert Panel Summary", Circulation, vol. 102, No. 11, Sep. 12, 2000 (Sep. 12, 2000), pp. e73-e86.
R. J. Laham et al: "Local Perivascular Delivery of Basic Fibroblast Growth Factor in Patients Undergoing Coronary Bypass Surgery : Results of a Phase I Randomized, Double-Blind, Placebo-Controlled Trial", CIRCULATION, vol. 100, No. 18, Nov. 2, 1999 (Nov. 2, 1999), pp. 1865-1871.
Extended European Search Report [EP 16735323.4] dated Jul. 31, 2018.
Baffour, R., et al., "Enhanced Angiogenesis and Growth of Collaterals by In Vivo Administration of Recombinant Basic Fibroblast Growth Factor in a Rabbit Model of Acute Lower Limb Ischemia: Dose-Response Effect of Basic Fibroblast Growth Factor," J Vascular Surg (1992), 16(2):181-191.
Extended European Search Report for EP 16735324.2 dated Aug. 24, 2018.
International Search Report and Written Opinion for PCT/US2016/012243 (ISA/RU) dated Apr. 21, 2016.
International Search Report and Written Opinion for PCT/US2016/017965 (ISA/RU) dated Aug. 11, 2016.
Pandit, A. S., et al., "Stimulation of Angiogenesis by FGF-1 Delivered Through a Modified Fibrin Scafford," Growth Factors (1998), 15(2):113-123 (Abstract Only).
Stein Marshall J. "New Advances in Erectile Technology", Therapeutic Advances in Urology (2014), 6(1):15-24.
International Search Report (PCT/US2016/012241) dated Jun. 2, 2016 (ISA/RU).

\* cited by examiner

Anterior View

Anterior View

Posterior View

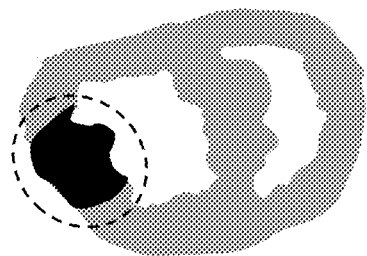
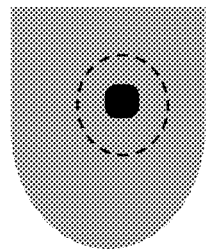
FIG. 7A  FIG. 7B
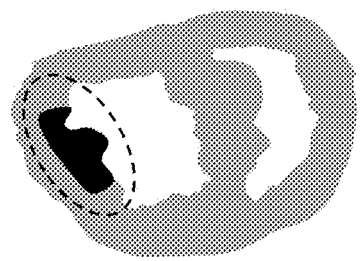
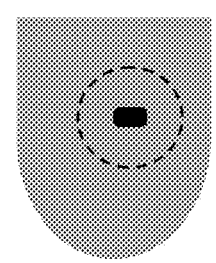
FIG. 8A  FIG. 8B
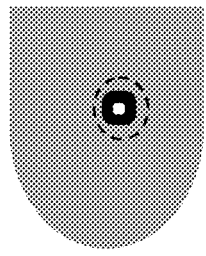
FIG. 9A  FIG. 9B

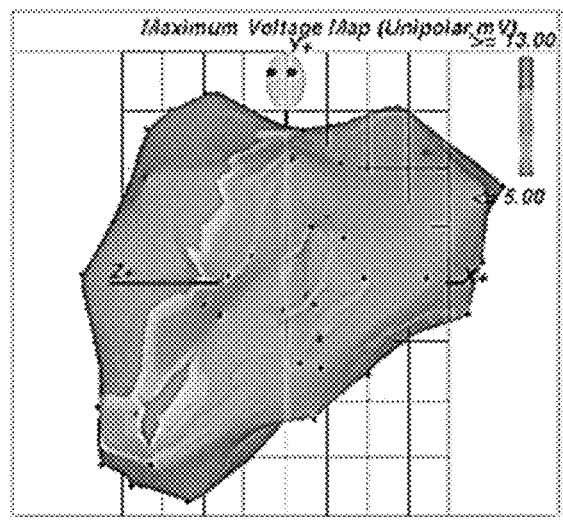
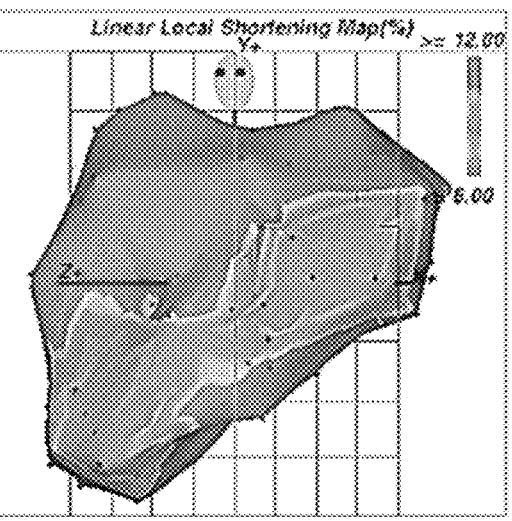
FIG. 12A
FIG. 12B
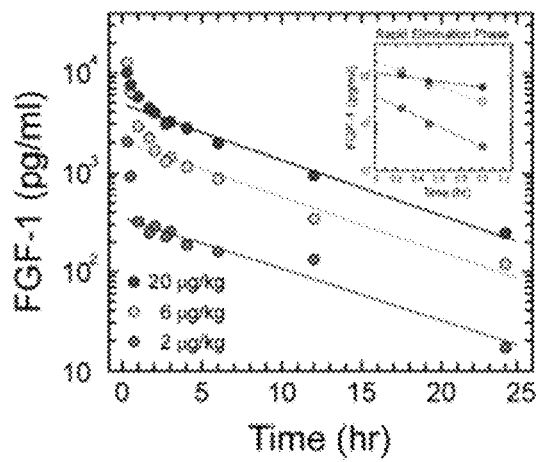
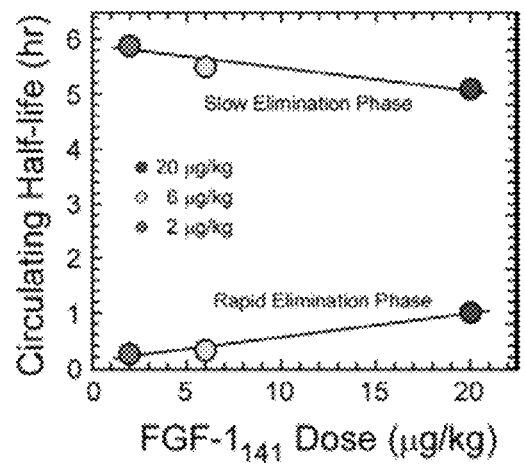
FIG. 13A
FIG. 13B
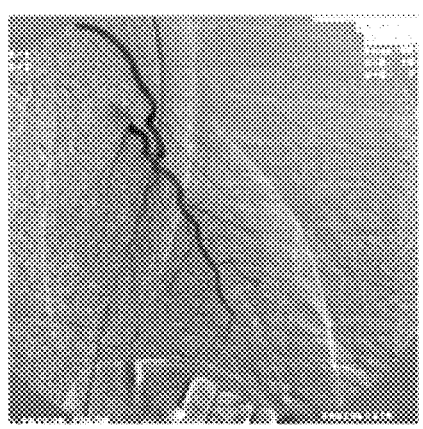
FIG. 14A
FIG. 14B Pre-Operative
Post-Operative (90 days)
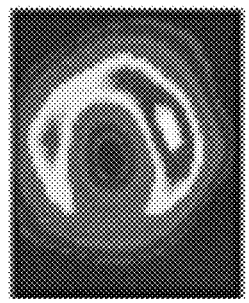
FIG. 15A
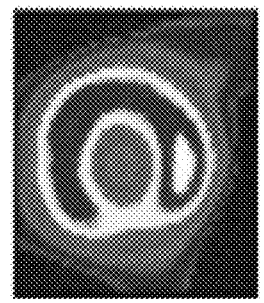
FIG. 15B
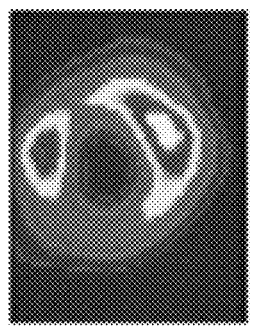
FIG. 16A
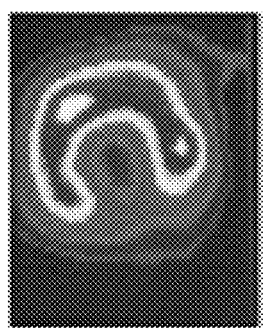
FIG. 16B
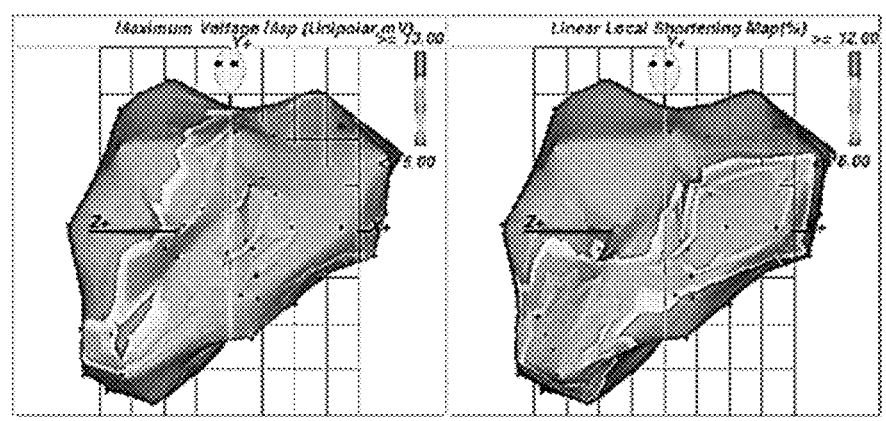
FIG. 17A
FIG. 17B

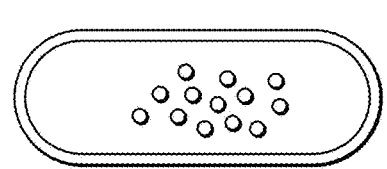
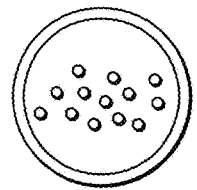
FIG. 30A      FIG. 30B
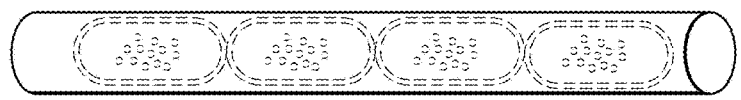
FIG. 31
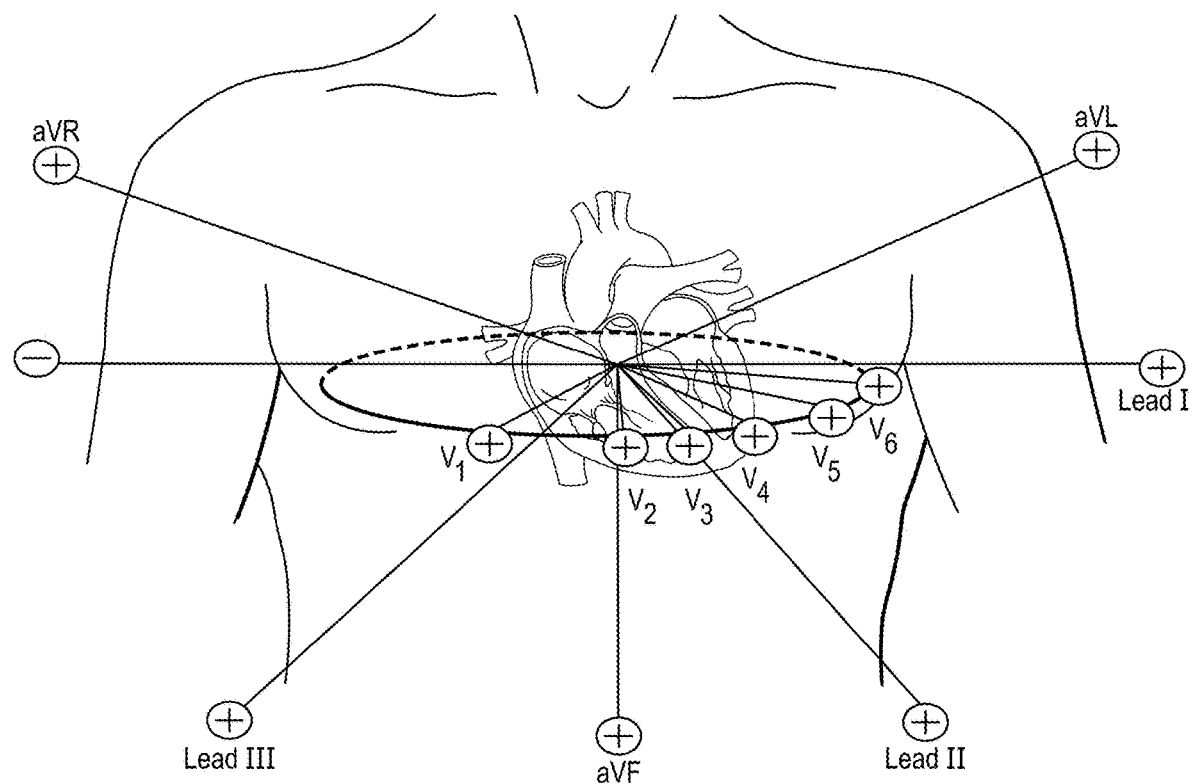
FIG. 32

ANGIOGENIC TREATMENT OF ISCHEMIC HEART DISEASE

CROSS REFERENCE TO RELATED APPLICATIONS

This application is a continuation application of PCT Patent Application Ser. No. PCT/US16/12241 entitled "ANGIOGENIC TREATMENT OF ISCHEMIC HEART DISEASE," filed Jan. 5, 2016, which in turn claims priority from the following U.S. Provisional Patent Applications: (1) 62/100,246 entitled "Angiogenic Treatment of Severe Coronary Artery Disease," filed Jan. 6, 2015; (2) 62/100,259 entitled "Angiogenic Treatment of Vascular Compromised Tissues," filed Jan. 6, 2015, (3) 62/116,757 entitled "Future of Vascular Medicine," filed Feb. 16, 2015, (4) 62/116,765 entitled "Small Vessel Disease Treatment," filed Feb. 16, 2015, and (5) 62/159,913 entitled "Angiogenic Treatment of Ischemic Heart Disease," filed May 11, 2015. The disclosures of each of these documents is incorporated by reference herein in their entireties.

TECHNICAL FIELD

The present invention relates to improved methods, systems, procedures and devices for angiogenic treatment of ischemic heart disease. More particularly, the improved methods and devices disclose image mapping techniques that allow a physician to administer localized angiogenic-based therapy with a delivery system to patients to revascularize, regulate, repair and/or regenerate damaged heart tissue and/or vessels, as well as stabilize atherosclerotic plaque.

BACKGROUND OF THE INVENTION

Ischemic heart disease (IHD) affects millions of Americans with substantial impact on survival and quality of life. IHD, also known as Coronary Artery Disease (CAD), is a condition that affects the supply of blood to the heart. CAD is most commonly due to atherosclerotic occlusion of the coronary arteries, and damage to walls of the microvasculature (Coronary Microvascular Disease—CMVD).

CAD causes the blood vessels to narrow or become blocked due to the deposition of atheromas (i.e., fat, cholesterol and other deposits) on the inside of the arterial walls and/or the damage to inner walls of the microvasculature. The narrowing, blockage, and/or damage to vessel walls results in hypoperfusion, and an inadequate supply of oxygen and nutrients to the heart tissue. Such supply of blood, oxygen and/or nutrients are essential for proper functioning of the heart, and the lack thereof may eventually result in a portion of the heart being suddenly deprived of its blood and oxygen resulting in some degree of ischemia (often causing angina pectoris). However, the consequences of ischemia can often collectively depend on the location and degree of obstruction, resulting in angina, heart failure, myocardial infarction, and/or even sudden death.

Current IHD treatments generally aim to reduce or minimize the progression and/or the complications of the disease after it has already manifested. Current IHD treatments have been shown to decrease cardiac workload by decreasing oxygen demand and improving coronary artery blood flow, and, over the long term, to minimize the atherosclerotic process. Many of the treatments may involve medical therapy (i.e., aspirin, lipid lowering drugs, beta blockers, nitrates, calcium channel blockers, ACE inhibitors, fibrinolytic drugs), percutaneous interventions (i.e., percutaneous coronary intervention—PCI, laser angioplasty, and/or arthrectomy) and/or surgical interventions (i.e., coronary artery bypass grafting—CABG, transmycardial revascularization, or laser revascularization).

Unfortunately, current IHD treatments are not entirely successful. Patients may be managed with one or more combinations of existing treatments, but many of these treatments may only address and/or manage the symptoms and are ineffective in delaying, prohibiting and/or correcting the underlying pathophysiology of CAD. Some of the treatments may be too invasive, and may not always effectively reduce secondary complications of angina, hypertension, mortality and/or restenosis. Furthermore, in some cases the managed treatments may introduce new disorders, such as development of new thrombi, cognitive dysfunction and/or behavioral changes potentially caused by microemboli originating in a bypass machine utilized during a CABG procedure or various percutaneous interventions.

BRIEF SUMMARY OF THE INVENTION

As a result, there is a need for improved methods and devices that are less invasive and that can potentially provide a cure for IHD, and/or alleviate secondary complications. Such a "cure" may include prevention of further progression of IHD, providing prophylactic care to prevent the overt manifestation of IHD in patients, and/or partially or fully reverse the effects of IHD. This may be accomplished in various embodiments described herein by utilizing various image mapping techniques that allow a physician to identify one or more areas requiring treatment and providing localized administration of an angiogenic-based therapy with a delivery system to (1) revascularize cardiac tissue; (2) repair and/or regenerate cardiac tissue; (3) regulate localized cell growth, migration, differentiation, and/or survival; (4) prophylactically treat cardiac tissue to prevent manifestation of IHD; and/or (5) stabilize atherosclerotic plaques.

In one exemplary embodiment, patients with IHD may be treated by various techniques described herein. Such patients with IHD may comprise a patient population with at least one atherosclerotic coronary vessel, small vessel disease (SVD) or microvascular disease (MVD), "at-risk" of developing IHD, symptomatic patients, non-symptomatic patients and/or any combination thereof.

In another exemplary embodiment, patients with IHD may be treated with an angiogenic-based therapy. The angiogenic-based therapy may comprise a therapeutically effective concentration of a growth factor, stimulating protein, and/or transcription factor that stimulates angiogenesis, such as described in U.S. Pat. No. 8,983,570 (the '570 patent), which is herein incorporated by reference in its entirety. Some exemplary growth factors that could be utilized with the various embodiments described herein include, but are not limited to, fibroblast growth factor 1 (FGF-1) through fibroblast growth factor 22 (FGF-22), HGF, VEGF and/or IGF.

In another exemplary embodiment, an angiogenic-based therapy may provide localized revascularization treatments to the biological heart or to a donor heart of IHD patients. This may be accomplished by administering the angiogenic-based therapy to a targeted region(s) of interest in an IHD patient's heart, which may include administration to the donor heart and/or biological heart prior to, during and/or after the implantation procedures. The angiogenic-based therapy may stimulate the proliferation and differentiation of one, two or more or all cell types necessary for the formation of new microvasculature. This may lead to potentially (1) bypassing and/or circumventing any occluded or partially occluded site of stenosis in the coronary vessels or epicardial vessels to reach a targeted region of interest where a new collateral network of microvasculature (i.e., resistance vessels) will be created to allow vasodilation and improve coronary perfusion; and (2) improve microvascular incompetence by introducing a new collateral network of microvasculature (i.e., resistance vessels) to decrease resistance to coronary blood flow and improve coronary perfusion.

In another exemplary embodiment, the angiogenic-based therapy may provide localized repair and/or regeneration treatments to the heart of IHD patients. This may be accomplished by administering the angiogenic-based therapy to a targeted region of interest in an IHD patient's heart. The targeted region of interest may include at least one layer of damaged or injured cardiac tissue, where the damage or injury may be manually inflicted by excision of tissue or inflicted by myocardial infarct (MI). The angiogenic-based therapy may promote angiogenesis, as well as stimulate proliferation of many cell types involved in wound healing, including endothelial cells, fibroblasts, and/or keratinocytes. This may lead to activation of the angiogenic-based therapy's mitogenic and chemotactic characteristics to induce the wound healing response, resulting in the regeneration and/or repairing of the damaged cardiac tissue with new cardiac tissue that replaces the damaged tissue and/or encapsulation of the damaged tissue with new cardiac tissue, thus desirably restoring some or all of the original contractile behavior of the localized cardiac tissue and reducing and/or eliminating potential ventricular dysfunction or remodeling.

In another exemplary embodiment, the angiogenic-based therapy may provide for localized regulation treatments to the heart of IHD patients. This may be accomplished by administering the angiogenic-based therapy to a targeted region of interest in an IHD patient's heart. The targeted region of interest may include atherosclerotic plaque, non-infarcted cardiac tissue, infarcted cardiac tissue, and/or vessels that may be proximal or adjacent to infarcted tissue. The angiogenic-based therapy may play a role in inhibiting and/or altering the reparative process that is quickly initiated to rebuild an infarcted myocardium with granulation or fibrous tissue formation that eventually forms into scar tissue to maintain structural integrity of the ventricle. The angiogenic-based therapy may antagonize the negative regulatory effects of transforming growth factor β (TGF-β1) or matrix metalloproteinases (MMPs) when high concentrations are present after an MI to induce fibrous tissue formation among other actions. Inhibition of the regulatory effects of TGF-β1 may reduce or eliminate some or all activity implicated in granulation or fibrous tissue formation, including differentiating fibroblasts (myoFb, interstitial, and/or adventitial fibroblasts), renin, macrophage activity, Angiotensin-converting enzyme (ACE) binding, and/or Angiotensin I and II receptors, and/or any combination thereof. Such angiogenic-based therapy may (1) develop or restore original contractile behavior of the localized cardiac tissue by allowing the repairing and/or regenerating of cardiac tissue as described herein, rather than formation of granulation or fibrous tissue; and/or (2) reduce or eliminate cardiac tissue (i.e., myocardial) remodeling to non-infarcted cardiac tissue and/or vessels sites adjacent to infarcted tissue sites. Such therapy can reduce and/or eliminate potential ventricular dysfunction.

In another exemplary embodiment, the angiogenic-based therapy may provide for localized treatments to regulate the regression of atherosclerotic plaque and/or treat endothelial dysfunction in the heart of IHD patients. This may be accomplished by administering the angiogenic-based therapy to a targeted region of interest in an IHD patient's heart. The targeted region of interest may include at least one coronary artery or coronary microvasculature (1) with and/or without the presence an atherosclerotic plaque, and/or (2) with or without the presence of vascular endothelial dysfunction. The angiogenic-based therapy may play a role in facilitating vascular endothelial repair through its mitogenic and/or chemotactic properties. The properties may include: (1) hemostasis and inflammation; (2) tissue formation and re-epithelialization; and/or (3) remodeling of the targeted region of interest. The properties may facilitate the actions of macrophage, fibroblast, and blood vessel migration into the damaged region of interest, with proliferation and migration of nearby epithelium to build a new vascular epithelial layer. The new vascular epithelial layer may now properly perform its vascular function, which includes regulation of vascular tone, formation of nitrous oxide (NO), maintenance of the composition of subendothelial matrix, proliferation of smooth muscle cells (SMCs), coagulation, fibrinolysis, permeability of lipoproteins and plasma proteins, and adhesion and migration of blood cells.

In another exemplary embodiment, the angiogenic-based therapy may provide for localized prophylactic treatments to the heart of patients to prevent the overt manifestation of IHD (hereinafter known as "at-risk" patients). This may be accomplished by evaluating endothelial function in the region of interest, including the use of non-invasive and/or minimally invasive methods of imaging cardiac or other tissues in the patient. If endothelial dysfunction is identified, then the physician may create a treatment plan identifying desired areas of treatment and then administer the angiogenic-based therapy to one or more targeted region(s) of interest in an IHD patient's heart. Physicians may select and/or predict patients to be treated by evaluating various major and/or minor risk factors that allow physicians to predict multivariate IHD risk in patients without overt IHD. Such major factors could include at least one of family history, age, genetic influences, tobacco use, overweight/obesity, unhealthy diet, physical inactivity, diabetes, hypertension, hypercholesteremia, metabolic syndrome, blood chemistry (i.e., C-reactive protein, triglycerides), gender, ventricular hypertrophy, and/or any combination thereof. The angiogenic-based therapy may also and/or alternatively play a role in preventing an overt manifestation of IHD in certain groups of patients, such as by adequately perfusing the localized region(s) of interest.

In another exemplary embodiment, the angiogenic-based therapy may provide for localized treatments to stabilize the progression of atherosclerotic plaques. This may be accomplished by characterizing the atherosclerotic plaque in a region of interest to determine its atherosclerotic classification. Once the atherosclerotic classification is identified, a physician can administer an angiogenic-based therapy to a targeted region of interest in an IHD patient's heart. The targeted region of interest may include at least one coronary artery or coronary microvasculature with the presence of an atherosclerotic plaque or an area adjacent to the coronary artery or coronary microvasculature with plaque. The angiogenic-based therapy may play a role in 1) hemostasis and inflammation; and/or (2) remodeling of the atherosclerotic plaque to prevent or delay further progression of the plaque. In various embodiments, the angiogenic treatment may induce the body to create a biologic "bypass" vessel that routes blood and/or other fluids around the plaque.

In another exemplary embodiment, the angiogenic-based therapy may provide for localized treatments to reduce and/or eliminate hypertension. Hypertension is a major public health problem because it affects approximately one in three adults in the U.S. Hypertension is typically determined by measuring the amount of blood the heart pumps and the amount of resistance to blood flow in the arteries. The amount of resistance may be due to the stiffness or lack of elasticity in the arterioles (microvascular incompetence), as well as various constrictions and/or blockages resident therein. Increased resistance tends to lead to decreased blood flow and oxygen to tissues. The autoregulation response is activated to request increased blood perfusion and oxygen to tissues (increased demand), but the body is typically unable to meet these demands. As a result, several complications of high blood pressure can occur, including ischemic heart disease, atherosclerotic disease, cardiac remodeling, eye damage and/or stroke. An angiogenic-based therapy such as described herein may stimulate the proliferation and differentiation of all cell types necessary for the formation of new microvasculature. This may lead to potentially improving microvascular incompetence by introducing a new collateral network of microvasculature (i.e., resistance vessels) to decrease resistance to coronary blood flow and improve coronary perfusion to surrounding tissues.

In another embodiment, patients with IHD may be treated with a delivery device system that administers the angiogenic-based therapy as described herein. The delivery device system may comprise at least one catheter, optionally including a steerable catheter tip, an injection component, an image mapping component, a deployment component, an implant, and/or any combination thereof. Furthermore, the delivery device system may include a standardized sized catheter that accommodates the physician's selected techniques as described herein and/or it may be a modular catheter that can be modified for size and function. Also, the delivery device system may generate a continuous release, intermittent release, manual release, and/or automatic release of the angiogenic-based therapy as described herein.

In another exemplary embodiment, patients with IHD may be treated with at least one of various invasive, minimally invasive and/or percutaneous techniques. Such invasive techniques may include full conventional heart surgery with a heart-lung bypass and/or thoracotomy. Alternatively and/or in addition, minimally invasive techniques may include a mini-thoracotomy, MIDCABG, robotically assisted techniques, and/or any surgery intending to minimize incision length. Alternatively, percutaneous techniques may include transfemoral (retrograde) percutaneous approach, carotid approach, right internal jugular vein approach, antegrade approach (via percutaneous transeptal or through left atrium via minithoracotomy), transapical approach, subclavian artery approach, auxillary artery approach and/or ascending aorta approach, or combinations thereof. At least one of the various invasive, minimally invasive, and/or percutaneous techniques may be used, as well as any combination thereof.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention:

FIGS. 7A-7B depicts various views of one embodiment of localized, targeted angiogenic-based therapy treatment;

FIGS. 8A-8B depicts various views of an alternate embodiment of localized, targeted angiogenic-based therapy treatment;

FIGS. 9A-9B depicts various views of an alternate embodiment of localized, targeted angiogenic-based therapy treatment;

FIGS. 12A and 12B depict various embodiments of left ventricular electromechanical maps;

FIGS. 13A and 13B illustrate a graph that plots FGF-1 dose concentration over time;

FIGS. 14A and 14B depict angiographic images with digital gray-value analysis;

FIGS. 15A and 15B depict one embodiment of SPECT imaging of the heart during preoperative and post-operative rest testing;

FIGS. 16A and 16B depict one embodiment of SPECT imaging of the heart during preoperative and post-operative stress testing;

FIGS. 17A and 17B depict one embodiment of Left-Ventricular Electromechanical voltage potential and contractility image maps of the heart;

FIGS. 30A and 30B depict a side and front view of one embodiment of a gel microcapsule with fluorescent, radiopaque and/or paramagnetic microspheres or nanospheres;

FIG. 31 illustrates a side view of one embodiment of a plurality of gel microcapsules loaded into a delivery catheter injection mechanism;

FIG. 32 illustrates an anterior view of one embodiment of the placement of 12-lead EKG wires;

DETAILED DESCRIPTION OF THE INVENTION

Figure 1:
FIG. 1 depicts one embodiment of a patient's heart with Ischemic Heart Disease and atherosclerotic lesions.

It is estimated that more than 16 million Americans have coronary artery disease (CAD) and 8 million have had a myocardial infarction (MI). CAD may affect the epicardial vessels (i.e., coronary arteries) and the coronary microvasculature. However, if the coronary arteries are affected, it is commonly due to atherosclerotic occlusion of the coronary arteries. Atherosclerosis is a process that can involve many of the body's blood vessels with a variety of presentations.

Atherosclerosis is the main cause of coronary artery disease. The atherosclerotic process begins as disruption of endothelial function due to the accumulation of lipoprotein droplets in the intima of the coronary vessels. Water insoluble lipids are carried in the bloodstream attached to water soluble apolipoproteins (lipoproteins). High concentrations of low density lipoprotein (LDL) can permeate an already disrupted or dysfunctional endothelium where it undergoes oxidation and, in diabetics, glycation. Modified LDL attracts leukocytes into the intima and can be scavenged by macrophages leading to the formation of foam cells. These cells replicate giving rise to one of the earliest pathological lesions; the fatty streak, which is the earliest visualized lesion of atherosclerosis. Smooth muscle cells are then recruited and migrate to the site of the foamy cells. Smooth muscle cells proliferate and manufacture extracellular matrix. A large volume of the plaque is occupied by extracellular matrix (collagen and proteoglycan) secreted by the smooth muscle cells. The fatty streak is now transformed into a fibrous plaque. At this point, the lesion typically begins to encroach on the lumen of the vessel. Structurally impaired microvasculature can form in these plaques, and these plaques can subsequently calcify. Inflammation plays an important role in promoting smooth muscle cell migration and proliferation. The final lesion, the advanced complicated lesion, consists of a fibrous cap overlying a lipid rich core which also contains necrotic material—this core is highly thrombogenic.

Once an atherosclerotic lesion encroaches within the lumen of the vessel, the encroachment may lead to an interruption of coronary blood flow that affects the oxygen supply the heart needs. The heart is an aerobic organ that is dependent on its oxygen supply from coronary perfusion. Therefore, if there is an occlusion in the coronary vessel, coronary blood flow is compromised and the oxygen supply is reduced. The myocardium reacts by increasing myocardial oxygen demand, but the occlusion will prevent the coronary vessel from meeting the demand of the myocardium. As a result, the imbalance between oxygen supply and demand results in ischemia.

Unfortunately, an imbalance between supply and demand may alternatively and/or also result from disruption of the autoregulation response of the heart, and the disruption may not necessarily result from the occlusion itself. Coronary arteries suffering from atherosclerosis typically lose the ability to release vasodilating substances that allow an increase in coronary perfusion in the face of increased demand, as well as they paradoxically constrict.

Figure 2:
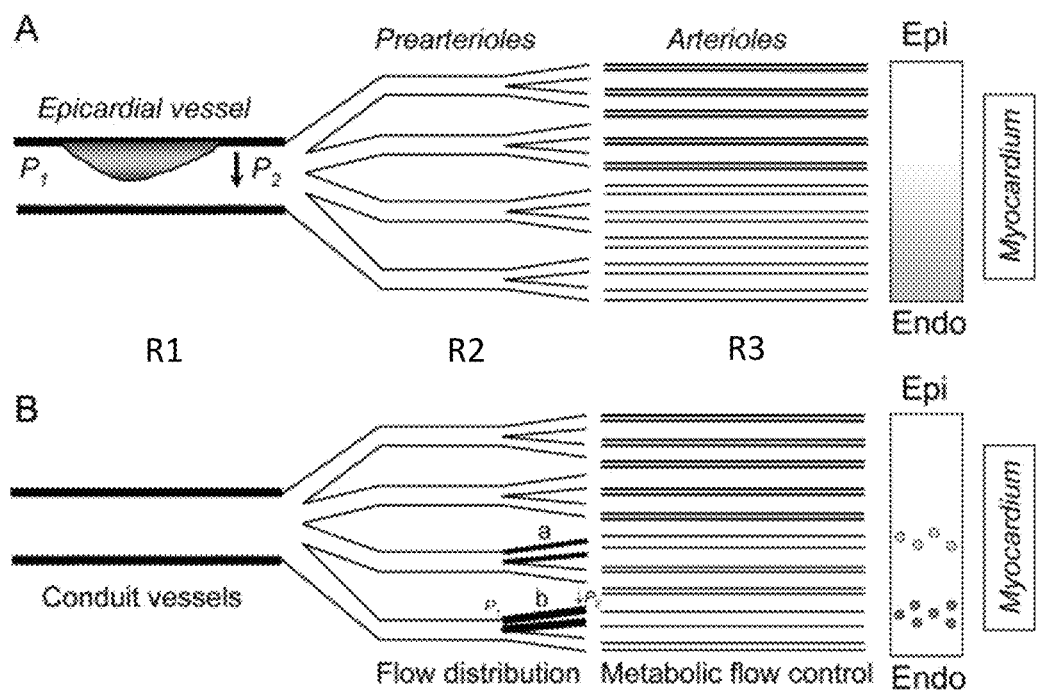
FIG. 2 depicts one embodiment of a patient's macro and microvasculature in the heart.

Coronary vessels can be divided into coronary vessels (R1), pre capillary (R2) and microvascular vessels (R3) (see FIG. 2). The epicardial vessels (or coronary vessels), the site most commonly affected by atherosclerosis, offer negligible resistance to coronary flow. Resistance to flow generally occurs in the pre-capillary (R2), and microvascular (R3) vessels, which can be termed "resistance vessels." The increased coronary blood flow in response to increase myocardial oxygen demand ($MVO_2$) is achieved by dilatation of these resistance vessels. Coronary blood flow is direction dependent on perfusion pressure and inversely proportional to the resistance of the coronary vessel. Coronary perfusion occurs in diastole, hence diastolic pressure is considered more relevant than systolic pressure in determining coronary perfusion.

Coronary vascular resistance can be reduced to ⅕th of baseline resistance leading to a five-fold increase in the volume of perfusion in response to an increase in need. Coronary reserve is the term used to reflect the amount of increase in coronary perfusion to accommodate increased demand. Autoregulation, mediated by changes in the vascular tone of the resistance vessels, allows distal coronary perfusion to remain unaltered in the face of changes in proximal perfusion pressures. Occlusions disrupts autoregulation and may lead to ischemia. The coronary reserve is limited by the failure to dilate and reduce vascular resistance. Vasodilating substances, such as acetylcholine, through the release of NO, results in vasodilation of the coronary vessels and the microvasculature to compensate for supply and demand. However, if the endothelium overlying the vascular smooth vessel was diseased (e.g. by atherosclerosis), the smooth muscle will paradoxically vasoconstrict. This paradoxical vasoconstriction is associated with endothelial dysfunction. Such disruption of the autoregulation response (i.e., ischemia) can clinically present itself into multiple manifested complications.

The duration and severity of ischemia will generally determine the fate of the compromised myocardium. Diastolic and systolic dysfunction are one of the first complications resulting from ischemia. This is followed by elevation of filling pressures, impaired ejection fraction, impaired contractility, impaired myocardial function, detectable electrocardiographic changes and then, chest pain or chest discomfort (i.e., angina pectoris), which may be associated with shortness of breath. Myocardial necrosis (infarction) is the final outcome of prolonged cessation of blood flow. The extent of myocardial necrosis depends upon the size of the territory supplied by the compromised vessel and the duration of antecedent ischemia to that territory. Hence, patients experiencing the aforementioned complications over a longer-term period may undergo cardiac remodeling to compensate for the localized myocardial changes, and subsequently death.

Alternatively, CAD may be caused by coronary microvasculature, instead of the typical discernable atherosclerotic occlusions observed in the coronary arteries. CAD originating from coronary microvasculature can be commonly referred as cardiac microvascular dysfunction (CMVD), small vessel disease (SVD) or non-obstructive CAD. As a result, a patient diagnosed with CMVD may exhibit some particularities in the coronary microvasculature (arterioles R2 and capillaries R3) that is sometimes difficult to detect.

Figure 3A:
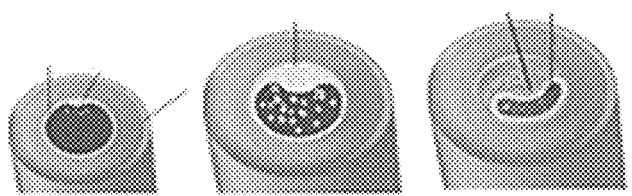
FIGS. 3A and 3B depicts one embodiment of cardiac vessels with atherosclerotic lesions, intimal thickening, and/or spasms.
Figure 3B:
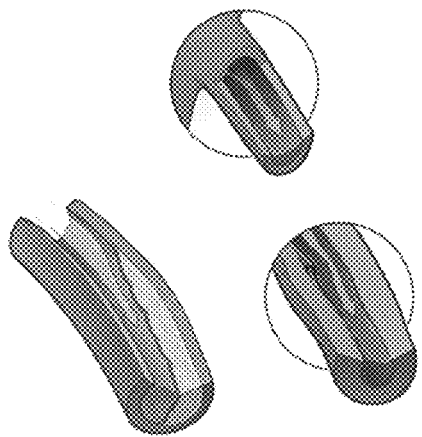
Figure 4A:
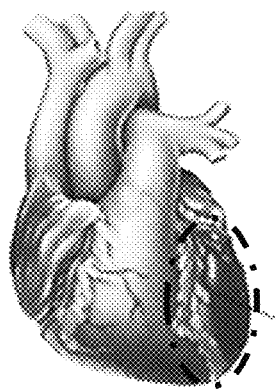
FIGS. 4A-4E illustrates various embodiments of common infarcted areas of the heart.
Figure 4B:
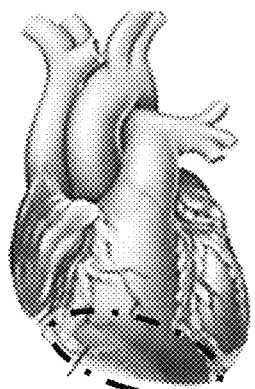
Figure 4C:
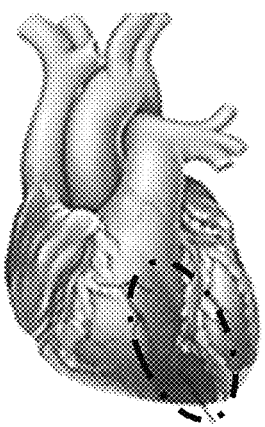
Figure 4D:
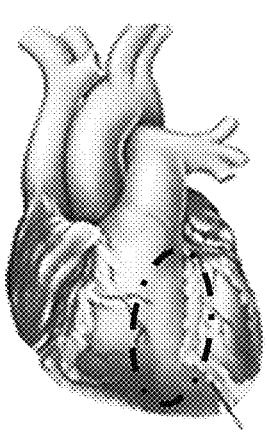
Figure 4E:
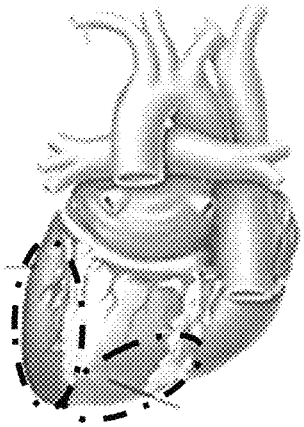

These microvascular particularities may be observed as various types of damage within the heart. The damage may be derived from endothelial dysfunction, spasms (or abnormal contraction) and/or diffuse intimal thickening (see e.g., FIGS. 3A and 3B) that impairs the myocardial blood flow by increasing blood flow resistance. However, damage to the CMV's may be sufficient enough to produce visible ECG changes, but it may not result in detectable: (1) contractile abnormalities because of the normal function of the surrounding myocardial tissue, (2) ischemic metabolites because of the sparse distribution of myocardial ischemic foci, (3) atherosclerotic plaque (absence of obstructive CAD or partial obstructive CAD), and/or (4) clinical presentation of symptoms (i.e., some patients with donor heart transplants may not experience symptoms due to denervation). Detection of common signs of myocardial ischemia is typically only possible when severe CMVD is uniformly present in sufficiently large myocardial regions.

As a result, CMVD may be difficult to detect since the common warning signs are not visually present when standard diagnostic methods are used. CMVD continues to be another significant cause that affects coronary blood flow due to the volume of microvascular networks within the hearts. As shown in FIG. 2, the blood flows to the heart muscle first through the large coronary arteries, then the blood flows through branches of thousands of smaller vessels, referred to as the microvasculature (i.e., arterioles and capillaries). The transition from artery to arteriole is a gradual one, marked by a progressive thinning of the vessel wall and a decrease in the size of the passageway. The job of the larger arteries is primarily the distribution of blood, and these vessels range from 1.0-4.0 millimeters in size. The job of the arterioles is primarily both blood distribution and resistance (pressure and flow regulation), and these vessels range from 0.1 to 0.5 millimeters in size. Unfortunately, where any particularities observed in a plurality of small sized vessels (i.e., increased resistance) does significantly impact the flow of oxygen-rich blood to the myocardium, this deprivation of oxygen (myocardial ischemia) may cause a variety of complications. Such complications, if experienced long-term, may induce cardiac remodeling, acute heart attacks, severe chest pain (i.e., angina and/or cardiac syndrome X, etc.), shortness of breath, fatigue, sleep problems, excessive sweating and even sudden death.

Therefore, there is a need to provide an improved intervention that is aimed at treating the pathophysiology of IHD, preventing or minimizing the impact remodeling and any adverse secondary complications may have on the heart. Such improved interventions may include (1) revascularizing cardiac tissue by creating a new network of coronary microvasculature; (2) repair and/or regeneration of cardiac tissue after ischemic injury; (3) regulation of localized cell growth within the cardiac tissue, migration, differentiation, and/or survival to inhibit scar formation; (4) prophylactically treating cardiac tissue to prevent and/or reduce manifestation of IHD; and/or (5) stabilize atherosclerotic plaques.

The improved intervention may comprise diagnosing the patient with IHD or "at-risk" of manifesting IHD; imaging a region of interest within the coronary vessels and/or the coronary microvasculature; conducting quantitative and qualitative analysis of the atherosclerotic plaque, coronary vessels and/or coronary microvasculature; using the imaging, quantitative and qualitative analysis results to determine the placement within a treatment group; using the imaging, quantitative and qualitative analysis results to create a preoperative plan; administer the angiogenic-based therapy to the localized region(s) of interest that is/are based on the treatment group and preoperative plan; follow-up with patient to determine the efficacy of the angiogenic-based therapy; optionally adjust the treatment group, the angiogenic-based therapy treatment regimen and/or create a new preoperative plan.

Patient Diagnosis—Preoperatively

In order for patients to receive optimal results from treatment with an angiogenic-based therapy, the patients will often either have clinical evidence of (or be diagnosed with) IHD or have a risk of developing IHD. Physicians can diagnose and confirm IHD patients by having the patient undergo a series of standard diagnostic and imaging tests, including those tests described in Table 1. Table 1 describes a series of standard diagnostic and imaging tests as they are well known in the art.

TABLE 1

Standard Diagnostic and Imaging Tests

| Test | Function |
| --- | --- |
| Physical Exam | A stethoscope may be used to check arteries for an abnormal whooshing sound called a bruit, which may indicate poor blood flow due to plaque buildup. The physician may also check to see if any pulses (for example, in the leg or foot) are weak or absent, which can be a sign of a blocked artery. |
| Blood Tests | Measures levels of biomarkers, electrolytes, blood cells, clotting factors, hormones, certain fats, cholesterol, sugar, enzymes and proteins in the blood. Abnormal levels may put the patient at risk for atherosclerosis, detect injury or an infarct. |
| ECD or EKG (electrocardiogram) | Measures the electrical activity, rate, and regularity of the heartbeat. |

TABLE 1-continued

Standard Diagnostic and Imaging Tests

| Test | Function |
| --- | --- |
| Echocardiogram | Uses 2D or 3D ultrasound to create a picture of the heart. |
| Exercise stress test | Measures the heart rate while the patient walks on a treadmill. This helps to determine how well the heart is working when it has to pump more blood. |
| Chest X-ray | Creates a 2D picture of the heart, lungs, and other organs in the chest. |
| Cardiac catheterization (angiogram) | Checks the inside of the arteries for blockage by threading a thin, flexible tube through an artery in the groin, arm, or neck to reach the coronary artery. Can measure blood pressure and flow in the heart's chambers, collect blood samples from the heart, or inject dye into the coronary arteries. |
| Coronary angiogram | Monitors blockage and flow of blood through the heart. Uses X-rays to detect dye injected via cardiac catheterization. |
| CT Angiography | Creates detailed 3D pictures of the heart by injecting a contrast dye through a vein in the arm and x-rays are taken while the person is lying on a specialised x-ray table. The contrast dye briefly fills the arteries of the heart and the heart chambers, enabling them to be seen on the x-ray pictures. The 3D pictures can indicate any narrowings, fat deposits and calcium in arteries, as well as measure heart muscle function. |
| Nuclear Isotope Imaging | Nuclear isotope imaging involves the injection of a radioactive compound called a tracer into the bloodstream. Computer generated pictures of the tracer are then taken as it moves through the heart. From these images it is possible to assess how the heart is functioning and detect any narrowed or blocked blood vessels. Nuclear isotope imaging techniques include: multigated radionuclide angiography (MUGA), positron emission tomography (PET) and single photon emission computed tomography (SPECT). |
| Magnetic Resonance Imaging | Creates a detailed 3D images of the heart by having the patient lay inside a long tube-like machine that produces a magnetic field. The magnetic field aligns atomic particles in some of your cells. When radio waves are broadcast toward these aligned particles, they produce signals that vary according to the type of tissue. |
| Endothelial Function/Dysfunction Test | Creates detailed images of the blood flow through the coronary arteries and measures it. A wire will be threaded through a catheter inserted in one of the coronary arteries to have a medication injected into the artery that causes the small vessels in the heart to open and let blood rush through, for measuring the blood flow. |

In another embodiment, a physician may select a patient for angiogenic-based therapy when the patient has confirmed clinical evidence of IHD. Such patients with confirmed clinical evidence of IHD, or often known as coronary artery disease (CAD), may have at least one or more of: (1) atherosclerosis (see e.g., FIGS. 1 and 3A) in at least one coronary artery; (2) coronary microvasculature dysfunction (CMVD) in at least one arteriole or capillary—(see e.g., FIG. 3B); (3) secondary symptoms; and/or (4) at least one myocardial infarct (not shown) that may be reversible or irreversible and/or may be endocardial or transmural.

In another exemplary embodiment, a physician may screen healthy patients for potential and/or actual vessel and/or heart disease utilizing non-invasive and/or less-invasive imaging techniques, which can be utilized to model the heart and identify area of potential and/or actual ischemia. Patients identified with conditions amenable to the various treatments described herein may be subject to further analysis (if desired) and/or treated using the various techniques described herein.

A patient with atherosclerotic CAD may contain one or more atheromas in at least one of their coronary arteries. Atherosclerosis is the gradual buildup of cholesterol and other fatty materials (i.e., atheroma or atherosclerotic plaque) inside the vessel wall of a coronary artery. Such atheromas may build in the left main, right main, circumflex, marginal branch, left descending, and/or posterior descending coronary arteries, such as shown in FIG. 1. As an atheroma grows, it may bulge into the coronary artery, narrowing the interior (lumen) of the coronary artery and partially blocking blood flow. As an atheroma blocks more and more of the coronary artery, the supply of oxygen-rich blood to the heart muscle (myocardium) can become inadequate. If the atheroma further narrows or completely blocks the coronary artery, such narrowing or blockage can cause myocardial ischemia, often resulting in a heart attack. During the heart attack, the area of the heart muscle that was supplied by the narrowed or blocked coronary artery often dies or becomes injured, resulting in a myocardial infarct.

Alternatively, a patient may be diagnosed with CMVD as the leading cause of CAD. The patient may clinically present the same disease symptoms as a person with atherosclerotic lesions in the coronary vessels, but the physician may observe some particularities in the coronary microvasculature as previously discussed herein. Since the blood flows to the heart muscle first through the large coronary arteries, and if no overt blockage and/or occlusion is observed, then the autoregulation response to increased oxygen demand should not be impaired. The coronary arteries should release the vasodilating substances that allow the increase in coronary perfusion in the face of increased oxygen demand. However, once the blood flow with the vasodilating substances continues to flow through branches of thousands of microvasculature networks, any particularities present in the microvasculature can significantly compromise the vasodilating effect. In other words, the vasodilators may be unable to dilate the microvasculature in order to meet the increased demand of blood flow, thus, increased blood flow through undilated microvasculature could significantly increase blood flow resistance. This can disrupt this systematic flow process to control blood distribution and blood resistance, where the overall effect can be significant—i.e., the microvasculature will be unable to meet oxygen demands for proper perfusion. Hence, ischemia may develop leading to a heart attack and/or ischemic injury (myocardial infarct or MI).

The depth, size and/or location of the myocardial infarct may vary based on the location and degree of the narrowing, blockage and/or particularities of the coronary artery. FIGS. 4A through 4E illustrate various embodiments of common locations of myocardial infarcts. Common locations may include lateral wall ischemia (FIG. 4A), inferior wall ischemia (FIG. 4B), septal wall ischemia (FIG. 4C), anterior wall ischemia (FIG. 4D), posterolateral (FIG. 4E), posteroinferior (FIG. 4E), and/or any combination thereof. Furthermore, based on the location and degree of the narrowing or blockage of the coronary artery, myocardial infarct depth through the heart tissue may be visualized.

Figure 5:
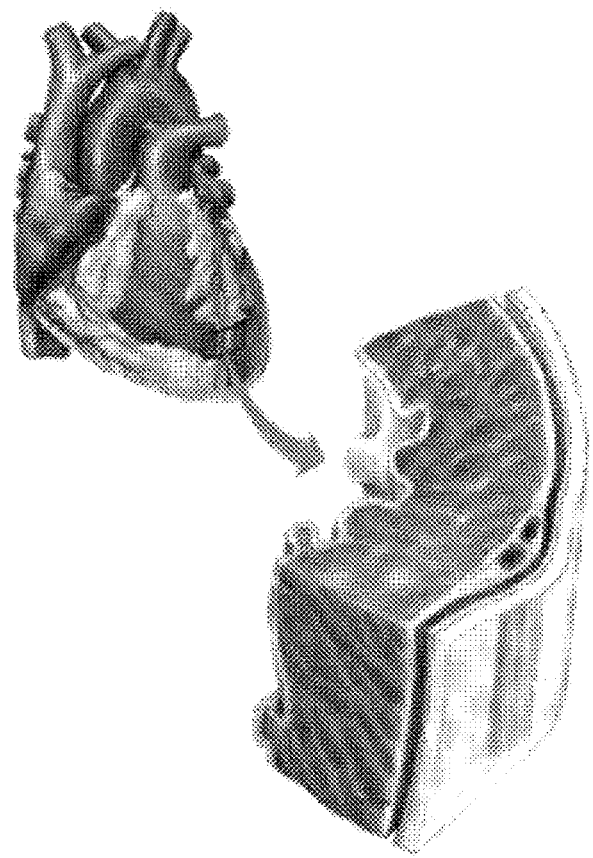
FIG. 5 depicts one embodiment of myocardial tissue layers.
Figure 6:
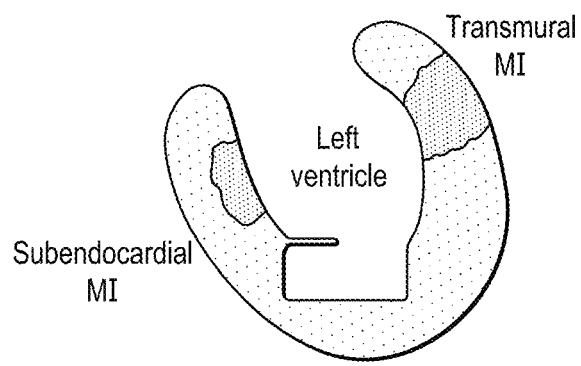
FIG. 6 depicts the anterior view of one embodiment of a left ventricle with subendocardial and transmural infarcts.

FIG. 5 shows one embodiment of a cross-section of a localized area of the heart tissue. The heart tissue may comprise an endocardium (inner lining), myocardium (heart muscle), the epicardium (outer surface), the coronary arteries that branch perpendicularly into the myocardium, the pericardial cavity, and the pericardium (a sac around the heart). Mycardial infarct depths may vary and may be visualized in the epicardial (outer surface of the heart), subendocardial (extends from outer surface of the heart though a portion of the myocardium) and/or transmural (extends from outer surface of the heart through to the inner lining), such as shown in FIG. 6. Such understanding of the severity of the IHD will desirably provide the physician ample information to select and administer the proper angiogenic-based therapy (i.e., location and/or depth of angiogenic treatment in the heart wall).

In another embodiment, the physician may select a patient for prophylactic angiogenic-based therapy when the patient expresses a high risk (or "at-risk") of manifesting IHD. The physician may evaluate various major factors that allows physicians to predict multivariate IHD risk in patients without overt IHD. Such major factors include at least one of family history, age, genetic influences, tobacco use, overweight/obesity, unhealthy diet, physical inactivity, diabetes, hypertension, metabolic syndrome, blood chemistry/immunohistochemistry (i.e., C-reactive protein, triglycerides, and/or oxidative stress markers), tumor markers, gender, ventricular hypertrophy, ventricular function results, various other cardiac function results and/or any combination thereof. Prevention of the manifestation of "at-risk" IHD may be alleviated by angiogenic-based therapy.

For example, in one embodiment, blood tests and/or immunohistochemistry may be performed to reveal a systemic inflammatory response or the concentration of oxidative stress markers (i.e., expression of malondialdehyde (MDA) and 3-nitrotyrosine) in the cardiac tissue. The physician may request laboratory blood tests such as but not limited to troponin I & T, CK-MB, PLAC Test for Lp-PLA2 (lipoprotein-associated phospholipase A2) or Myglobin. The physician may desirably develop an algorithm, use regression equations or other relevant statistical analysis that outlines the results of the major factors and/or any standard diagnostic and imaging tests as described in Table 1 to use for a prediction of at-risk patients. Such understanding of the risk factors associated with IHD will provide the physician ample information to select and administer the proper prophylactic angiogenic-based therapy to reduce their risk and postpone and/or potentially prevent IHD from manifesting.

Imaging

In various embodiments, a physician may collect various two-dimensional (2D) and three-dimensional (3D) images (including via non-invasive and/or minimally-invasive techniques known the in the art and/or developed in the future) containing data that can be utilized to conduct quantitative and/or qualitative analysis of the various imaged tissues. Such quantitative and/or qualitative analysis may include plaque characterization, diagnostic analysis that determines the severity of the IHD or "at-risk" patients, or for non-diagnostic uses, such as image mapping to assist with navigation of relevant tools and/or delivery catheters to reach the region of interest, and/or the collection of additional quantitative data (i.e., perfusion data) to further classify the severity of the disease. In one exemplary embodiment, such collection of data may be used confirm the severity of IHD, preoperatively to identify at least one target region of interest, used intraoperatively to access the at least one target region of interest, and/or used post-operatively to determine the efficacy of the angiogenic-based therapy.

In another embodiment, the physician may obtain digital images of the region of interest by utilizing standard imaging modalities, such as those shown in FIGS. 14A and 14B (i.e., angiographic images with digital gray-value analysis). Some standard imaging modalities are also described in Table 1. For example, a physician may obtain images of a region of interest by utilizing standard angiographic imaging. Once the at least one region of interest is selected, it may be injected and/or otherwise filled with contrast medium. The images can be collected and evaluated real-time and/or stored for further analysis. The angiographic images with the region of interest may be further evaluated by means of electronic data processing (EDP) and/or digital gray-value analysis (a recognized and well-established technique for demonstrating capillary revascularization and/or neoangiogenesis). A plurality of pixels may be selected from within each region of interest and analyzed digitally. Complete blackening of the angiographic films may be rated with a high gray value (i.e., a gray value of 150), and areas without blackening of the film can be allotted a zero gray value. Such images may be viewed for a patient with CAD (in FIG. 14A), and/or for a patient with increased perfusion after angiogenic-based therapy (in FIG. 14B).

Alternatively, the physician may perform quantitative analysis of the microvascular function within a region of interest using stored angiographic images to calculate various angiographic CMVD indexes. Such examples of angiographic CMVD indexes may be myocardial blush and/or Timi Frame Count (TFC). For example, myocardial blush is the myocardial opacification resulting by injection of dye into the coronary arteries. Counting the number of heart cycles required for it to fade out achieves the Myocardial Blush Grade (MBG), which depends on the microcirculation resistance to the dye passage and the efficiency of venous drainage. The Total Myocardial Blush Score is the sum of the MBG of each coronary territory and defines the overall microvascular functionality. Another example is the Timi Frame Count (TFC). The TFC is calculated on the basis of the number of frames required for dye to reach a standardized distal landmark of the considered coronary vessel and a correction factor depending on vessel length. It is related to the velocity at which dye fills coronary vessels and index of microvascular resistance. Similar to the Total Myocardial Blush score, Total Timi Frame Count is the sum of the three major coronary vessel scores, and is useful for a comprehensive view of the coronary microcirculation function.

Figures 19A, 19B:
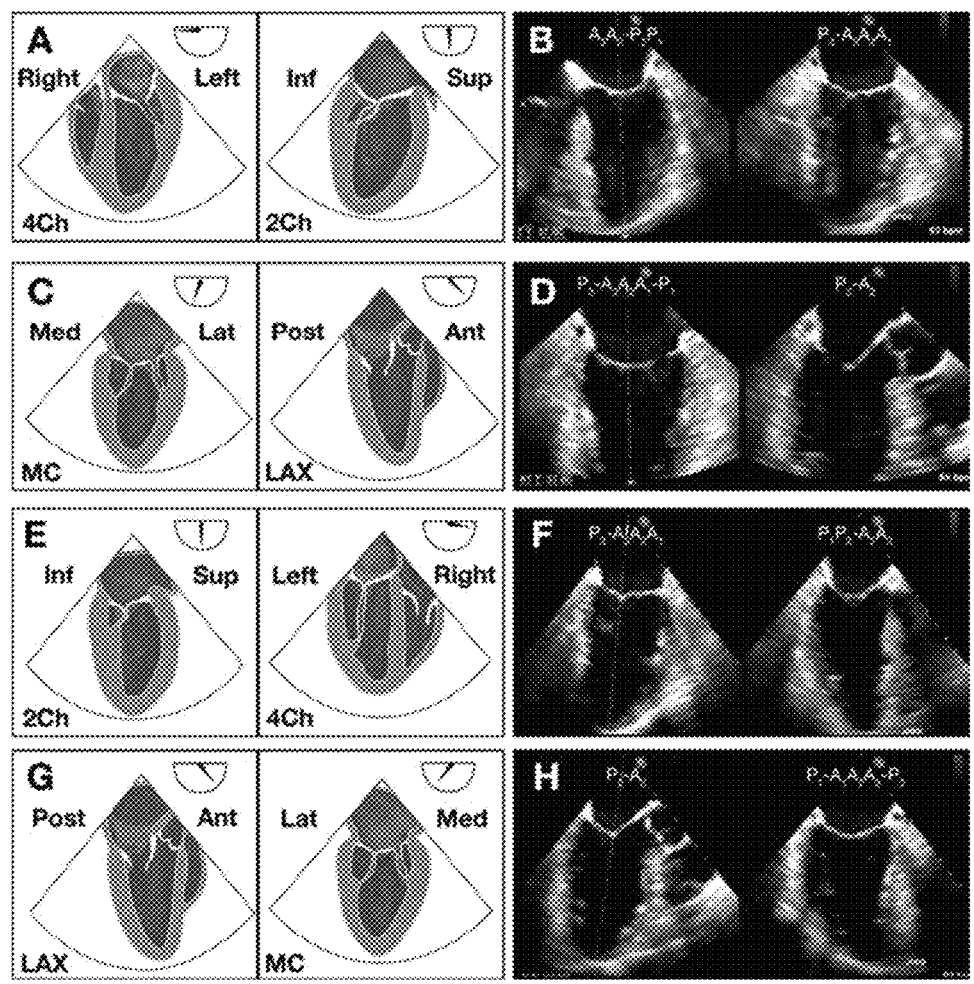
FIGS. 19A and 19B depict one embodiment of Transesophageal Echocardiogram (TEE) images in pictorial and actual views.

However, a wide variety of imaging techniques may be utilized, as the physician should not be limited to only angiographic imaging, and may decide to use TEE as the standard imaging modality. The collection of TEE images could proceed in a routine and organized manner, in which each structure of the heart, the atherosclerotic plaque and the vessels can be examined in several imaging planes for image mapping and/or quantitative measurements. FIGS. 19A and 19B illustrate various exemplary views that may be obtained of a ventricle for image mapping (i.e., locating a region of interest that may have ischemic injury), assessment of cardiac function (i.e., preload, contractility and/or quantitative hemodynamics), pressures (i.e., cardiac output, stroke volume, pulmonary artery, right ventricular systolic pressures), facilitate the conduct and management of the administration of the angiogenic-based therapy (i.e., such that it does not interfere with the progress of the improved intervention), and/or any combination thereof. All images and data collected may be used to detect and assess the severity of CAD, identify areas that may be amenable to treatment and/or determine whether a patient is "at-risk."

In another embodiment, the physician may obtain digital images of the region of interest by utilizing standard Positron emission tomography (PET), serial SPECT imaging and/or any nuclear imaging modality, while optionally using at least one myocardial perfusion agent (hereinafter known as "agent or agents") for enhancing myocardial perfusion imaging. The agents may include 99mTc-sestamibi, thallium Tl 201 chloride, Tc-99m Teboroxime, Tc-99m N-NOET, technetium Tc-99m tetrofosmin and/or any combination thereof. This approach can be especially desirable for plaque characterization, the diagnosis of IHD, diagnosis and localization of infarcts, and/or assessment of global ventricular function. It may be advantageous to potentially include images at rest (i.e., 250 MBq) and stress examination (i.e. 750 MBq), such as shown in FIGS. 15A-15B, and 16A-16B. During such imaging, the physician may choose to inject a single agent or inject a dual agent protocol. Such a dual agent protocol can include the injection of two different agents to capitalize on their respective strengths. One agent may be used during rest imaging and the other may be used during stress imaging, if desired.

Alternatively, other agents may be used, such as SPECT ligands that can be designed to probe various processes of the coronary arteries, coronary microvasculature, and/or atherosclerotic progression and rupture, including chemotaxis, angiogenesis, lipoprotein accumulation, proteolysis, and/or thrombogenicity. Moreover, a few alternative PET tracers may be used, including flurodeoxyglucose (FDG), translocator protein (TSPO) ligands, and/or choline ligands.

Also, in various embodiments the physician may desirably obtain a collection of PET, serial SPECT and/or other nuclear imaging modalities digital images in various axis. Plaque characterization and/or the performance of myocardial perfusion at rest and stress can be evaluated on short axis, vertical axis, and/or sagittal long axis slices. Such collections of images may be collected and evaluated real-time or stored for further analysis. Furthermore, a conventional algorithm may be applied for 3D data reconstruction and display, as well as using a visual semi-quantitative score, which may range from 0 (=no perfusion) to 4 (=normal perfusion), the semi-quantitative scores may be summarized to yield "summed rest score (SRS)" and a "summed stress score (SSS)." These SRS and the SSS may be used as reference levels to assist the physician with the determination of the success of the treatment or need to change treatment protocols.

In another embodiment, the physician may obtain digital images of a region of interest by utilizing a left ventricular electromechanical mapping system (LVEMMS) to evaluate the electromechanical remodeling of a patient's heart. The LVEMMS is a non-fluoroscopic catheter-based magnetic guidance tool ("LVEMM catheter") to target visualization of regions of interest within a three-dimensional (3D) electromechanical map (EMM) of the endocardial surface of the left ventricle. The LVEMMS may include a catheter with a deflectable tip and an injection needle, a handle with printed circuit board (PCB), and a computer mapping system.

The LVEMM catheter may be equipped with a plurality of sensors that may be embedded within the deflectable tip, including a location sensor, a motion sensor and/or electrodes. The LVEMM catheter may be guided by ultralow magnetic fields ($10^{-6}$ to $10^{-5}$ T) that are generated by a triangular magnetic pad positioned beneath a patient. The magnetic fields intersect with a location sensor proximal to the deflectable LVEMM catheter tip, which helps determine the real-time position and orientation of the LVEMM catheter tip inside the left ventricle (LV). The LVEMMS may account for patient movement by placing an external reference patch on the patient's back.

In various embodiments, as the sensor proximal to the deflectable LVEMM catheter tip can desirably be in stable contact with the endocardium, the data collection sequence can be initiated automatically. The LVEMM catheter interfaces with the LVEMM computer mapping system and transmits the collected data for contractility and the electrical viability analysis. For contractility, the LVEMMS computer mapping system uses an algorithm to calculate and analyze the movement of the catheter tip or the location of an endocardial point through systole and diastole. That movement is then compared with the movement of adjacent regions of interest. A quantitative value is obtained (i.e., linear local shortening—LLS), and it is expressed as a percentage that represents the degree of mechanical function of the LV region at that region of interest.

The LVEMM catheter electrodes embedded in the deflectable catheter tip can measure endocardial electrical signals through systole and diastole at a region of interest. The electrical signals may be compared with the movement of adjacent regions of interest. A quantitative value is obtained (i.e., left ventricular unipolar or bipolar voltage—LVUB or LVBV), and it is expressed as millivolts (mV) that represents the intracardiac electrocardiogram of the various regions of interest.

Figures 18A, 18B:
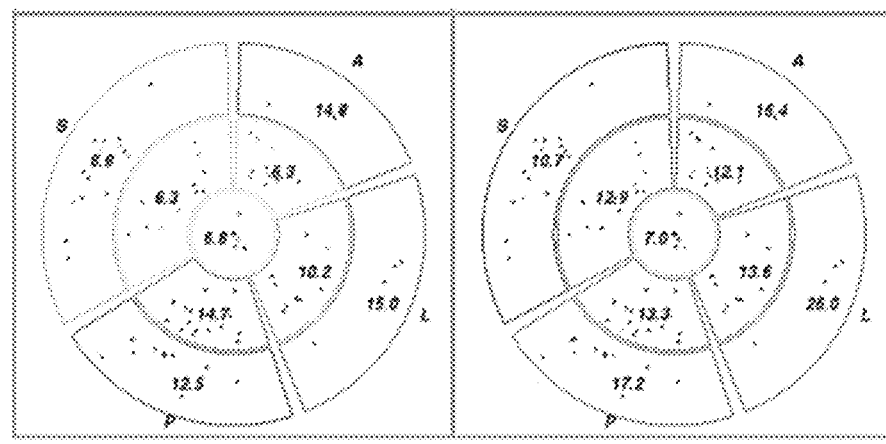
FIGS. 18A and 18B depict an alternate embodiment of Left-Ventricular Electromechanical voltage potential and contractility image maps of the heart.

The LVEMM computer system can desirably create and/or reconstruct electromechanical maps of the left ventricle of the LLS, LVUB and/or LVBV collected data. Such collected data and reconstructed electromechanical maps can provide global and regional contractility data for the left ventricle. The reconstructed endocardial (see FIGS. 18A and 18B) and mechanical function maps (see FIGS. 17A and 17B) can be color-coded in a known manner to assist the physician with interpretation. Furthermore, LVEMM may be used to delineate between infarcts varying in transmurality by using electrical information derived from endocardial voltage potentials, and/or delineate at-risk patients that may not yet have overt IHD. The use of the LVEMM system is advantageous to identify and target specific areas of the heart for treatment, and may be used "off-pump" (i.e., while the heart is beating), if desired.

In another embodiment, the physician may acquire digital images of a region of interest by utilizing standard magnetic resonance imaging (MRI) and/or MRI enhanced with a needle injection catheter that can have a mounted resonant solenoid circuit (coil) at the catheter tip to enable local endoventricular delivery (Corti, Badimon, Mizsei, et al., *MR Guided Local Delivery* (2005), which is herein incorporated by reference in its entirety).

MRIs can provide excellent contrast definition that differentiates soft tissue components on the basis of biophysical and biochemical parameters such as chemical composition and concentration, water content, physical state, molecular motion, perfusion and diffusion. MRIs can also be used to detect and assess atherosclerotic plaque volume, atherosclerotic plaque composition, and/or the extent of infarcted myocardium because of the delayed absorption and release kinetics of gadolinium in such tissue when compared with that of normal myocardium. However, an MRI's ability to visualize a region of interest endoventricularly may be enhanced when accompanied by a delivery catheter equipped with a miniaturized resonant circuit. The miniaturized resonant circuit may serve as a tracking marker, which will desirably be MM compatible and inhibit any imaging artifacts, and minimize potential hazardous heating to catheter and surrounding structures.

The miniaturized resonant circuit may comprise a multi-turn solenoid inductor of Teflon coated silver wire (diameter 0.25 mm) connected in parallel to a miniature chip capacitor (ATC 700A; American Technical Ceramics, Huntington Station, N.Y., USA). The resonant circuit can be tuned to 63.85 MHz after it is embedded into the catheter tip. Ex-vivo experiments may be conducted to test the visualization of the catheter tip with microcoil at various orientations. The catheter tip with microcoil may be immersed in a copper sulphate doped saline phantom solution and rotated by 360° during real-time imaging.

Once the catheter with microcoil is advanced to the ventricle, it can be visually confirmed in apposition to the endocardium, and gadolinium-diethylenetriaminepentaacetic acid (DTPA) and Indian Ink mixture can be injected into the endocardium or myocardium. The injections may be visualized as bright focal intramural deposits with a dark rim (halo). Such bright focal deposits can assist with location and depth of treatment.

Furthermore, MRI may be able to characterize specific atherosclerotic plaque components. Specifically, MRI may be able to differentiate four main plaque components: fibrous cap (and its integrity), lipid-rich/necrotic core, intraplaque hemorrhage, and/or calcification. Such characterization may be able to detect early stages of the plaque to its vulnerable or unstable stage. Moreover, it may be desirous to enhance visualization by the use of dynamic contrast enhancement (DCE). Various contrast agents may be used, including conventional gadolinium-based contrast agents, targeted molecular and cellular contrast agents (i.e., liposomes, nanoparticles, lipoproteins, quantum dots, etc.), iron oxide conjugates, and/or any combination thereof.

In another embodiment, the physician may obtain digital images and quantitative analysis of the region of interest by utilizing a pressure wire catheter. The physician may utilize a guiding catheter to engage the left coronary artery (LAD) or any coronary artery of choice. The physician may infuse intracoronary nitroglycerin prior to advancement of the pressure wire catheter. A coronary pressure wire catheter (0.014 inch wire, Radi Medical Systems, St. Jude Medical, St. Paul, Minn.) may be inserted into the guiding catheter and advanced to the distal portion of the LAD. Maximal hyperemia may be induced by administration of intravenous adenosine or dipyridamole through a cannula in a large peripheral vein for 3 min before and during data acquisition. The physician may choose to administer two or more boli to obtain a hyperemic mean, where the transit time can be measured and the resulting data points can be averaged. The coronary pressure wire catheter may obtain various intracoronary microcirculation measurements. Such intracoronary microcirculation measurements may include blood flow velocity (APV, average peak velocity), mean aortic pressures and mean distal coronary pressures, flow patterns (i.e., DT—diastolic deceleration time or system flow reversal), volumetric blood flow, vasoreactivity, coronary flow reserve (which reflects the amount of increase in coronary perfusion to accommodate increased demand), fractional flow reserve and/or any combination thereof (see Table 2—below). Desirably, the physician may also assess the response to a vasoconstrictor, as well as vasodilation to evaluate microvascular disease.

In another embodiment, the physician may obtain digital images of the region of interest by utilizing Intravascular ultrasound (IVUS), contrast-enhanced ultrasound (CEUS) and/or B mode ultrasound to obtain reproducible views of the microvasculature and/or atherosclerotic composition. IVUS is a miniature high-frequency transducer that is transluminally placed into an affected coronary artery. IVUS can provide cross-sectional images of the vessel, including the vessel wall (the intima and media) to obtain absolute lesion lumen area and other unique stenosis indices. The actual atheroma volume and/or a percentage change in atheroma volume by measuring both actual microvascular lumen diameter and the appearance and thickness of the intima and media may be captured.

The physician may use various combinations of IVUS system platforms that include the imaging catheter and/or the imaging console. Examples of IVUS system platforms may include a 3.5F, 30-MHz short monorail imaging catheter (Sonicath, Boston Scientific, Boston, Mass.) and a HP Intravascular System imaging console (M2400A, Hewlett-Packard, Andover, Mass.) and/or a 2.9F, 30-MHz-long monorail imaging catheter (MicroView, Boston Scientific, Boston, Mass.) and a CVIS imaging console (ClearView, Boston Scientific, Boston, Mass.). Alternatively, the physician may have available varying ultrasound imaging catheter frequencies, 20 mHz to 40 mHz to obtain desired images. One example of a 40 mHz IVUS imaging catheter is the Atlantis SR Pro, commercially available from Boston Scientific of Natick, Mass.

Figure 37A:
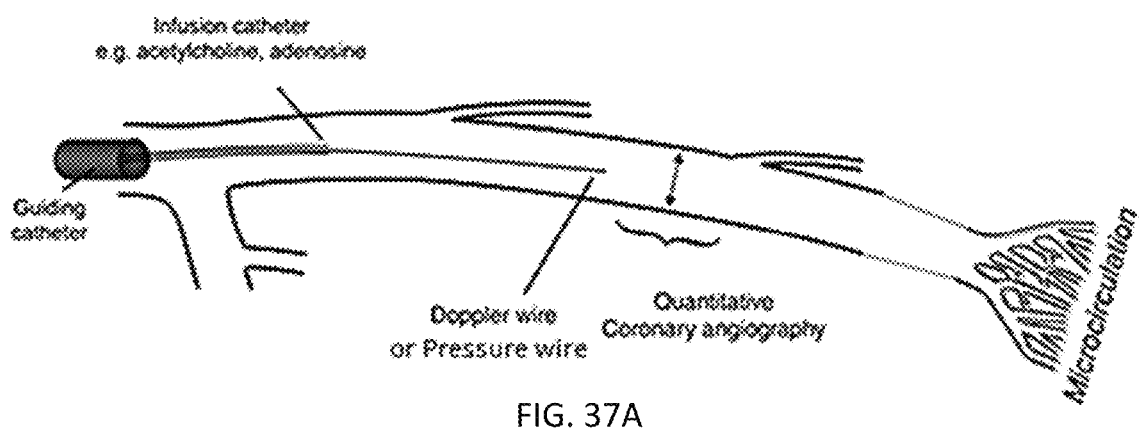
FIGS. 37A and 37B depict one embodiment of performing intracoronary measurements with an IVUS or pressure wire.
Figure 37B:
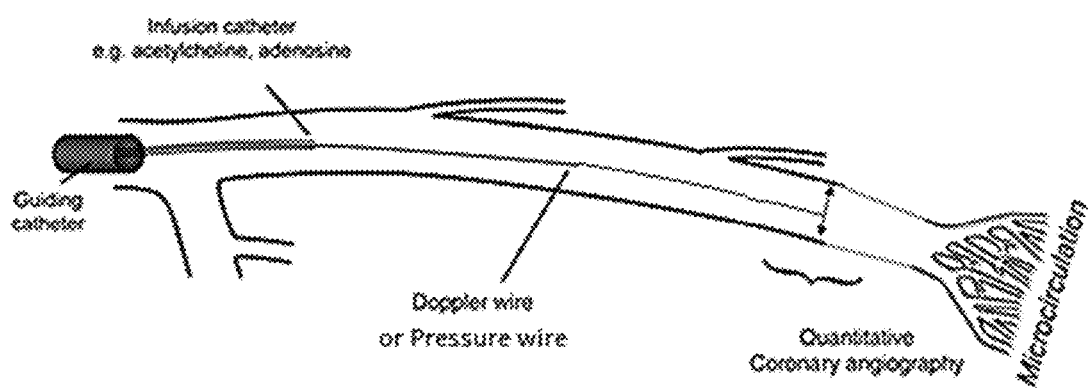

The imaging catheter may be introduced into the target coronary artery (see FIGS. 37A and 37B) through a guiding catheter and/or along a guide wire. The physician may optionally decide to administer nitroglycerin, acetylcholine or other standard medications that obtains maximum vasodilation of the vessel and desirably prevents possible vasospasms. The imaging catheter may be advanced to the distal portion of the vessel near the targeted microvasculature (see FIG. 37B) and/or atherosclerotic plaque under fluoroscopic guidance. The physician may initiate a slow retraction (i.e., approximately 0.5 mm/sec to 1 mm/sec) of the imaging catheter along the length of the vessel to capture the images from the ultrasonic reflections.

In various embodiments, image data can be stored for quantitative analysis of the atherosclerotic plaque and/or vessel wall to calculate various intracoronary microcirculation measurements and/or plaque characterization. Such intracoronary microcirculation measurements may include blood flow velocity (APV, average peak velocity), flow patterns (i.e., DT—diastolic deceleration time or system flow reversal), volumetric blood flow, vasoreactivity, coronary flow reserve, fractional flow reserve and/or any combination thereof (see Table 2—below). The volumetric blood flow may be calculated with additional assessment of coronary lumen area and/or the vasoreactivity can be expressed as a change in coronary blood flow in response to different stimuli (i.e., acetylcholine for endothelial stimulation or adenosine for maximal vasodilator capacity). Furthermore, if there is a pressure sensor incorporated into the IVUS imaging catheter, it may be possible to calculate the Index of Microvascular Resistance (IMR).

TABLE 2

Intracoronary Microcirculation Measurements

| No. | Intracoronary Measurements | Intracoronary Calculations |
|---|---|---|
| 1 | Volumetric Blood flow | ½ × APV × lumen area |
| 2 | Vasoreactivity | change in coronary blood flow in response to different stimuli (i.e., acetylcholine for endothelial stimulation or adenosine for maximal vasodilator capacity |
| 3 | Coronary Flow Reserve | Hyperemic (adenosine induced) APV/basal APV |
| 4 | Fractional Flow Reserve | Mean Distal Coronary Pressure/mean proximal coronary pressure during hyperemia |
| 5 | Index of Microcirculatory Resistance (IMR) | Distal coronary pressure × hyperemic transit time |
| 6 | Hyperemic Mean Transit Time | Man transit time of 3 × 3 ml boluses of room temperature saline |
| 7 | Atheroma Cross-Sectional Area (CSA) | External Elastic Membrane CSA minus Lumen CSA |

In various embodiments, a conventional grayscale IVUS may be used for plaque characterization and/or enhanced with spectral analysis. Spectral analysis may be performed from the radiofrequency signal, known as virtual-histology IVUS (VH-IVUS). VH-IVUS can accurately detect the presence of fibrous, fibrolipidic, calcified, and/or calcified-necrotic regions from plaques. Furthermore, conventional grayscale IVUS and VH-IVUS may be combined to classify the plaques into the specific stages as discussed herein.

In various embodiments, a B-mode ultrasound may be used to measure carotid intima-media thickness (CIMT). It is a one-dimensional measurement that identifies the boundaries at the intima-lumen and adventia-media. It is an attractive imaging modality because it is fairly non-invasive and inexpensive.

In various embodiments, a CEUS may be used to enable the CIMT to provide information about microvasculature, atherosclerotic plaque composition, plaque neointimal microvasculature, plaque inflammation, and/or other structural information. Several types of contrast agents (microbubbles) may be used, which act as blood pool agents. The microbubbles may consist of a lipid or albumin shell filled with an inert gas. For example, the microbubbles may be retained in inflamed tissue through integrin and complement-based adherence to damaged endothelium and/or monocytes, which are themselves attached to the endothelium.

In various embodiments, IVUS, B mode ultrasound, CEUS or pressure wire may be performed prophylactically, and/or at 1 to 12 months after post-transplantation (or any time after post-transplantation) as an important approach to identify patients at high risk for future cardiovascular events, to potentially adjust the therapeutic dosing of the angiogenic-based therapy, and/or determine the effectiveness of the treatment. Such strategies may induce significant improvements in long-term prognosis.

Figure 41:
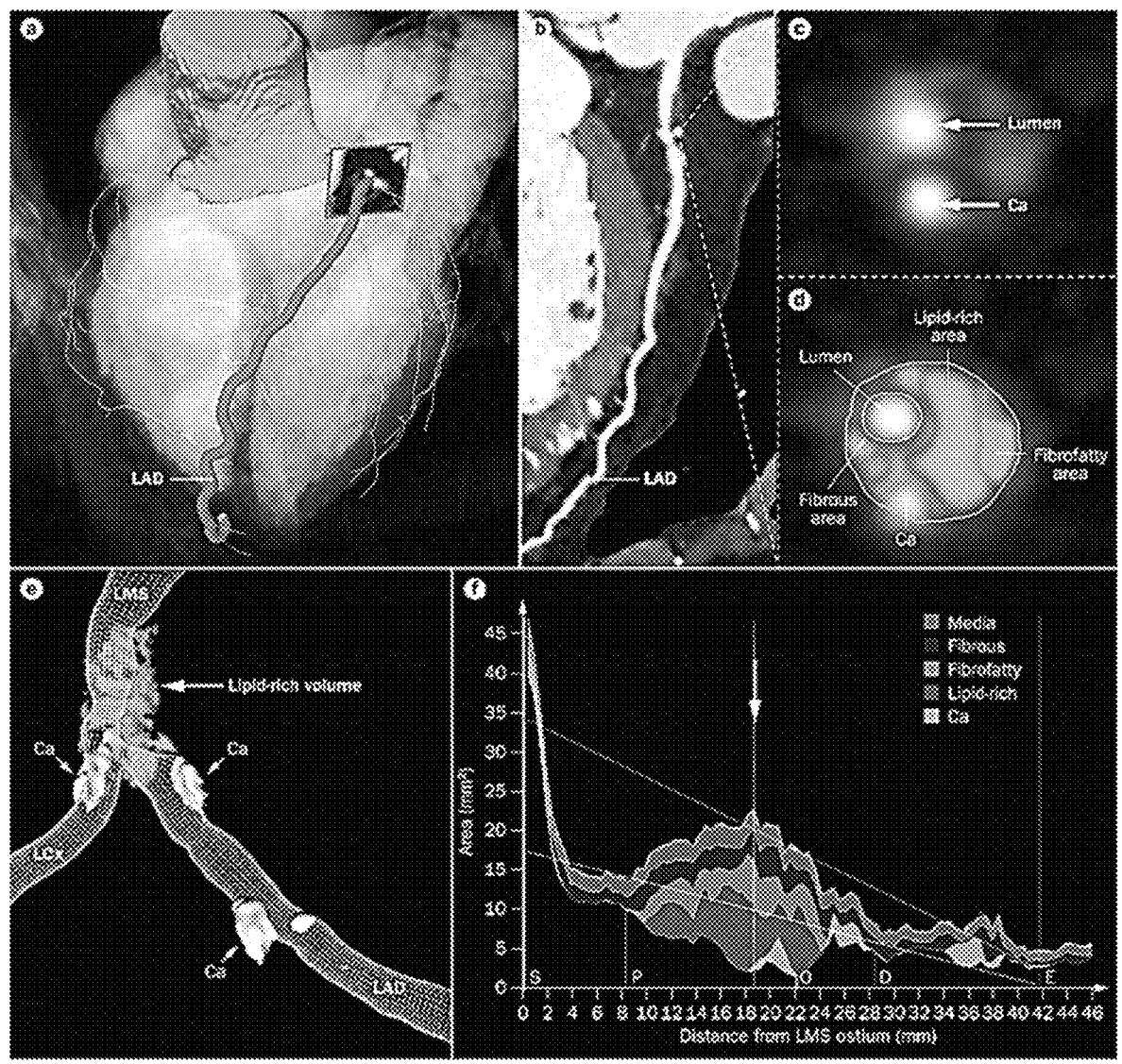
FIG. 41 depicts various CCTA images of coronary arteries, coronary microvasculature and/or plaque composition.

In various embodiments, computed tomography (CT) may be performed to characterize atherosclerotic plaque and perfusion data of the coronary arteries and/or the coronary microvasculature (see FIG. 41). The submillimeter spatial resolution and excellent image quality of modern computed tomography (CT) scanners allow coronary atherosclerotic lesions, coronary arteries and/or coronary microvasculature to be detected, characterized, and quantified. Furthermore, computation fluid dynamics and multiplanar reconstruction allow the calculation of lesion-specific endothelial shear stress (ESS) and fractional flow reserve (FFR), which add functional information to plaque assessment using CT. The combination of morphologic and functional characteristics of coronary plaques might enable noninvasive detection of plaques at all stages, as well as vulnerable plaques in all subcategories. Other specific features may be included to enhance visualization, such as color overlay with adaptive threshold settings, micro-CT (massively increased resolution to the sub-micron level), and magnified projections of structures to allow scrolling and/or interpolation through cross-sectional planes.

For example, FIG. 41 illustrates one embodiment of plaque and vessel characterization and quantification using Coronary computed tomography (CCTA) angiography imaging. In subportion "a" of the image is depicted a segmented whole coronary tree with LAD indicated. The coronary centerlines and the aorta are shown and a box indicates plaque of interest. In subportion "b" the image depicts a curved multiplanar reconstruction of the left anterior descending (LAD) artery. Dotted lines indicate a partially calcified, positively remodeled plaque in the LMS bifurcation. In subportion "c" the image depicts the left main stem (LMS) plaque cross-section from FIG. 41b. In subportion "d" the image depicts the LMS plaque cross-section with shaded or color overlay derived with adaptive threshold setting. The lipid rich (low CT attenuation) plaque components are shown in the middle, with fibro-fatty tissue shown at the periphery, fibrous tissues darkly shaded and calcium shown in white. In subsection "e" the image depicts a volumetric assessment of the lipid rich plaque core, and the core's spatial relation to the lumen (mesh) and calcium (white). In subsection "f" the image depicts a graph that illustrates the areas of different plaque components. The shading scheme corresponds to that of subsection "d." Such detailed images may allow a physician to characterize the plaque, determine the depth of treatment and/or the perimeter of the region of interest for administration of the angiogenic-based therapy.

In another embodiment, the physician may decide to utilize one or more imaging modalities (i.e., multi-imaging protocols) as described herein, in series and/or parallel, to obtain various 2D and/or 3D image data of the region of interest, and/or conduct quantitative and/or qualitative analysis. Each type of image data collected may be stored for further analysis, quantification and/or overlaid to determine the best mechanism to assess microvascular function, as well as patients that are "at-risk" of manifesting IHD.

Placement within a Treatment Group

Patients may present with clinical evidence of (or have been diagnosed with) IHD or have a risk of developing IHD that may be amenable to the various angiogenic-based therapy treatments described herein. After the physician has reviewed the patient's medical history, imaging, and/or quantitative testing results, the physician may desirably determine whether the patient qualifies for angiogenic based therapy. The physician may subsequently recommend or suggest that the patient be placed in a specific treatment group to receive the angiogenic-based therapy treatment that will best delay, prevent, reverse and/or cure the progression of the IHD. The types of angiogenic-based therapy treatment groups may include treatment that (1) revascularize cardiac tissue; (2) repair and/or regenerate cardiac tissue; (3) regulate localized cell growth, migration, differentiation, and/or survival; (4) prophylactically treat cardiac tissue to prevent manifestation of IHD; and/or (5) stabilize atherosclerotic plaques.

Revascularization Group

In one exemplary embodiment, a physician may suggest that a patient qualifies for an angiogenic-based therapy treatment group that provides localized revascularization therapy to the patient's coronary vessels and/or microvasculature in the heart. This may be accomplished by (1) locating the targeted region of interest in an IHD patient's biological or transplanted heart; and (2) administering the angiogenic-based therapy to the targeted region of interest. The targeted region of interest may include a biological or transplanted heart, which may have at least one of: blocked or partially blocked coronary vessel (i.e., the presence of obstructive CAD), at least one blocked or partially blocked coronary microvasculature in the presence obstructive CAD, at least one coronary microvessel experiencing spasms, at least one coronary microvasculature with endothelial dysfunction, and/or any combination thereof.

In one example, the physician may place the patient in the angiogenic-based therapy group that is focused on revascularizing heart tissue due to a recent donor heart transplant. Heart transplant patients may have a history of transplant vasculopathy (TV) during the first three years after transplantation. TV is a progressive disorder that mainly affects the microcirculation and sometimes the coronary arteries. Studies have shown an increased baseline myocardial blood flow during the first year post-transplantation, and favorable microcirculatory dilation capacity during the first three months. One year after the transplantation both baseline myocardial blood flow and microvascular function tend to normalize. At three years post-transplantation, the hyperemic response to vasodilator stress becomes impaired, despite normal baseline myocardial blood flow. Impaired microcirculation can be one of the leading causes of allograft failure and mortality in heart transplantation. Such effect of the microcirculation of the heart can be known as CAV MVD and may contain similar particularities within the microvasculature as discussed herein.

Angiogenic-based revascularization treatments can be a viable therapeutic strategy for select patients with CAV MVD. A region of interest may include at least one cardiac tissue layer that can be targeted, where CAV MVD can be detected. Detection may occur through a plurality of qualitative (imaging) and/or quantitative diagnostic methods, including endothelial dysfunction measurements, TFCs, MBGs, LVEMM reconstructed endocardial contractility and mechanical function maps, hyperemic transit time, mean aortic and distal coronary pressures, fractional flow reserve (FFR), index of microcirculatory resistance (IMR), and/or any combination thereof, including by using a coronary pressure wire (i.e., Radi Medical Systems, St. Jude Medical, St. Paul, Minn.), Doppler wire and/or any other relevant collection device. Any significant gradient changes or scores that are measured may indicate the presence of the localized CAV MVD.

For example, the physician may locate the region of interest where coronary blood flow is not affected by the microvascular disease (before a pressure gradient is not observed or where the flow is presumed normal) and/or the region of interest adjacent to the diseased microvascular network. Desirably, the physician may attempt to compare the diseased region of interest to a non-diseased region of interest. The physician may create one or more pathways proximate or adjacent to the region of interest to create a new collateral microvascular network and bypass the diseased microvascular network to improve blood flow distribution and decrease resistance. The patient may receive one or more treatments throughout the lifetime of the transplant to replace or bypass any subsequently diseased microvasculature. Such treatments may increase the perfusion to the targeted region of interest and meet oxygen demands to improve long-term outcomes/survival of patients, as well as reduce or eliminate secondary symptoms of angina, cardiac syndrome X, shortness of breath, lack of energy, fatigue, etc. Alternatively, a similar treatment may be administered to a patient with their biological heart that was diagnosed with CAD originating from the coronary microvasculature.

In another example, the physician may place the patient in the angiogenic-based therapy group that is focused on revascularizing heart tissue due to detectable atherosclerotic disease in the coronary arteries. The physician may target a region of interest within the heart vasculature. A region of interest may include at least one coronary artery and/or coronary microvasculature, where atherosclerotic disease can be detected. Detection may occur through one or a plurality of standard qualitative (imaging) and/or quantitative diagnostic methods, such as described herein. Such quantitative and/or quantitative diagnostic methods may be used to locate the region of interest where the atherosclerotic lesion is observed, and/or select an area proximate or adjacent to the atherosclerotic lesion, where the autoregulation response should not be impaired (i.e., before a pressure gradient is not observed or where the flow is presumed normal) from endothelial dysfunction. The physician may create a pathway originating from the proximate or adjacent region of interest to create a new collateral microvascular network.

As a result, treatment may induce the creation of a new collateral network that is positioned in an area adjacent to an atherosclerotic plaque within the coronary artery and/or microvasculature, where perfusion responds normally to autoregulation. The placement of the new microvascular network should allow the vasodilators to reach the microcirculation and properly control the blood flow distribution and resistance. The physician may also optionally administer stabilization treatments and/or remove the atherosclerotic lesion using standard techniques known in the industry prior to and/or after angiogenic-based therapy. Non-removal of the atherosclerotic lesion may prevent microemboli from dislodging and causing microvascular obstruction. The patient may receive one or more stabilization treatments to prevent, inhibit and/or stabilize atherosclerotic lesions in different locations in the coronary vessels.

Administering such revascularization treatments may (1) normalize the autoregulation response to increased oxygen demand stimuli, (2) increase the perfusion to the targeted region of interest and/or adjacent cardiac tissue layers, (3) reduce and/or eliminate potential ventricular dysfunction or cardiac remodeling, and (4) improve long-term outcomes and/or survival of patients.

Repair and/or Regeneration Group

In one exemplary embodiment, a physician may suggest that a patient qualifies for angiogenic-based therapy that provides localized repair and/or regeneration treatments to the heart. This may be accomplished by administering an angiogenic-based therapy to a targeted region of interest in an IHD patient's heart. The targeted region of interest may include damaged or injured cardiac tissue, where the damage or injury may have been manually inflicted by excision of infarcted or non-infarcted tissue and/or a damage or injury already inflicted by at least one infarct. The angiogenic-based therapy may promote angiogenesis, as well as stimulate proliferation of many cell types involved in wound healing, including endothelial cells, fibrobasts, and/or keratinocytes required for tissue repair. This may lead to activation of the angiogenic-based therapy's mitogenic and chemotactic characteristics to induce the wound healing response, resulting in the regeneration and/or repairing of the damaged cardiac tissue with new cardiac tissue that replaces the damaged or injured tissue. Alternatively, the angiogenic-based therapy may be administered to induce encapsulation of the damaged tissue with new cardiac tissue, where the new cardiac tissue can potentially form a membrane or film over the damaged tissue. Furthermore, the physician may desirably administer a dual therapy protocol, where the patient may first receive the revascularization therapy and subsequently receiving the repair and/or regeneration therapy treatment after a designated amount of time.

The employment of repair and/or regeneration therapy treatments can provide many advantages, including: (1) restoring original contractile behavior of the localized cardiac tissue, infarct and/or regions proximate to infarct; (2) reducing and/or eliminating potential ventricular dysfunction or remodeling; (3) reducing size of the infarct; and/or (4) repairing or restoring tissue from irreversible infarcts.

FIGS. 7A through 8B illustrate top and side views of transmural and/or subendocardial infarct(s) that may be treated with various therapies described herein. The physician may administer localized treatments by injecting or implanting the angiogenic-based therapy within the region of interest from the endocardium through to the at least one heart tissue layer, such as depicted in FIG. 5. For example, if the patient has at least one transmural infarct, the physician may inject or implant the angiogenic-based therapy from the endocardium through to the epicardium as shown in FIG. 7A, following a desired path within the region of interest. In addition, the physician may desirably inject or implant the angiogenic based therapy from the center of the infarct to the perimeter of the infarct as shown in FIG. 7B, following a desired path.

Alternatively, the physician may desirably inflict damage or injury on the infarct or on non-infarcted tissue (not shown) that is adjacent to infarcted tissue. FIGS. 9A and 9B illustrates one embodiment of at least a portion of the infarcted tissue being excised by any standard techniques known in the art. Such excision of tissue may include the endocardium and at least some portion of the myocardium, and the infliction of the wound may promote some level of an angiogenic reaction, as well as potentially stimulate migration and/or proliferation of many cell types involved in wound healing, including endothelial cells, fibrobasts, and/or keratinocytes required for tissue repair.

Regulation Group

In another exemplary embodiment, a physician may suggest that a patient qualifies for angiogenic-based therapy treatment group that provides for localized regulation treatments to the heart of IHD patients. This may be accomplished by administering the angiogenic-based therapy to a targeted region of interest in an IHD patient's heart. The targeted region of interest may include at least one of: (1) infarcted and/or non-infarcted cardiac tissue layer(s); (2) coronary microvasculature and/or coronary artery and/or (3) an area that is proximal or adjacent to infarcted cardiac tissue layer, non-infarcted cardiac tissue layer, coronary artery, and/or coronary microvasculature.

Figure 10A:
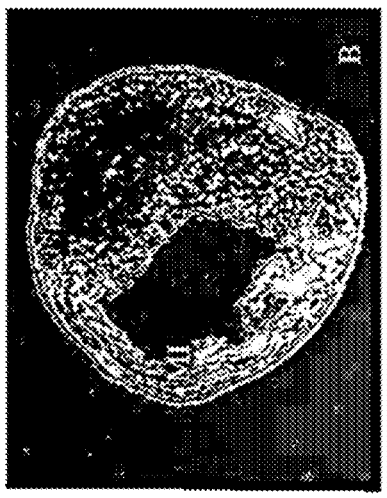
FIGS. 10A-10F depict various embodiments of SPECT imaging of the heart during rest and stress testing.
Figure 10B:
Figure 10C:
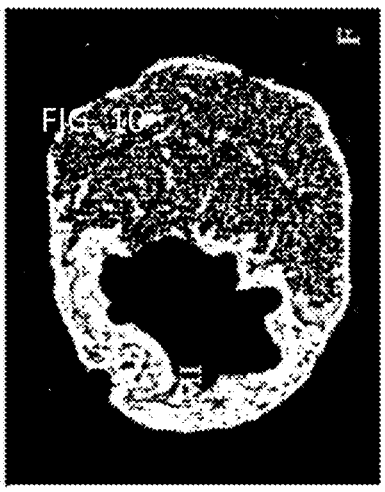
Figure 10D:
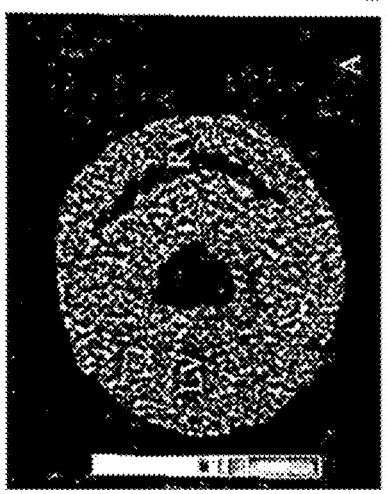
Figure 10E:
Figure 10F:
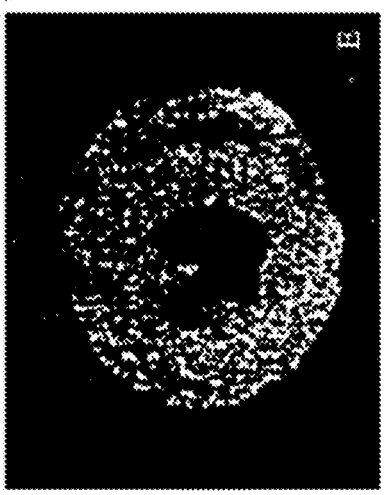

The angiogenic-based therapy in this embodiment may play a role in inhibiting the reparative process that is quickly initiated to rebuild an infarcted myocardium with granulation or fibrous tissue formation that eventually forms into scar tissue to maintain structural integrity of the ventricle. The fibrous tissue reparative process occurs in the infarcted myocardium and in remote sites adjacent to the infarcted myocardium. Such remote sites may include adjacent non-infarcted cardiac tissue, which may include regions of the myocardium, border/perimeter area of the MI, coronary microvasculature and/or coronary arteries. Once a patient experiences an MI, oxidative stress (i.e., oxygen depletion) occurs in the infarcted myocardial area triggering many unwanted cellular reparative processes within the infarcted area and remote sites, such as those shown in FIGS. 10A through 10F. For example, oxidative stress may trigger the recruitment of leucocytes, up-regulate the expression of transforming growth factor $\beta$ (TGF-$\beta$1), promote fibroblast proliferation and/or promote type I collagen gene expression in cardiac fibroblasts into the infarcted region and/or remote sites to initiate cardiac repair. FIGS. 10A, 10C and 10E show the low levels or no levels of TGF-$\beta$1, ACE and AT1 receptors. However, post-MI, FIGS. 10B, 10D and 10F illustrate the contrasting presentation of TGF-$\beta$1, ACE and AT1 receptors present in the infarcted and non-infarcted myocardium.

Desirably, the physician may administer the angiogenic-based therapy to reduce or eliminate any negative regulatory effects caused by oxidative stress, which may include angiogenesis and/or regulating the increased expression of transforming growth factor $\beta$ (TGF-$\beta$1), matrix metalloproteinases (MMPs), differentiation of fibroblasts (myoFb, interstitial, and/or adventitial fibroblasts), renin, macrophage activity, angiotensin-converting enzyme (ACE) binding, and/or Angiotensin I and II receptors, and/or any combination thereof.

Figure 11A:
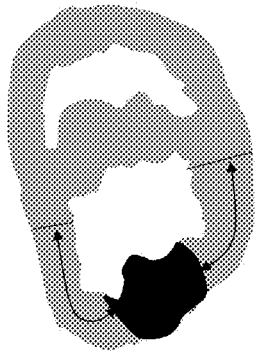
FIGS. 11A-11B depicts various views of an alternate embodiment of localized, targeted angiogenic-based therapy treatment.
Figure 11B:
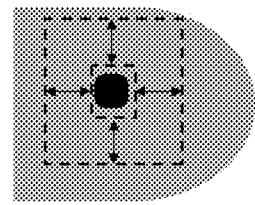

FIGS. 11A and 11B illustrate one embodiment of a type of treatment that intends to regulate the effects of fibrous tissue formation by administering angiogenic-based therapy to a patient that may have a transmural infarct. The physician may desirably select at least one region of interest that includes a quantifiable distance adjacent to the infarcted tissue for injecting at least one treatment or deploying at least one implant that may be proximal or adjacent to infarcted cardiac tissue. The physician may inject or implant from the endocardium through to the epicardium (see FIG. 10A), as well as the perimeter adjacent to the infarct (see FIG. 10B). Alternatively, other types of infarcts may be treated, such as an epicardial or endocardial infarct, as well as administering treatments within the MI itself.

Such regulating angiogenic-based therapy may (1) develop or restore original contractile behavior of the localized cardiac tissue by allowing the repairing and/or regenerating of cardiac tissue as described herein, rather than granulation or fibrous tissue formation; (2) reduce or eliminate cardiac tissue (i.e., myocardial) remodeling to non-infarcted cardiac tissue and/or vessels sites adjacent to infarcted tissue sites; (3) reduce or eliminate potential ventricular dysfunction; and/or (4) reduce the overall size of infarcts.

In another exemplary embodiment, the angiogenic-based therapy may provide for localized treatments to regulate the regression of atherosclerotic plaque in the heart of IHD patients. Atherosclerotic plaques are highly dynamic, and are able to progress, stabilize or regress depending on their surrounding environment. However, atherosclerotic plaque regression would be the return of the arterial wall to its initial state. The return to its initial state may encompass a variety of processes that can be grouped into three main areas: removal of lipids and necrotic material from tunica intima; restoration of endothelial function and repair of denuded areas to allow endothelial cells (ECs) to return to homeostasis; and cessation of vascular smooth muscle cell proliferation.

Figure 40:
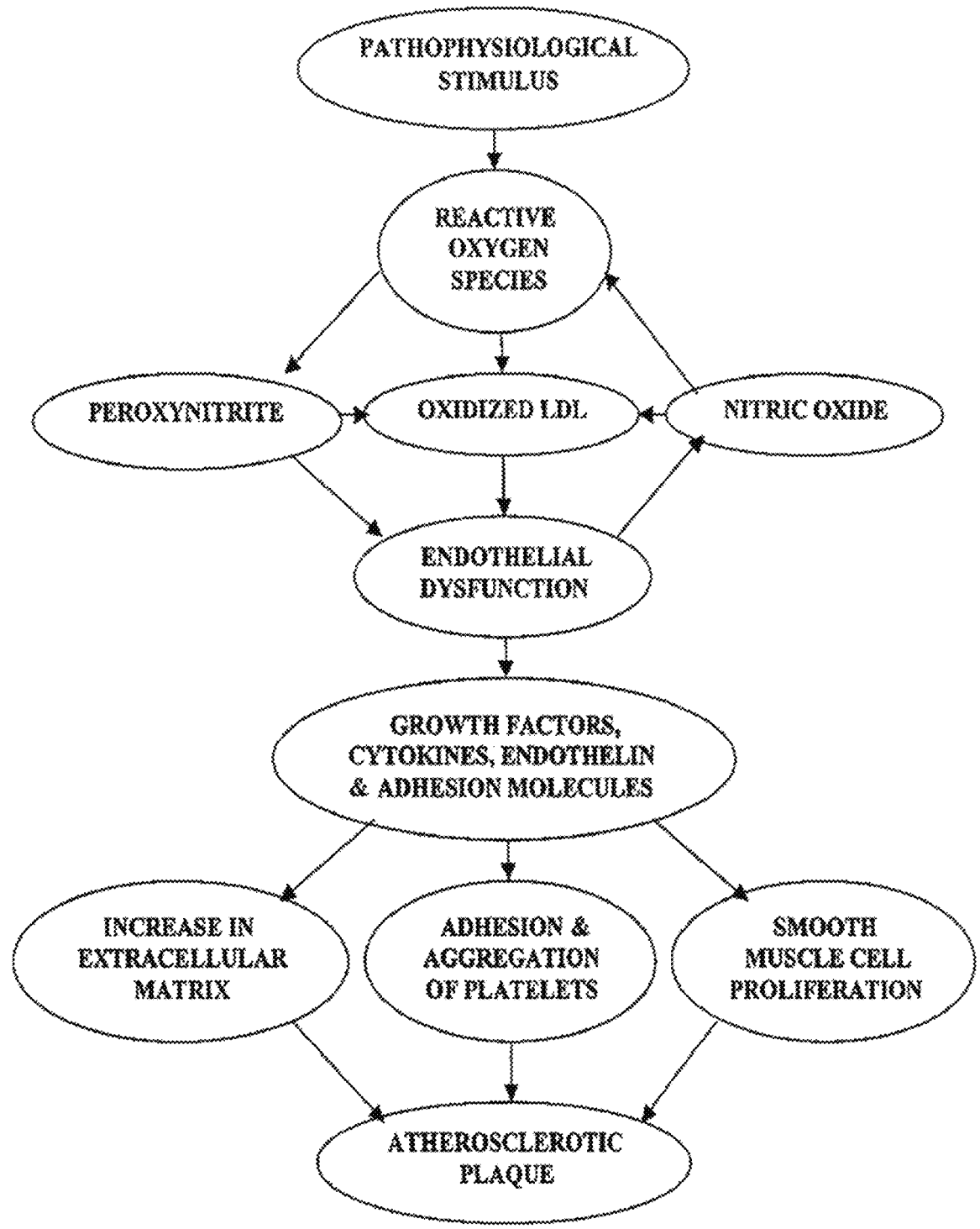
FIG. 40 depicts a flowchart describing one embodiment of the formation of atherosclerotic plaque.

Atherosclerosis is initiated by the response of ECs to injury caused by myriad noxious or pathophysiological stimuli (i.e., major and minor risk factors) including hyperglycemia, hypertension, hyperlipidemia, infectious agents, obesity, modified lipoproteins, homocysteine, nicotine, free radicals, altered changes in arterial blood flow shear stress and normal spontaneous metabolic damage. This initial damage induces a loss of basal endothelial homeostasis causing endothelial dysfunction (see e.g., FIG. 40).

The resulting increase in endothelial permeability permits the accumulation of low-density lipoprotein (LDL) and cellular debris within the tunica intima of the vessel wall, eventually leading to endothelial activation. Once activated, ECs produce an array of chemoattractant cytokines such as monocyte chemoattractant protein-1, macrophage colony-stimulating factor, interferon-g, platelet-endothelial cell adhesion molecule-1, interleukin (IL)-1, IL-6 and tumor necrosis factor-a (TNF-a), creating a pro-inflammatory environment that attracts circulating monocytes and T lymphocytes. Normally, ECs do not express molecules that facilitate the adhesion of circulating leukocytes. However, activated ECs express vascular cell adhesion molecules such as intercellular adhesion molecules (ICAMs), E-selectin and P-selectin, which mediate leukocyte adhesion and infiltration. Endothelial-derived cytokines subsequently drive the differentiation of monocytes into macrophages, which use pattern recognition receptors to sequester LDL, modified LDL, free cholesterol (FC) and cholesteryl esters. Together, activated leukocytes and ECs continue to produce proinflammatory cytokines and growth factors that promote the transition of smooth muscle cells from a quiescent, contractile phenotype to an active and proliferative synthetic phenotype that deposits extracellular matrix at the site of injury, forming a fibrous cap. Continued exposure to various noxious stimuli, in conjunction with a proinflammatory environment, further exacerbates plaque severity, perpetuates plaque progression, and promotes plaque destabilization, resulting in plaque rupture which manifest as acute events such as stroke or myocardial infarction.

The regulation of plaque regression may be accomplished by administering the angiogenic-based therapy to a targeted region of interest in an IHD patient's heart. The targeted region of interest may include at least one coronary artery or coronary microvasculature (1) with and/or without the presence an atherosclerotic plaque, and/or (2) with or without the presence of vascular endothelial dysfunction. The angiogenic-based therapy may regulate the sequences of events that lead to plaque progression, such as the specific cellular and molecular pathways that are responsible for the pathological components of plaque.

Targeting the specific cellular and molecular pathways may elicit better plaque regression and returning the vascular endothelial layer to its initial state by facilitating its mitogenic and/or chemotactic properties (i.e., resolving endothelial dysfunction). The properties may include: (1) hemostasis and inflammation; (2) tissue formation and re-epithelialization; and/or (3) remodeling of the targeted region of interest. The properties may facilitate the actions of macrophage, fibroblast, and blood vessel migration into the damaged tissue, with proliferation and migration of nearby epithelium to build a new vascular epithelial layer.

The new vascular epithelial layer may now properly perform its vascular function, which includes regulation of vascular tone, formation of nitrous oxide (NO), maintenance of the composition of subendothelial matrix, proliferation of smooth muscle cells (SMCs), coagulation, fibrinolysis, permeability of lipoproteins and plasma proteins, and adhesion and migration of blood cells. More specifically, the resident macrophages and foam cells may regain motility and rapidly migrate on environment improvement, moving both lipids and necrotic material to regional lymph nodes. Neighboring endothelial cells can proliferate and replace dead and dysfunctional cells. Circulating endothelial progenitor cells can similarly restore vessel function. Finally, advential angiogenesis and/or abrogation of smooth muscle cell proliferation can occur secondarily to these processes, resulting in return of homeostasis and proper functioning of the coronary artery and/or the coronary microvasculature.

Prophylactic Group

In another exemplary embodiment, the physician may suggest that the patient qualifies for an angiogenic-based therapy that may provide for localized prophylactic treatments to the heart of "at-risk" patients to prevent the overt manifestation of IHD. Physicians may select and/or predict patients to be treated by evaluating various major and/or minor risk factors that allows physicians to predict multivariate IHD risk in patients without overt IHD. Such major factors include at least one of family history, age, genetic influences, tobacco use, overweight/obesity, unhealthy diet, estrogen deficiency, physical inactivity, diabetes, hypertension, hypercholesteremia, metabolic syndrome, blood chemistry (i.e., C-reactive protein, triglycerides), gender, ventricular hypertrophy, cardiac function results and/or any combination thereof.

Such major and minor risk factors (i.e., pathophysiological stimuli) have been associated with impaired function of the endothelium as discussed herein. Normally, a proper functioning vascular endothelium is not only an anatomic barrier to prevent the extravasation of circulating blood into the vessel wall, it also maintains vascular homeostasis by (1) modulating vascular tone; (2) regulating solute transport into cell components of the vessel wall, local cellular growth, and extracellular matrix deposition; (3) protecting the vessel from the potentially injurious consequences of substances and cells circulating in blood; and/or (4) regulating the hemostatic, inflammatory and reparative responses to local injury. However, such major and minor risk factors can contribute to endothelial dysfunction, where the vessel wall may begin to promote inflammation, oxidation of lipoproteins, SMC proliferation, extracellular matrix deposition or lysis, reduction of nitric oxide (NO), accumulation of lipid-rich material, platelet activation and/or adherence of the proliferation of cells. Consequently, endothelial dysfunction may facilitate the development and clinical expression of atherosclerosis or CMVD.

Therefore, early evaluation and/or detection of endothelial dysfunction may be useful in identifying "at-risk" patients because endothelial dysfunction of the epicardial coronary arteries and/or the CMVD typically precedes the development of IHD. Although there are a variety of impaired responses suggestive of endothelial dysfunction, the diminished release of NO into the coronary wall due to impaired synthesis and/or excessive oxidative degradation is a common consequence. Diminished NO bioactivity causes constriction of the coronary arteries or CMVD during exercise or during mental stress leading to decreased coronary blood flow (i.e., hypoperfusion), as well as facilitate vascular inflammation that could lead to oxidation of lipoproteins and foam cell formation, the precursor of atherosclerosis, rather than dilating the coronary arteries and/or the CMVDs in the presence of intact endothelium. The decrease or blocking of nitric oxide production in the systemic circulation also increases coronary vascular resistance, suggesting that nitric oxide release may be of physiological importance in the regulation of basal systemic and coronary tone, especially at the level of the arterioles (resistance vessels) in these vascular distributions. There may be numerous invasive and non-invasive techniques that can evaluate endothelial function to administer angiogenic-based therapy to inhibit, prevent, reverse or delay endothelial dysfunction for "at-risk" patients.

In one embodiment, the physician may confirm with localized electromechanical mapping (EMM) of the heart to detect any myocardial function abnormalities due to endothelial dysfunction. EMM may identify one or more viable or normal regions of interest in at least one layer of the cardiac tissue to determine a unipolar voltage (i.e., 7 mV or greater), such as shown in FIG. 12A. The EMM may subsequently identify one or more adjacent regions of interest that may be associated with impaired or abnormal wall shortening to determine linear local shortening (i.e., 12% or less), such as shown in FIG. 12B. Once the impaired or abnormal region of interest has been confirmed, the physician may administer the angiogenic-based therapy through at least one cardiac tissue layer (parental) and/or the surrounding localized perimeter of at least one cardiac tissue layer (topical) within the region of interest. Furthermore, the physician may decide to treat the patient at the most severely impaired or abnormal region(s) of interest at the first visit, and may subsequently assess the change in linear local shortening at follow-up visits and/or initiate treatment in other areas that may be less severely impaired or abnormal. Angiogenic treatments may be applied to damaged tissues, at-risk tissues and/or to surrounding healthy tissues (or various combinations thereof), as well as to anatomical regions intermediate such tissues such as tissue boundaries.

In other embodiments, the physician may employ invasive and non-invasive techniques for assessing endothelial function (D. Tousoulis et al., *Evaluating Endothelial Function in Humans: A Guide to Invasive and Non-Invasive Techniques* (2005), which is incorporated by reference in its entirety). The invasive and/or non-invasive techniques may be conducted under angiographic guidance, if desired. By evaluating endothelial function with invasive and/or non-invasive techniques, the results may contribute to the early identification of atherosclerosis in the general population as well as require better control of their lipid profile, C reactive protein, serum glucose, blood pressure, and smoking, since these major and minor risk factors affect endothelial function significantly.

Stabilization Group

In another exemplary embodiment, the physician may suggest that the patient qualifies for an angiogenic-based therapy that may provide for localized stabilization treatments to inhibit, prevent or delay the growth of atherosclerotic plaques. The physician may assess the atherosclerotic plaque composition, function and degree of stenosis to tailor a therapeutically effective angiogenic-based therapy treatment. The angiogenic-based therapy may stabilize the sequences of events that lead to plaque progression, such as the specific cellular and molecular pathways that are responsible for the pathological components of plaque. Such stabilization at the site of the atherosclerotic plaque may inhibit, prevent or delay the occurrence of plaque at any stage and potentially remove the threat of thromboembolic phenomena and/or other plaque complications for potential coronary intervention with stenting, balloon angioplasty, bypass surgery, etc.

The atherosclerotic composition, function and degree of stenosis can be an important determinant of future acute cardiovascular syndromes of unstable angina, MIs and sudden death and/or potential coronary interventions. Although, plaque that is present at any stage may be dangerous, but a plaque that is unstable or vulnerable has emerged as being an important stage for the development of a thrombus because such plaques can be rupture-prone and highly thrombogenic after disruption.

Figure 42A:
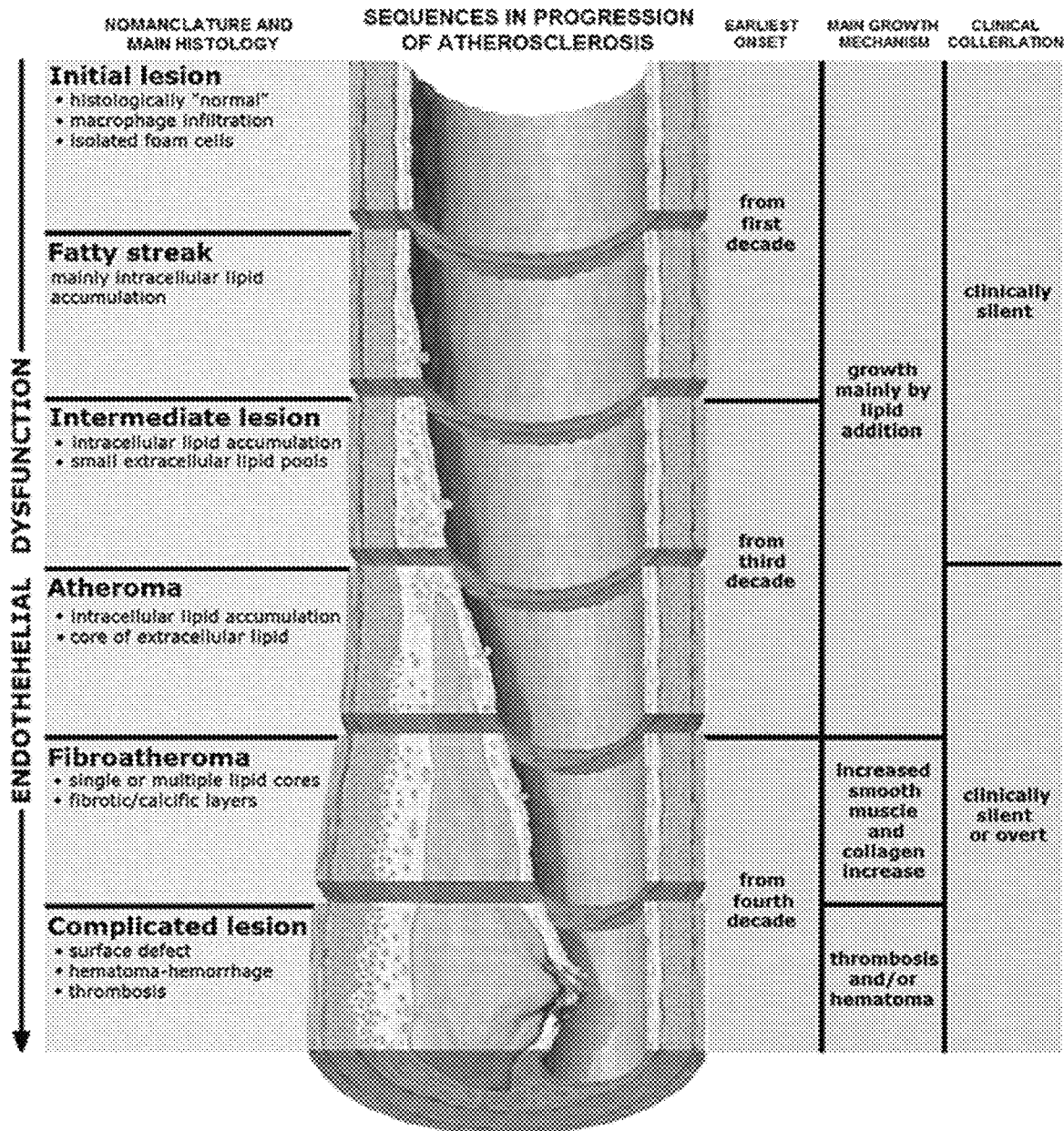
FIGS. 42A and 42B depict various exemplary stages of atherosclerotic progression and subcategories of vulnerable atherosclerotic plaque.

Atherosclerotic plaque is a dynamic process that can progress from a stable atherosclerotic plaque to an unstable and potentially life-threatening atherothromobotic lesion when exposed to continued various noxious stimuli (i.e., major and minor risk factors). Atherosclerotic plaque has been classified into six stages of progression, such as shown in FIG. 42A.

Figure 42B:
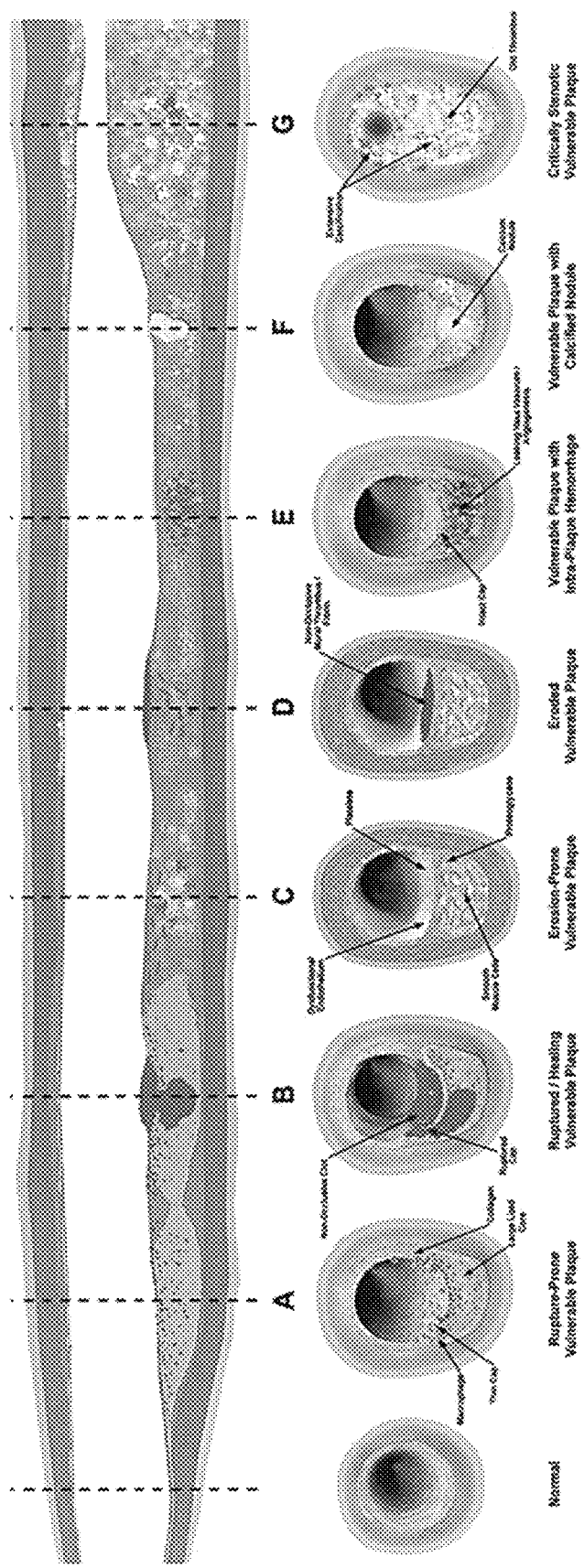

Type I plaque contains atherogenic lipoproteins and infiltrates mononuclear leukocytes. The intima makes adaptive changes such as thickening. This is seen in most people at birth. Type II has layers of macrophages or foam cells with SMC infiltration from the media into the intima. The gross lesion is designated as a fatty streak and is unique to the disease. Type III is an intermediary stage between types II and IV, with scattered coarse lipid granules or particles that disrupt the integrity of the SMC. Type IV lesions are characterized by typical atheromas containing a large extracellular lipid core and the abluminally growing atherosclerotic lesion. Type V lesions have atheromas with large extracellular lipid cores and the developing fibrous caps. There is an increase in the collagen and (more often) SMC content. Type V lesions are further classified into the Vb and Vc subtypes. Vb are characterized by largely calcified lesions, whereas the Type Vc contain more fibrous connective tissue, little lipid and no calcium. Type VI lesions have ruptured atherosclerotic plaque with subsequent fissure formation or hematomas in the arterial lumen (hereinafter known as intraplaque hemorrhage). The main pathologic feature of a vulnerable plaque is an intact thin fibrous cap heavily infiltrated by macrophages and intraplaque hemorrhages. In addition, vulnerable plaque may be further classified into seven other subcategories, such as shown in FIG. 42B. Stable plaques, on the other hand, contain mostly collagen (a dense extracellular matrix), proteoglycans, calcium, a thick fibrous cap, contains a smaller lipid pool and/or show fewer inflammatory cells, vasa vasorum in the intima, media and adventitia. Administration of angiogenic based treatments may be performed during any of the six stages discussed herein, stages I through VI, as well as any of the subcategories for vulnerable plaques.

Figure 43A:
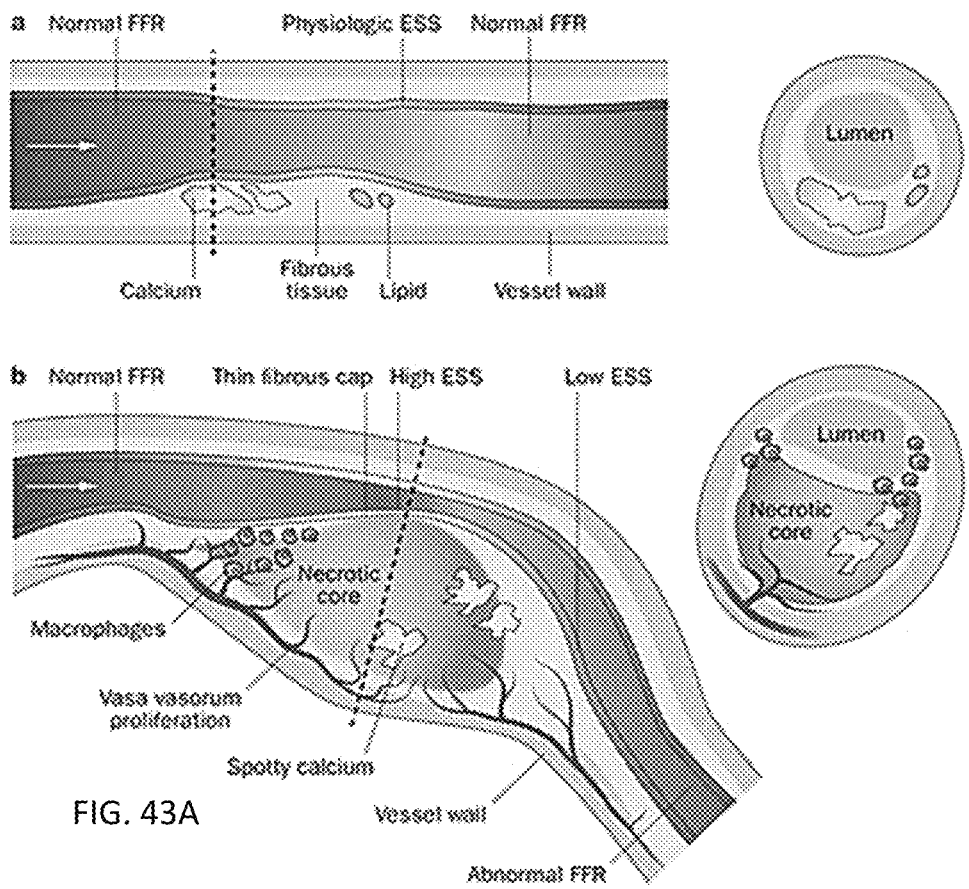
FIGS. 43A and 43B depict examples of plaque progression and increased neovasculature within the intimal coronary vessel wall.
Figure 43B:
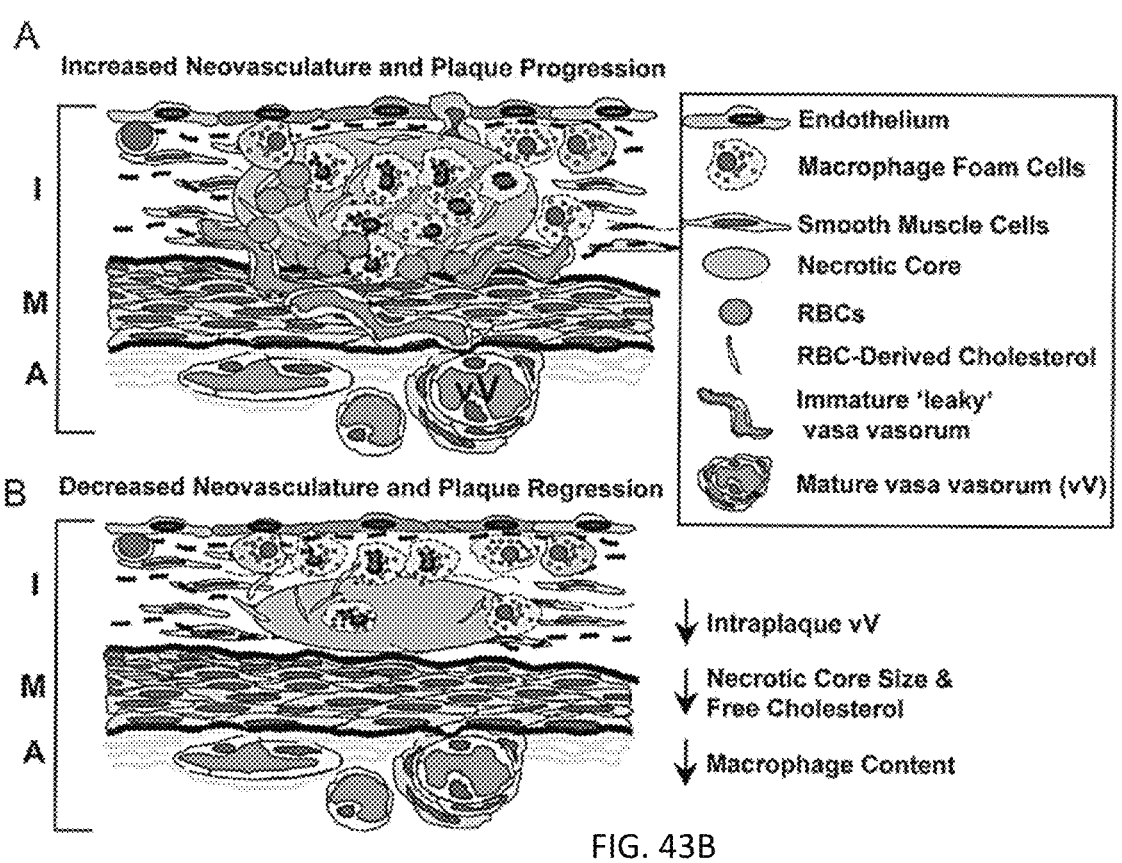

In another embodiment, a physician may select to treat a stage VI atherosclerotic plaque to stabilize the vulnerability of the plaque and prevent thromboembolic phenomenons for future coronary interventions. Vulnerable and/or unstable plaques may be caused by a variety of reasons, but the most significant reason may be due to intraplaque hemorrhages. Intraplaque hemorrhages may be associated with neointimal neovascularization of the adventitial vasa vasorum. The vasa vasorum is a large network of microvasculature that supplies the walls of large blood vessels (i.e., arteries and veins) with sufficient blood supply and nourishment for tunica adventitia and outer parts of tunica media of large vessels. A high concentration of leptin, product of Ob-R gene that promotes angiogenesis, influences inflammatory neomicrovascularization in response to hypoxic conditions. Inflammatory neomicrovascularization causes abnormal and haphazard growth of microvessels that have structural impairments. The structurally impaired microvessels grow and extend into the intima of the plaque causing intraplaque hemorrhaging (see e.g., FIG. 43A). The structural impairment or defects (i.e., which are endothelialized, but rarely possess mural pericytes or smooth muscle cells) of the neointimal microvessels causes red blood cell (RBC) leakiness and spill into the surrounding environment. RBCs and associated macrophage infiltration in response to hemorrhage contribute to necrotic expansion (see e.g., FIG. 43B). It has been observed that structurally impaired neotintimal microvessel density is increased twofold in vulnerable plaques and fourfold in disrupted plaques.

As a result, vulnerable and/or unstable plaques may be comprised of an intact thin fibrous cap heavily infiltrated by macrophages and intraplaque hemorrhages due to structurally impaired neointimal microvessels. Plaque disruption occurs most frequently where the fibrous cap is thinnest, and weakest. Vulnerability to rupture depends on (1) size and consistency of the atheromatous/necotic core, (2) thickness and collagen content of the fibrous cap covering the core, (3) inflammation within the cap, and (4) cap "fatigue." Therefore, targeted correction of structurally impaired neointimal microvessels, inhibition of structurally impaired neointimal microvessels and/or thickening of the fibrous cap may constitute a valuable therapeutic approach toward plaque stabilization of a stage VI plaque and minimizing risk of thrombosis.

The physician may desirably identify the localized plaque composition, function and degree of stenosis to characterize the plaque morphology and recommend stabilization treatments. Then, the physician may administer a localized therapeutically effective angiogenic-based therapy to at least one atherosclerotic plaque and/or adjacent to an atherosclerotic plaque in a coronary artery or coronary microvasculature to (1) prevent and/or delaying the progression of atherosclerosis; and/or (2) stabilize unstable and/or vulnerable plaque from disruption and causing acute coronary syndromes by preventing the growth of structurally impaired neointimal microvessels, inhibiting or removing the growth of structurally impaired neointimal microvessels, and/or thickening the fibrous cap.

The angiogenic-based therapy can activate the mitogenic, chemoattractant and mediation of cellular differentiation for treatments. For example, to prevent and/or delay the progression of atherosclerotic plaque, the dysfunctional endothelial cells (ECs) should be returned to basal homeostasis and dead cells need to be replaced. The angiogenic-based therapy may be able to encourage endothelial cell replacement by circulating endothelial progenitor cells, local endothelial cell proliferation and migration, and/or abrogation of endothelial apoptosis. Alternatively, to stabilize unstable and/or vulnerable plaque from disruption, the fibrous cap should be thickened by smooth muscle cell (SMC) proliferation and/or migration, replacement of new vasa vasorum microvascular network from the structurally impaired microvascular network, decrease the size and consistency of the atheromatous/necotic core, and/or decrease inflammation within the fibrous cap. The increased expression of the angiogenic-based therapy may be able to regulate the healing response, proliferation and/or migration of SMCs along an endothelial to medial gradient by localized and directed application.

Various imaging modalities as discussed herein may be used to characterize all stages of plaque, as well as unstable or vulnerable plaques. Intravascular ultrasound, angioscopy, magnetic resonance imaging, spectroscopy, nuclear imaging, computed tomography and scintigraphy be useful in vivo identification and characterization of coronary plaques. Moreover, the physician may also assess the degree of stenosis and/or common regions where such vulnerable or unstable plaque exists. Overall, nearly 75% of lesions showed <75% cross-sectional luminal-narrowing or (<50% diameter stenosis) of plaques considered vulnerable or unstable. In addition, the specific location within the coronary tree may be an indicator of vulnerable or unstable plaques. Approximately 50% of the TCFAs occur in the proximal or middle portions of the major coronary arteries (left anterior descending>left circumflex>right coronary artery), with another one third in the midportion and the remaining few in distal segments.

Angiogenic-Based Therapy

Treatment Composition

The physician may desirably use an angiogenic-based therapy to treat at-risk and/or overt IHD patients. Such angiogenic-based therapy may comprise a therapeutically effective concentration of a growth factor, stimulating protein, and/or transcription factor that stimulates angiogenesis, as well as any carrier solutions and/or implants, such as described in U.S. Pat. No. 8,983,570 (hereinafter known as the '570 patent) and U.S. Pat. No. 7,252,818 (hereinafter known as the '818 patent), both of which are herein incorporated by reference in their entireties.

In one embodiment, the angiogenic-based therapy may include angiogenic activators and/or angiogenic inhibitors. Examples of angiogenic activators include fibroblast growth factors, vascular endothelial growth factors, vascular endothelial growth factor receptors, neuropilin-1, angiopoietins, such as Ang1, tyrosine kinases (Tie), such as Tie2, transforming growth factor-$\beta 1$, transforming growth factor-$\beta 1$ receptors, endoglins, chemokines, hepatocyte growth factors, monocytechemoattractant protein-1 integrins, such as $\alpha_v\beta_3$, $\alpha_v\beta_5$, $\alpha_5\beta_1$, VE-cahedrin, platelet-endothelial cell-adhesion molecule, ephrins, plasminogen activators, matrix metalloproteinases, cyclo-oxygenase-2, and/or any combination thereof. Examples of angiogenesis inhibitors include vascular endothelial growth factor receptor-1, neuropilin-1, angiopoietins, such as Ang2, angiostatin and related plasminogen kringles, endostatin (collagen XVIII fragement), vasostatin, calreticulin, platelet factor-4, matrix metalloproteinase inhibitors, prothrombin kringle-2, antithrombin III fragment, maspin, canstatin, proliferin-related proteins, restins and/or any combination thereof.

In another embodiment, a physician may desirably select an angiogenic activator, such as Fibroblast Growth Factor (FGF-1) to be used as part of the angiogenic-based therapy. FGF-1 (also known as FGF-1) belongs to a larger family of heparin binding growth factors that is now generally referred to as fibroblast growth factors (FGFs). There are at least 22 known members of the FGF family—from FGF-1 through FGF-22. FGF family members possess broad mitogenic, chemoattractant, mediator of cell differentiation and cell survival activities, and are involved in a variety of biological processes, including embryonic development, cell growth, morphogenesis, tissue repair, tumor growth and invasion. This protein functions as a modifier of endothelial cell, fibroblasts, vascular endothelial cells, chondrocytes, keratinocytes, melanocytes, glial cells and smooth muscle cell migration and proliferation, as well as an angiogenic factor. In addition, the FGF-1 and its family members may promote the survival and differentiation of post-mitotic neurons derived from cerebral cortex, hippocampus, cerebellum, retina, spinal cord, and/or ciliary ganglion. Moreover, any of the plurality of FGF-1 types may be used such as purified, acidic, wild, basic and/or any combination thereof. The physician may administer FGF-1, and/or any of the known FGF family members based on the selected or matched therapy and type of treatment for the patient.

In another embodiment, a deduced amino acid sequence form of FGF-1 may be used as part of the angiogenic-based therapy. FGF-1 consists of approximately 155 amino acid forms, FGF-1-1 through FGF-1-155. For example, the physician may administer FGF-1-140, FGF-1-141 FGF-1-154 and/or FGF-1-155 amino acid form because they may appear to have similar, substantially similar and/or identical biological properties when tested in reproducible bioassays. The specific amino acid form that would be selected may be matched to the patient and/or type of treatment necessary.

As used herein, the terms "treating," "treatment," "therapeutic," or "therapy" do not necessarily mean total cure or abolition of the disease or condition. Any alleviation of any undesired signs or symptoms of a disease or condition, to any extent, can be considered treatment and/or therapy. In addition, asymptomatic degenerative heart or vessel disease may be the focus of treatment utilizing angiogenesis. Furthermore, treatment may include acts that may worsen the patient's overall feeling of well-being or appearance.

The term "therapeutically effective amount" is used to indicate an amount of an active compound, or pharmaceutical agent, that elicits the biological or medicinal response indicated. This response may occur in a tissue, system, animal or human and includes alleviation of the symptoms of the disease being treated.

Dosage Administration

In one exemplary embodiment, the dosage administration of the angiogenic-based therapy may be chosen by an individual physician in view of a patient's condition and/or offered in standard dosages based on effective treatments over-time. The physician may use a variety of conditions or clinical indicators, including the type of angiogenic-based compound selected, the severity of IHD, the risk of the manifestation of IHD, symptomatic or non-symptomatic status of the patient, the type of treatment considered for the patient, route of administration, weight and/or any combination thereof.

In another embodiment, the dosage administration of the angiogenic-based therapy may be selected by calculating and adjusting to each patient's blood chemistry a desired dosage to maintain the modulating effects. One example may include adjusting the dosage to the patient's individual plasma levels or minimal effective concentration (MEC). The MEC will typically vary for each angiogenic-based therapy, as well as depend on the patient's condition, clinical indicators and route of administration. If desired, HPLC (high-performance liquid chromatography) assays or bioassays can be used to determine plasma concentrations.

In various embodiments, an angiogenic based therapy can be administered by a discreet dosage and/or over one or more intervals of time. For example, the dosage may be a single one or a series of two or more doses given over the course of one or more days, as is warranted by the patient's condition. Alternatively, the dosage may be a continuous infusion, preferably at a dose of each active ingredient up to approximately 400 ug per day, such as stated in the '570 patent. Thus, the total daily dosage may typically be in the range of approximately 0.1 to approximately 400 ug. Where no human dosage is established, a suitable human dosage can be inferred from $ED_{50}$ or $ID_{50}$ values, or other appropriate values derived from in vitro or in vivo studies, as qualified by toxicity studies and efficacy studies in animals.

In another embodiment, the dosage may be an escalating dosage administered over an interval of time. An escalating dose may be provided at follow-up visits for a variety of reasons, including limited angiogenic effect observed, worsening cardiac function, subsequent or repeat MI, weight change, effect on half-life (see e.g., FIGS. 13A and 13B), and/or any combination thereof.

In another embodiment, the escalation, single, series and/or continuous therapy may be delivered via topical or parenteral action on-site in a clinical setting or off-site in a patient's own domestic setting. Such parenteral routes may include intravenous, intramuscular, subcutaneous, intra-arterial, and/or any combination thereof. More specifically, introduction of the angiogenic-based therapy may be delivered via automatic pump distribution (internal or external pump) and/or delayed or extended release implant (for sustained delivery of the angiogenic-based therapy). Alternatively, such topical routes may include transdermal/transmuscular and/or pure topical on the cardiac tissue.

Various Access Techniques

The angiogenic-based therapy may be delivered to a targeted, localized region of interest within a patient's heart using a various access techniques and a plurality of deployment devices.

In one embodiment, the physician may decide to administer angiogenic-based therapy via invasive access techniques. Such invasive techniques may include full conventional open heart surgery with a heart-lung bypass and/or thoracotomy. Invasive access techniques allow the physician to have complete direct access to the heart while the patient is "on-pump" (i.e., on a heart-lung bypass machine to keep the heart pumping and circulating blood to the body) or "off-pump" (i.e., the heart-lung bypass machine is not used) on a heart-lung bypass machine. This will allow full visualization of the targeted, localized region of interest for treatment. Alternatively, the physician may desirably administer angiogenic-based therapy via thoracotomy, where such common approaches include posterolateral, anterolateral, bilateral anterolateral thoracotomy and/or any combination thereof. Furthermore, the physician may desirably administer angiogenic-based therapy in conjunction with other treatments, such as a coronary bypass procedure, pulmonary resection, etc.

In another embodiment, the physician may decide to administer angiogenic-based therapy via minimally invasive access techniques. Such minimally invasive techniques may include a mini-thoracotomy, MIDCABG, robotically assisted techniques, videoscopic and/or endoscopic surgery, and/or any surgery intending to minimize incision length, decrease body trauma and/or reduce recovery time. Minimally invasive procedures may also be described as "limited access," "keyhole," and/or "port access." Having angiogenic-based therapy administered via minimally invasive access techniques allows the physician to use special, modified or improved instruments to obtain access and reach the region of interest. Furthermore, the physician may desirably administer angiogenic-based therapy in conjunction with other treatments, such as an atrial septal defect closure, patent foramen ovale closure, ablative maze procedures for atrial fibrillation, etc.

In another embodiment, the physician may decide to administer angiogenic-based therapy via percutaneous access techniques. For example, percutaneous access techniques may include transfemoral vein approach, transfemoral artery approach, carotid approach, right internal jugular vein approach, transapical approach, subclavian artery approach, auxiliary artery approach, coronary sinus approach, ascending aorta approach, and/or any surgery that may include a puncture of the skin to obtain access to a patient's targeted blood vessel. Furthermore, the physician may desirably administer angiogenic-based therapy in conjunction with other treatments, such as carotid artery stenting, ventricular assist device placement, coronary artery angioplasty, etc. Furthermore, at least one of the various invasive, minimally invasive, percutaneous technique and/or any combinations thereof may be used.

Deployment Device Systems (DDS)

In another embodiment, patients with IHD may be treated with a plurality of deployment device systems that administer the angiogenic-based therapy as described herein. The deployment device system (DDS) may comprise at least one catheter, a steerable catheter tip, a steering mechanism, an injection catheter tip, and injection mechanism, an image mapping mechanism, a deployment mechanism, a retrieval mechanism, an implant, and/or any combination thereof. Furthermore, the DDS may include a standardized sized catheter that accommodates the physician selected techniques as described herein and/or it may be a modular catheter that can be modified for patient size, function and/or access technique. Also, the delivery device system may generate a continuous release, intermittent release, manual release, and/or automatic release of the angiogenic-based therapy as described herein.

In another embodiment, the physician may desirably inject a solution and/or liquid form of angiogenic-based therapy. Such solution and/or liquid form may be available in an injectable viscosity for a topical or parental application. The solution and/or liquid form of angiogenic-based therapy may be manufactured in a pre-loaded container that may require immediate placement in the injection mechanism of the DDS. The injection mechanism of the DDS may contain an automatic opening feature and/or refrigerant feature to maintain sterility and/or half-life of the angiogenic-based therapy. Furthermore, the injection mechanism, particularly, the injection feature may require preoperative wall thickness measurements on the extension length to avoid perforations and/or lacerations of the heart wall or vessels. Alternatively, the solution and/or liquid form of the angiogenic-based therapy may be prepared in the OR, where the mixture will typically be immediately poured into the injection mechanism of the DDS. The DDS injection mechanism may have injection speed dials or injection-release selections for either the prepared or pre-loaded container.

Figure 20:
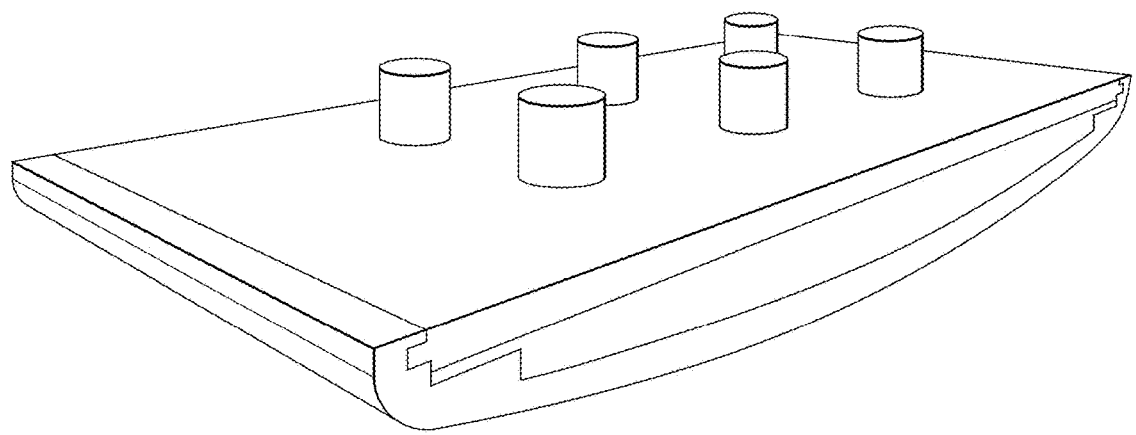
FIGS. 20 through 22 depict perspective views of one embodiment of an implant cartridge system.
Figure 21:
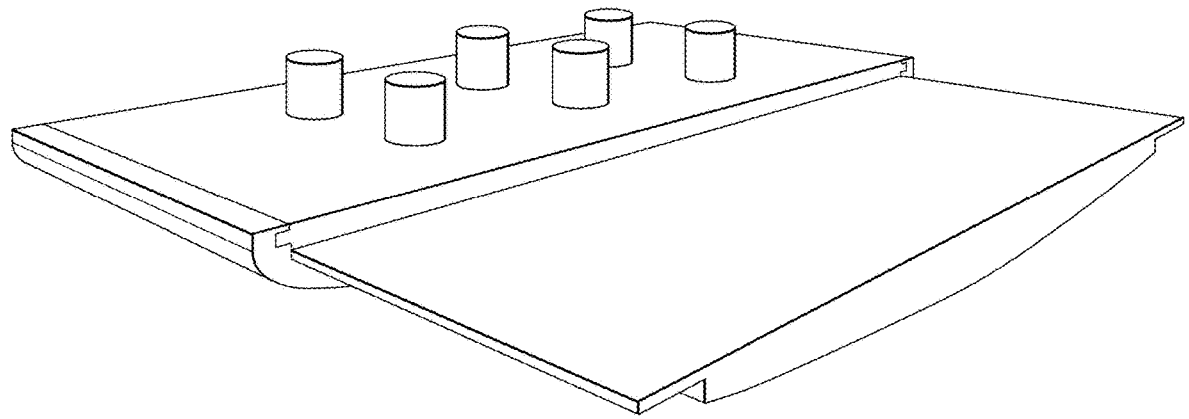

In another embodiment, the physician may desirably deploy an implant with an aqueous solution and/or liquid form of angiogenic-based therapy using the DDS or via direct access during surgery. The implant may serve as a cartridge or container that holds a solution and/or liquid form of the angiogenic-based therapy. FIGS. 20 and 21 depict isometric views 200 of one embodiment of an implant cartridge 202 that may be deployed using the DDS onto and/or into at least one cardiac tissue layer. The implant cartridge 202 may comprise a cartridge housing 204, a cartridge foundation 206, injection needles 208, a treatment cartridge and/or the angiogenic-based therapy 210.

Figure 22:
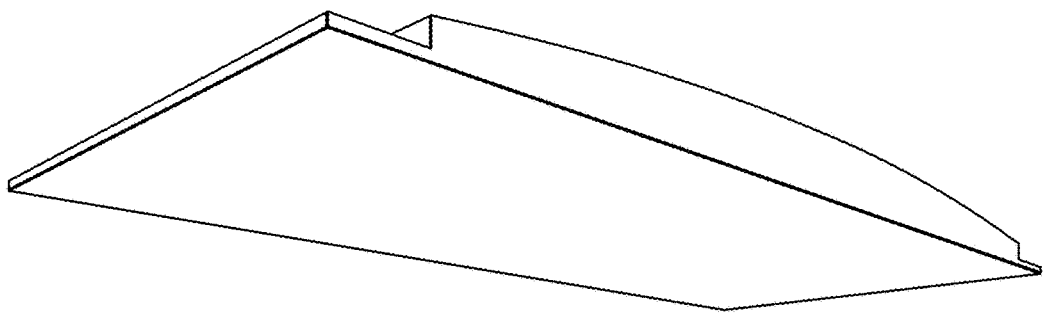

The implant cartridge 202 may include a treatment cartridge 210 that is integrated or modular (i.e., connectedly removable), such as shown in FIG. 22. The treatment cartridge 210 may comprise at least one cavity 212 and at least one boundary layer 214. The at least one cavity 212 may be filled with any desired dose or concentration of the selected angiogenic based therapy. Furthermore, should different doses or concentrations be required, the cavity 212 may have dual or triple cavities (not shown) to accommodate the different angiogenic-based therapy doses or concentrations. In addition, the cavity 212 may be a flexible or rigid biocompatible material, such as polymers, foamed polymers, rubber, cellulose wood fibers and/or metal. For example, the at least one cavity may be made of a flexible rubber that may act as a bladder. If the treatment cartridge 210 cavity 212 was made of a flexible rubber and it was implanted in the myocardium, the contracting muscle might act as a downward or axial force on the flexible rubber (i.e., bladder) and expel and/or inject the angiogenic-based therapy until the cavity 212 is empty. The treatment cartridge 210 may be removed at a subsequent treatment visit, such as a follow-up visit or any other procedure that may access the treatment cartridge 210, or the cartridge may biodegrade.

Figure 23A:
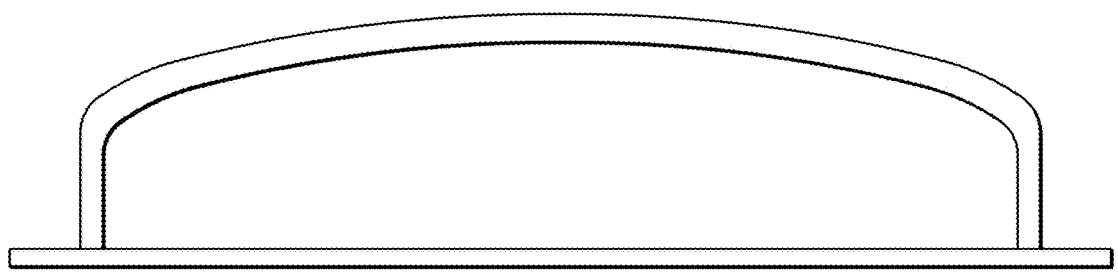
FIGS. 23A and 23B depict a front view of one embodiment of an implant cartridge.
Figure 23B:
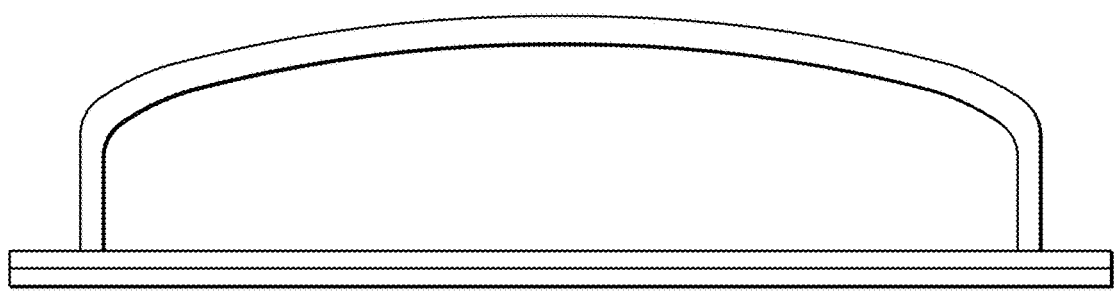

The at least one cavity 212 may be sealed with the at least one layer 214, such as shown in FIG. 23A. The at least one layer 214 may have an inner surface 216 that contacts the angiogenic-based therapy and an outer surface 218 that may contact the tissue and/or another layer. The at least one layer 214 may be a flexible or rigid biocompatible material, such as a polymer, foamed polymer, rubber, cellulose wood fibers and/or metal. Furthermore, the biocompatible materials may be porous, where the biocompatible material can absorb liquid and/or liquid based solutions, as well as moisten or deliver liquids or liquid-based solutions. In addition, the at least one layer 214 may include an adhesive or adhering surface 220, such as shown in FIG. 23B, which may include a peel cover (not shown) on the outer surface 218 to prevent premature sticking and/or maintain a desired level of sterility. For example, if the at least one layer 214 was manufactured from a foamed polymer (i.e., to have a sponge-like quality), the angiogenic-based therapy may saturate the foamed polymer to provide an initial/starting foundation or interaction with the at least one cardiac tissue.

Figure 24:
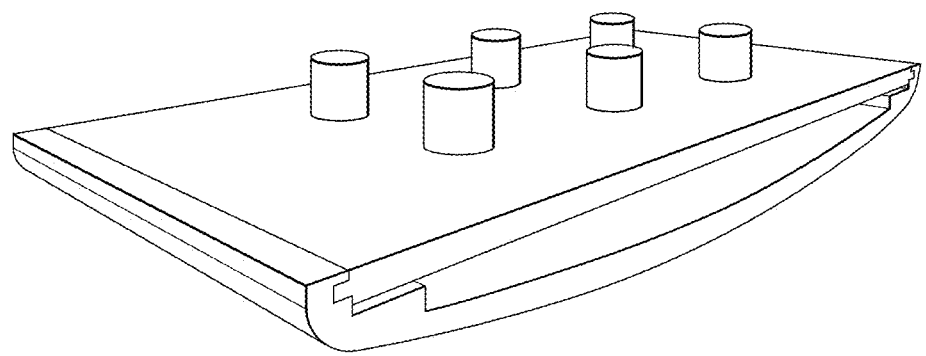
FIG. 24 depicts a perspective view of one embodiment of an implant cartridge housing.
Figure 25A:
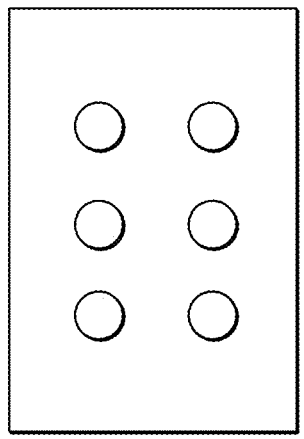
FIGS. 25A and 25B depict a bottom view of one embodiment of an implant cartridge housing.
Figure 25B:
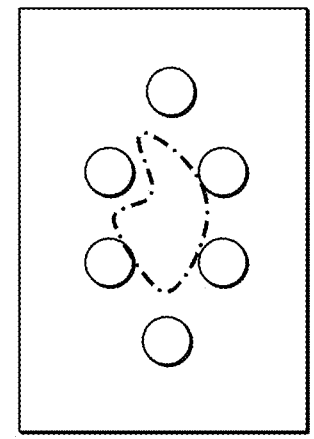
Figure 26A:
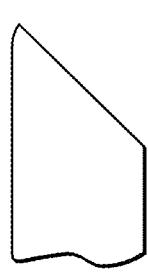
FIGS. 26A through 27B depict side views of embodiments of injection needle tips.
Figure 26B:
Figure 27A:
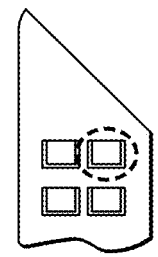
Figure 27B:
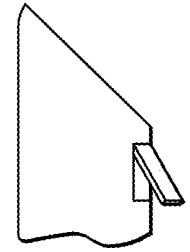

FIG. 24 shows the treatment cartridge 210 may be placed in the cartridge housing 202 which forms opening 222. The cartridge housing 202 may comprise a cartridge housing cover, cartridge housing base 206 and/or injection needles 208. Such injection needles 208 may be integrated within the cartridge housing base 202 and/or connectedly removable. The injection needles 208 may comprise a standard pattern or orientation, such as shown in FIG. 25A, and/or the injection needles 208 may be placed in custom orientation to accommodate the size, shape or perimeter of an MI, such as shown in FIG. 25B (optionally with the needle distribution, size, length and/or shape desirably created using patient image data and/or manufactured via rapid prototyping and/or 3D printing techniques). Desirably, the cartridge housing base 202 with injection needles 208 may be utilized alone without the cartridge housing cover and/or used as a 2nd layer onto the implant cartridge boundary layer, and/or with the cartridge housing cover.

Furthermore, FIGS. 26A-26B and 27A-27B depict various side views of different injection needle 208 embodiments. The injection needle 208 can be may have a through-hole to accommodate the angiogenic-based therapy and may have various configurations. Configurations may include beveled edges and/or tissue holding features. Such tissue holding features may be on the beveled edge, a hook configuration (see FIG. 26B), it may be on the injection needle 208 body, such as a tab 224 (See FIGS. 27A and 27B) that extends outward or radially from the body to prevent movement. Other such holding features may include rough outer surface (not shown), perpendicular extending pins (not shown), and/or any other tissue holding features known in the art.

Alternatively, the physician may decide to deploy the implant cartridge and/or the treatment cartridge via direct access through an invasive or minimally invasive surgery, rather than using a DDS. The physician may predetermine the size, structure and configuration of the implant cartridge and/or the treatment cartridge necessary for the patient during a preoperative planning phase.

In another embodiment, the physician may desirably deploy an implant with a gel, suspension, semi-solid and/or highly viscous form of angiogenic-based therapy using the DDS or via direct access during surgery. The gel, suspension, semi-solid and/or highly viscous angiogenic-based therapy may be available in at least one injectable microcapsule. The microcapsule may include a soluble/dissolvable membrane, film wall or shell ("membrane") that coats or surrounds the gel, suspension, semi-solid and/or highly viscous angiogenic-based therapy, as well as any liquids or gases.

Microencapsulation can be used to slow the release of a drug into the body. Such microencapsulation may decrease dosing frequency, control the rate and/or release of the angiogenic-based therapy dosing, and/or prevent the degradation of the angiogenic-based therapy due to its delayed solubility or dissolvability of the membrane. This embodiment may permit one controlled release dose to substitute for several doses of non-encapsulated drug and also may decrease toxic side effects or improve favorable pharmacokinetics of the angiogenic-based therapy by preventing high initial concentrations in the blood. The microcapsules may deliver a fixed amount of the angiogenic-based therapy per minute or hour during the period of their effectiveness, or at least as long as a solid reservoir or dissolving angiogenic-based therapy is maintained in the microcapsule.

Figure 28A:
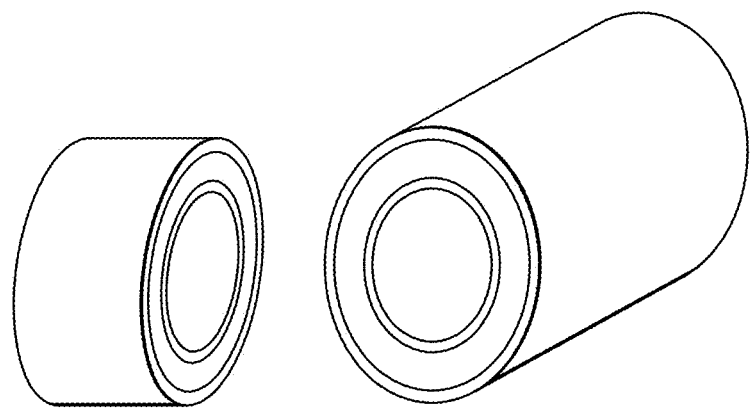
FIGS. 28A and 28B depict perspective and cross-sectional view of one embodiment of a multi-layered microcapsule.
Figure 28B:
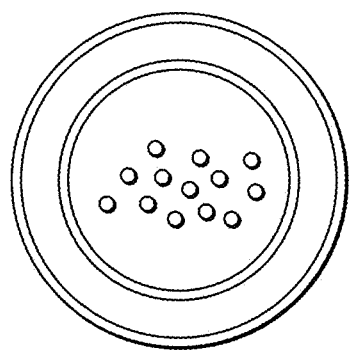

The at least one injectable microcapsules 280 may include a multi-layer microencapsulation or a gel microencapsulation. FIGS. 28A and 28B depict one embodiment of a multi-layer microcapsule 280. The multi-layer microcapsule 280 may include at least two soluble/dissolvable membranes, the inner membrane 282 and the outer membrane 284. The inner membrane can have a core 286 that will be filled with a first therapeutic dosage of the angiogenic-based therapy and the outer membrane 284 can have core 288 that can be filled with a second therapeutic dosage of the angiogenic-based therapy. The first and second therapeutic dosage 286, 288 of the angiogenic based therapy may include the same or different doses and/or concentrations, carriers, etc. Furthermore, the inner membrane 282 and the outer membrane 284 may comprise the same or different materials and/or pore size.

Furthermore, the inner and/or outer membrane may be manufactured using techniques and/or materials known in the art, including the use of ethyl cellulose, polyvinyl alcohol, gelatin, sodium, and/or any combination thereof. The membranes may have various pore sizes to control the rate, the release and/or degradation of the angiogenic-based therapy, where the diameter pore size may range from a few micrometers and a few millimeters.

Figure 29:
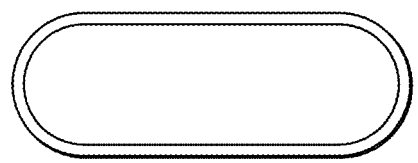
FIG. 29 depicts a side view of one embodiment of a gel microcapsule.

FIGS. 29, 30A and 30B depict various embodiments of a gel microcapsule 290. The gel microcapsule may include a soluble/dissolvable one-piece or multi-piece sealed membrane, where the core 292 desirably includes a therapeutic dose of the angiogenic-based therapy. The physician may load a plurality of gel microcapsules dosages 290a-290d and/or concentrations within the DDS deployment mechanism 294 (see FIG. 31) to inject and/or deploy into at least one cardiac tissue layer. The gel can be a biological or synthetic gel formed from a bioresorbable or bioabsorbable material that has the ability to resorb in a timely fashion in the body environment.

Alternatively, the multi-layer microcapsule 280 (see FIG. 28B) and/or the gel microcapsule 290 (see FIGS. 30A and 30B) may comprise fluorescent, radiopaque and/or paramagnetic microspheres or nanospheres suspended within the angiogenic-based therapy to enable visualization and/or location detection of the treatment. Such microspheres or nanospheres are particles that typically range from 1 to 1000 µm in diameter, where the microspheres or nanospheres may be used as tracers, challenge particles, flow tracing, fluid mechanics, and/or contamination control.

For example, should the microcapsules contain fluorescent and/or radiopaque microspheres or nanospheres, the fluorescent and/or radiopaque microcapsules may emit distinctive colors or brightly irradiate when illuminated by UV light, offer additional sensitivity for observation, and/or provide maximum contrast and/or location detection within the microcirculation or cardiac tissue through the use of various imaging modalities, especially since the angiogenic-based therapy cannot be detected through standard imaging modalities. The fluorescent and/or radiopaque microspheres may be available in a variety of excitation and emission wavelengths, as well as different sphere diameters. These wavelength and size variations can enable complex technical experiments and/or measurements in which the microspheres represent different experimental variables or conditions for separation on the basis of either their excitation or emission spectra, and/or track initial location.

In another example, the microcapsules may contain paramagnetic microspheres or nanospheres, where the paramagnetic microspheres or nanospheres may be charged to enable manipulation with electromagnetic fields. Such charging may be permanent (i.e., it may not dissipate over time), which can assist with tracking or location detection overtime. The paramagnetic microsphere or nanosphere may be a visible marker of the presence of an electromagnetic field (i.e., during magnetic resonance imaging-MRI's), as well as a tracer or carrier particles that may be manipulated with an electromagnetic field (i.e., move the microcapsules to another location or region of interest). Alternatively, the charged microspheres can be used to design the microcapsules to be attracted to or repelled from certain up-regulation of fibrogen/collagen and/or any other negative regulatory cellular processes that form scar tissue and remodel the heart after an MI and/or form atherosclerotic plaque. The paramagnetic microspheres or nanospheres may disperse when diffusing through the microcapsule membrane(s), and/or remain within the microcapsule membrane until the membrane has dissolved.

In addition, the multi-layer and/or the gel microcapsules may be designed with a variety of controlled release features. Such controlled release features may be incorporated or integrated into the design of the microcapsule membrane(s), and the controlled release feature may comprise a stress rupture, melting, dissolving under particular conditions, and/or diffusion through material pore size. A stress or mechanical rupture may occur on the membrane by any cardiac contraction, pressure, force and/or shear stress to break the membrane and release the angiogenic-based therapy within the at least one cardiac layer. Another embodiment may include the melting of the membrane to release the angiogenic-based therapy. The membrane may be designed to melt under normal human blood temperature conditions. In another embodiment, the membrane may dissolve under particular conditions. Such conditions may include dissolving through an enzyme attack, chemical reaction, hydrolysis, and/or slow disintegration. In another embodiment, the controlled release feature may include diffusion through a desired material pore size. The desired pore size can determine the rate in which the angiogenic-based therapy is diffused into the at least one cardiac tissue. A fixed amount of the angiogenic-based therapy is filled in the core of the microcapsule, where the concentration/osmotic pressure/partial pressures difference between the inside and the outside of the capsule and/or membranes enable diffusion until the angiogenic-based therapy is exhausted.

In another embodiment, the multi-layer and/or the gel microcapsules may comprise Scaffold structures. Scaffold structures may be used for anchoring or substantially causing adhesion between the implant and anatomical structures and/or tissue. Suitable scaffold agents are also known to one of skill in the art, and may include hyaluronic acid, collagen gel, alginate gel, gelatin-resorcin-formalin adhesive, mussel-based adhesive, dihydroxyphenylalanine-based adhesive, chitosan, transglutaminase, poly(amino acid)-based adhesive, cellulose-based adhesive, polysaccharide-based adhesive, synthetic acrylate-based adhesives, platelet rich plasma (PRP) gel, platelet poor plasma (PPP) gel, clot of PRP, clot of PPP, Matrigel®, Monostearoyl Glycerol co-Succinate. (MGSA), Monostearoyl Glycerol co Succinate/polyethylene glycol (MGSAIPEG) copolymers, laminin, elastin, proteoglycans, poly (N-isopropylacrylamide), poly (oxyalkylene), a copolymer of poly(ethylene oxide)-poly (propyleneoxide), polyvinyl alcohol and combinations thereof.

In another embodiment, the physician may desirably deploy an implant with one or more polymer fibers that is impregnated with angiogenic-based therapy using the DDS or via direct access during surgery. Using such polymeric fibers may be desirous because it may help localize high concentrations of the angiogenic-based therapy, the fibrous network branching may emulate natural basement membrane systems that originally harbor angiogenic factors in nature, and/or make it possible to retrieve the fibers from the implant site for disposal and/or convenient posttransplant biochemical analysis. The various biocompatible polymer fibers may include many functional characteristics, such as (1) being manufactured with varying pore sizes for optimal impregnation of the angiogenic-based therapy, (2) the fibers may be absorbable or nonabsorbable, (3) fibers may be available as expanded (i.e., where defining the pore size may be eliminated due to a variety of randomly distributed pore sizes), (4) fibers may be constructed by varying the density, texture, modulus and diameter, (5) fibers may be available as a nonwoven, multifilament (angel-hair like-fibers), and/or any combination thereof.

Alternatively, the polymer fibers may be designed with a custom porous matrix, rather than expanded polymers. For example, the porous matrix may have an average pore size of at least approximately 25 micrometers. Preferably, the porous matrix has an average pore size of between approximately 25 micrometers and approximately 110 micrometers. When the average pore size is in this range, it is believed that that porous matrix will also act as a scaffold for in-migrating cells capable of becoming cells stimulatory of angiogenesis in the targeted area. Numerous examples of organic materials that can be used to form the porous matrix are known to one of skill in the art; these include, but are not limited to, collagen, polyamino acids, or gelatin.

The selected fibers may be impregnated with the angiogenic-based therapy and/or an optional extracellular matrix (ECM). For example, a therapeutically effective composition may be developed that includes an ECM (collagens, Type I and IV) with the angiogenic based therapy. The therapeutically effective composition may be bound, impregnated, suspended or attached to the ePTFE (expanded polytetrafluorethylene) fibers. ePTFE may be selected as the polymeric fibers because ePTFE does not produce an intense inflammatory response, it may be easily impregnated or coated with ECM's, the angiogenic-based therapy may retain its biologically active function after impregnation, and/or ePTFE may be engineered to various specifications to meet a multitude of desired configurations.

In another embodiment, the physician may desirably deploy an implant that comprises a stent graft or ring graft (not shown). The stent or ring may be designed with specific and/or standard diameters, lengths and various configurations known in the art to accommodate targeted inner diameter of the coronary arteries or coronary microvasculature. The stent or ring may be encapsulated with a porous polymer, i.e., ePTFE, where the porous polymer can be impregnated, suspended or attached with the angiogenic-based therapy (i.e., drug-eluting stent).

Deployment Procedure

A patient may receive angiogenic-based therapy when they demonstrate evidence of IHD and/or they are "at-risk" of manifesting IHD. Once a patient is diagnosed, the physician can optimize and/or customize their angiogenic-based therapy treatment plan. The procedural steps may include diagnosing a patient with IHD or "at-risk" of manifesting IHD; imaging a region of interest within the coronary vessels and/or the coronary microvasculature; confirming diagnosis and severity of disease and/or the atherosclerotic plaque by conducting quantitative and qualitative analysis of an atherosclerotic plaque, the coronary vessels and/or coronary microvasculature; using the imaging, quantitative and qualitative analysis results to determine the placement within a treatment group; using the imaging, quantitative and qualitative analysis results to create a preoperative plan with customized angiogenic-based therapy access technique and angiogenic-based therapy treatment regimen; administer the angiogenic-based therapy to the localized region of interest that is based on the treatment group and preoperative plan; follow-up with patient to determine the efficacy of the angiogenic-based therapy; optionally adjust the treatment group, the angiogenic-based therapy and/or create a new preoperative plan.

Patient Diagnosis

A patient may be diagnosed with IHD or diagnosed as an "at-risk" patient for manifesting IHD. Such diagnosis may be accomplished through a variety of standard testing or screening tests as known in the art and/or described herein. The physician may evaluate a patient's medical history, family history, risk factors, results from a physical exam, results from diagnostic tests, results from procedures, and/or any combination thereof to obtain a diagnosis.

Confirmation of Patient Diagnosis

A physician may choose to confirm the patient diagnosis visually to facilitate precise quantification of the extent and severity of IHD patients and/or "at-risk" of developing IHD patients. Such visual confirmation may facilitate the physician's selection for the optimal angiogenic-based treatment plan for the patient.

In one embodiment, the physician may decide to utilize supporting image data from SPECT perfusion results for patient diagnosis confirmation. The physician may employ the standard 17 segment model, where cardiac perfusion may be measured under rest and stress. The SPECT image data may be evaluated to determine the segments that reveal or exhibit hypoperfusion (see FIGS. 15A through 16B) after assigning at least one semi-quantitative measure of myocardial perfusion.

Various examples of semi-quantitative measures may be used, including a severity score, a summed rest score (SRS), a summed reversibility score (SDS), a summed stress score, a summed predictor score (SPS), and/or any combination thereof. The severity score may indicate the severity of the lack of perfusion in a specific segment. The severity score may be defined as 0=normal, 1=mildly reduced, 2=moderately reduced, 3=severely reduced; and 4=absent uptake. This may be further calculated into determining the mean severity scores for each treated segment at rest, summed rest score (SRS), and/or at stress, summed stress score (SSS). Alternatively, a measure of reversible myocardial ischemia may be used, which may be a summed reversibility score (SRS). The SRS may be calculated as SSS minus SRS. Ultimately, the physician may consider both the perfusion image data, and/or the various semi-quantitative severity scores that may be greater than demonstrate scores greater than 2, to confirm patient diagnosis and select the patient for angiogenic-based therapy.

In another embodiment, the physician may select to utilize supporting image data from electromechanical mapping results for patient diagnosis confirmation. An electromechanical mapping catheter, like the NOGA Myostar by Biosense Webster, Inc. (Cordis), may be inserted into the ventricle, analyzing end-diastolic and end systolic functions, and/or correcting for the motion of the patient's heart at the region of interest and/or adjacent to the region of interest. The electromechanical map can determine viable versus nonviable regions of the myocardium for potential optimization and/or customization of the preoperative plan. The electromechanical mapping may illustrate the viable and non-viable sections of the myocardium in a 3D color coded model/graphical form (see FIGS. 17A and 17B) and a quantitative segmental map (see FIGS. 18A and 18B). Such graphical and quantitative mapping allows the physician to narrow or focus the treatment within and/or adjacent to the region of interest, as well as understand the trajectory of impaired cardiac tissue for treatment administration.

In another embodiment, the physician may decide to utilize supporting image data from angiographic analysis for patient diagnosis confirmation. The angiographic analysis may be performed using standard procedures known in the art to determine ventricular size, detect abnormalities or blockages in the coronary blood vessels, and/or myocardial vascular bed density at or adjacent to the region of interest. Angiographic analysis may include other imaging modalities such as standard coronary angiograms, computerized tomography (CT) angiography, magnetic resonance (MR) angiography and/or any combination thereof. Also, angiographic analysis may include digital subtraction angiography (DSA) to analyze the distribution of the contrast media in the vascular bed after contrast bolus administration to produce 2D or 3D representations of the vascular beds. The angiographic images obtained from the different angiographic modalities may be used to provide a physician an accurate "map" of the myocardial vessels and perfusion prior for preoperative planning.

In another embodiment, the physician may decide to utilize supporting data from ECG for patient diagnosis confirmation. Using ECG may be performed using standard procedures known in the art to localize the site of ischemia, injury and/or MI. Correlations can be made by scrutinizing the Q waves (ventricular depolarization), ST-segment elevations, and/or T-wave inversions (repolarization of ST-T wave changes) during stress and/or rest for ischemia, injury and/or MI. Specific manifestations of the waves typically depend on whether the lesion is subendocardial or transmural, as well as determine its position.

Figure 33:
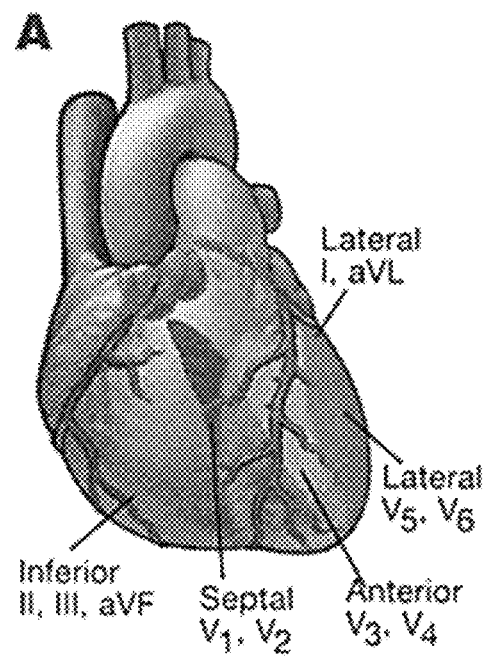
FIG. 33 illustrates an anterior view of the heart and the infarcts related to the 12-lead EKG wires of FIG. 32.
Figure 34A:
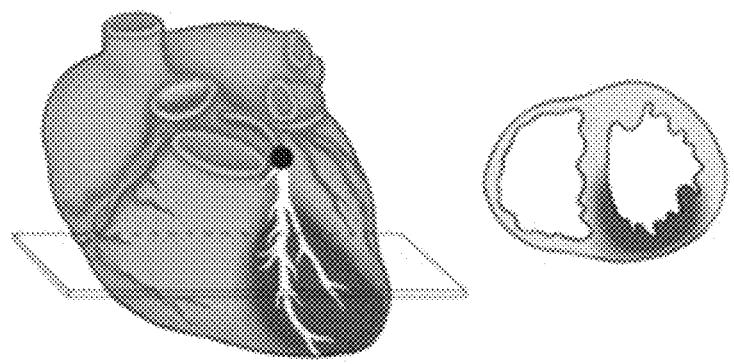
FIGS. 34A through 34C illustrate anterior and top views of the heart and infarcts related to the 12-lead EKG wires of FIG. 32.
Figure 34B:
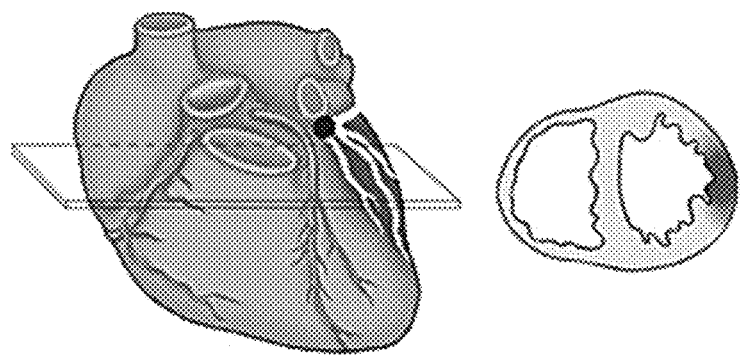
Figure 34C:
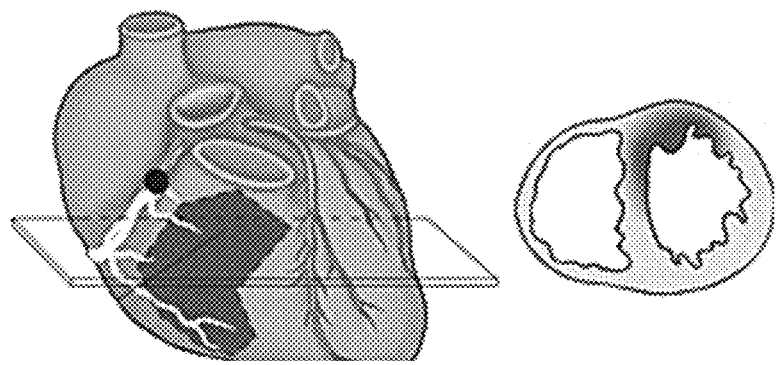

For example, a 12-lead ECG can be used to distinguish ischemia, injury and/or MI's occurring in different regions of the heart by scrutinizing the specific waves, particularly the Q-waves, and ST-T wave changes. The ECG leads cluster around the heart in a horizontal plane and look in from the front (ECG leads V1 to V4) and from the left (ECG leads I, aVL, V5 and V6), and under the surface of the heart (ECG leads II, III, and avF) as shown in FIG. 32. FIG. 33 depicts one embodiment of a heart in the anterior view that localizes the ischemia, injury and/or MI with the corresponding ECG lead. Signs of anterior MI and/or septal MI, the territory supplied by the left anterior descending coronary artery (LAD), are seen in ECG leads V1 to V4 (see FIGS. 33 and 34A). Signs of lateral MI, territory supplied by the left circumflex coronary artery (LC), are seen in leads I, aVL, V5 and V6 (see FIGS. 33 and 34B). Signs of inferior MI, territory supplied by the right coronary artery (RCA), are seen in leads II, III, and aVF (see FIGS. 33 and 34C). Signs of posterior MI on a 12-lead ECG uncharacteristic wave changes (i.e., the ST-T wave changes and Q waves). Since V1 and V2 are attached to the patient's front, they will record changes reciprocal to changes seen from the back, which are ST depression and tall R waves. These uncharacteristic signs make the diagnosis of posterior MI difficult without heightened vigilance.

Alternatively, the same wave manifestations, Q-waves and ST-T wave changes may also be used to determine whether the MI is subendoardial or transmural. For example, the ECG sign of subendocardial ischemia (ischemia that spreads from the endocardium to a portion of the myocardium) may be illustrated in a ST segment depression. The ST segment depressions seen in subendocardial ischemia or MI may also take on different patterns, such as horizontal depression, down-sloping depression and/or up-sloping depression. If the physician is attempting to find a transmural MI (ischemia that spreads from the endocardium to the epicardium), the ECG data may illustrate an ST segment elevation. The ST segment elevation may also take on different patterns, including sloping upward, horizontal and/or dome-shaped. Such understanding of the Q waves (ventricular depolarization), ST-segment elevations, and/or T-wave inversions (repolarization of ST-T wave changes) during stress and/or rest can assist the physician develop a preoperative plan.

In another embodiment, the physician may collect various quantitative measurements to assist with the confirmation of the diagnosis. Such quantitative measurements may include Timi Frame Count (TFC), Myocardial Blush Grade (MBG), and the other microvascular intracoronary measurements (see FIGS. 37A and 37B) blood flow velocity (APV, average peak velocity), flow patterns (i.e., DT—diastolic deceleration time or system flow reversal), volumetric blood flow, vasoreactivity, coronary flow reserve, fractional flow reserve, index of microvascular resistance (IMR) and/or any combination thereof.

Developing a Preoperative Plan

A physician may develop a preoperative plan after the physician finalizes the selection of a patient by (1) evaluating the patients' medical history, family history, risk factors, results from a physical exam, results from diagnostic tests, results from procedures, and (2) confirming the diagnosis with the various supporting data to confirm the diagnosis. Such preoperative plan may include customized angiogenic-based therapy treatment regimen and/or standard or customized angiogenic-based therapy access technique.

In one embodiment, the angiogenic-based therapy treatment regimen comprises placement of the patient into one or more types of angiogenic-based therapy treatment group(s), selection of a dosing agent, identification of a type of deployment catheter, identification of the targeted anatomy and treatment plan and/or any combination thereof. For example, a physician may better understand the etiology, the progression rate, the patient symptoms after the physician finalized the selection of a patient by (1) evaluating the patients' medical history, family history, risk factors, results from a physical exam, results from diagnostic tests, results from procedures, and (2) confirming the diagnosis with the various supporting data to confirm the diagnosis.

Armed with the collective information, the physician may proceed to place the patient in any of the type of treatment groups as described herein. Such types of angiogenic-based therapy treatments may seek to: (1) revascularize cardiac tissue; (2) repair and/or regenerate cardiac tissue; (3) regulate localized cell growth, migration, differentiation, and/or survival; (4) prophylactically treat cardiac tissue to prevent manifestation of IHD; (5) stabilize atherosclerotic plaques.

Once a patient has been selected into one or more of the angiogenic-based therapy treatment groups, the physician may appropriately select the dosing agent. The dosing agent may include the dose concentration, dose amount, the dose administration, an optional dose delivery method and/or any combination thereof.

Angiogenic-Based Therapy Treatment Regimen

In one embodiment, the physician may select the dose concentration and/or the dose amount of the angiogenic-based therapy based on the patient's toxicity level, by the distribution phase (i.e., by retained fraction of the concentration or retained volume of distribution) or slow elimination phase or the rapid elimination phase and/or by the time of MI morphological changes.

Figure 35:
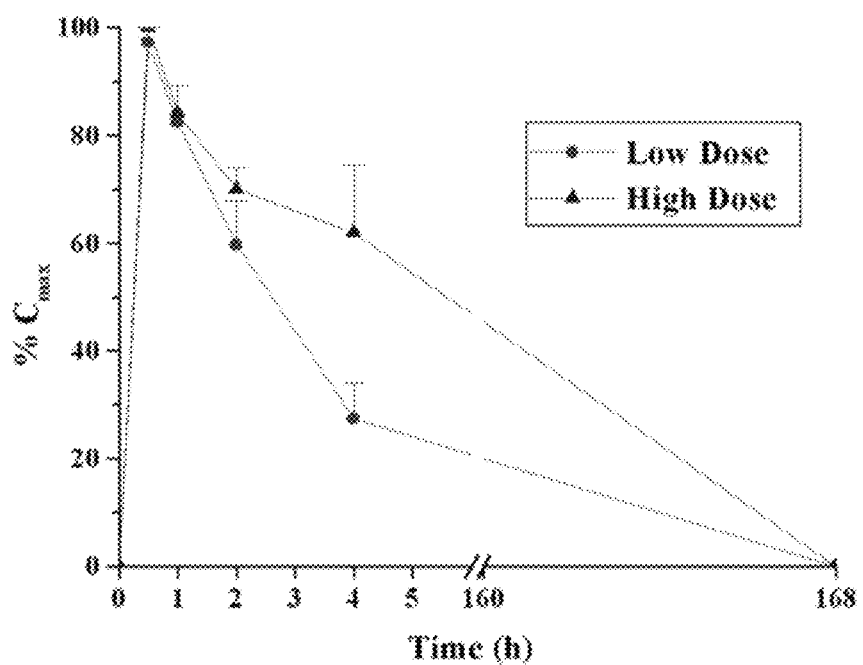
FIG. 35 depicts a graph that plots plasma blood concentration of an exemplary angiogenic-based therapy over time.

FIG. 35 illustrates one embodiment of graph that expresses the plasma blood concentrations (% $C_{max}$) of an administered low dose and a high dose of the angiogenic-based therapy over time. The graph describes that the high dose and the low dose both may be administered in the same loading dose, where the blood concentration at the bolus loading dose is expressed as 100% $C_{max}$, where the amount corresponds to the amount of the angiogenic-based therapy directly after injection. The volume of distribution of the drug can be determined during the distribution phase. The higher dose exhibits less of a "first-pass" effect during the distribution phase. The "first-pass" effect is the fraction of the loading dose that is lost during absorption, leaving the retained fraction of the concentration in the blood.

The volume of distribution is useful and/or essential in estimating the dose concentration and/or dose amount required to achieve a given plasma concentration for a therapeutically effective amount of drug in the body. The variation of volume of distribution mainly affects the peak plasma concentration of the drug. The drug dosage concentration and/or dosage amount should be adapted to the volume of distribution of the angiogenic-based therapy to each patient and/or their treatment type. For example, volume of distribution may vary with a patient's height, weight and age. The most important causes of variation of the volume of distribution are accumulation of fat, such as for obese patients, or accumulation of fluids, such as ascites, edema or pleural effusion. As the proportion of each body compartment varies with a patient's height, weight and age, the angiogenic-based therapy dosage concentration and/or dose amount may be adjusted to maintain the desired plasma concentration within the blood. Several blood tests measuring plasma concentrations may be obtained anywhere from 0 hours (immediately after injection) up to 25 hours, where the interval of the blood tests may occur in 15 min, 30 min or 1 hour increments.

In the figure depicted, the high dose at 2 hours (70% Cmax) and 4 hours (60% Cmax) retains higher fraction concentration of the angiogenic-based therapy than compared to the low dose at 2 hours (60% Cmax) and 4 hours (30% Cmax). In addition, the physician may evaluate the rate of elimination by understanding that the high dose rate of drug elimination is slower than the low dose.

Alternatively, the physician may select the dose amount and/or the dose concentration to be based on the slow or rapid elimination phase of the angiogenic-based therapy. During the rapid or slow elimination phases, the decline of the plasma concentration is primarily associated with elimination of the angiogenic-based therapy from the body. From these phases, the elimination half-life (t½) can be estimated from the terminal slope of the plasma concentration time profile. FIGS. 13A and 13B show one embodiment of an angiogenic-based therapy time course graph of the circulating half-life over time at different angiogenic-based therapy concentrations.

In another embodiment, the physician may select the dose amount and/or the dose concentration to be based on the MI morphological changes over time. For example, the physician may optionally select to treat the patient between 3 to 7 days, where the region of interest can focus on the regulation treatment group, where the dose amount and dose concentration is intended to regulate or inhibit the reparative processes, such as decreasing the phagocytosis at the infarct perimeter/border. Such angiogenic-based therapy treatment may assist with the decrease of the total size of the MI affected region. Table 2 details exemplary MI morphological changes from 0 hours to greater than two months.

TABLE 3

MI Morphological Changes

| Time | Gross Features | Light Microscope | Electron Microscope |
|---|---|---|---|
| Reversible Injury | | | |
| 0 to ½ hr | None | None | Relaxation of myofibrils; glycogen loss, mitochondrial swelling |

TABLE 3-continued

MI Morphological Changes

| Time | Gross Features | Light Microscope | Electron Microscope |
|---|---|---|---|
| Irreversible Injury | | | |
| ½ to 4 hr | None | Usually non; variable waviness of fibers at border | Sarcolemmal disruption; mitochondrial amorphous densities |
| 4 to 12 hr | Occasionally dark mottling | Beginning coagulation necrosis; edema; hemorrhage | |
| 12 to 24 hr | Dark mottling | Ongoing coagulation necrosis; pyknosis of nuclei; myocyte hypereosinophiia; marginal contraction of band necrosis; beginning neutrophilic infiltrate | |
| 1-3 days | Mottling with yellow-tan infarct center | Coagulation necrosis, with loss of nuclei and striations; interstitial infiltrate of neutrophils | |
| 3 to 7 days | Hyperemic border; central yellow-tan softening | Beginning disintegration of dead myofibers, with dying neutrophils; early phagocytosis of dead cells by marcophages at infarct border | |
| 7 to 10 days | Maximally yellow-tan and soft with depressed red-tan margins | Well-developed phagocytosis of dead cells; early formation of fibrovascular granulation tissue at margins; | |
| 10 to 14 days | Red-gray depressed infarct borders | Well-established granulation tissue with new blood vessels and collagen deposition | |
| 2 to 8 wks | Gray-white scar, progressive from border toward core of infarct | Increased collagen disposition, with decreased cellularity | |
| Grtr than 2 mos. | Scarring complete | Dense collagenous scar | |

Understanding the dose amount and dose concentration of the angiogenic-based therapy, the physician may desirably select a relevant dosing administration as described herein. Such dosage administration may be based on the severity of the disease, the treatment group type, the type and location of the anatomy of interest, the maintenance of a therapeutic-effective amount of angiogenic-based therapy within the blood plasma concentrations, the symptoms, convenience of the patient, and a variety of other risk factors. Based on this information, the physician may choose to administer the angiogenic-based therapy via an escalation, single, series and/or continuous dosing, such as described herein.

In another embodiment, the physician may optionally administer the angiogenic-based therapy using a standard or custom dosing delivery method. The dosing delivery method can include an aqueous solution and/or an implant as described herein. Such aqueous solution and/or an implant administration may be based on the severity of the disease, the treatment group type, the maintenance of a therapeutic-effective amount of angiogenic-based therapy within the blood plasma concentrations, the symptoms, convenience of the patient, and a variety of other risk factors. Based on this information, the physician may choose to administer the angiogenic-based aqueous solution or implant in a, single, series and/or continuous dosing.

For example, should the patient be selected for prophylactic treatments to prevent the manifestation of the IHD, the patient may receive a single or series dosing of an aqueous angiogenic-based therapy. The aqueous angiogenic-based therapy may be injected in region of interest where non-viable or "at-risk" cardiac tissue was targeted. Alternatively, a patient from the treatment group that may require revascularization and/or repair cardiac may get either an aqueous or implant angiogenic-based therapy due to the severity of IHD. The aqueous or implant angiogenic therapy may be placed in one or more regions of interest for escalating, single, series and/or continuous dosing administration.

Standard or Customized Angiogenic-Based Therapy Access Technique

In another embodiment, the physician may select the type of angiogenic-based therapy deployment catheter and access approach technique. The deployment catheter may contain an injection mechanism that injects aqueous angiogenic-based therapy and/or injects an implant into at least one cardiac tissue layer, atherosclerotic plaque, coronary artery and/or coronary microvasculature. For example, the physician may have diagnosed the patient with IHD with at least one blocked coronary artery, and the patient may be associated with the revascularization treatment group. The image data may reveal that the blocked coronary artery is the left circumflex coronary artery with at least one upper lateral infarct that may have been confirmed by EMM, ECG, 2D or 3D ultrasound, blood tests, etc. The physician can then select an injectable implant, a FGF-1 microcapsule or ePTFE fibers that has controlled release features. The implant may require injection near an area that is adjacent to the MI site understanding that the proximity of the MI is near the mitral valve annulus. The physician may decide that a percutaneous access approach via femoral artery and a transeptal puncture may be the safest and most effective technique to reach the desired targeted region of interest in the left ventricle via treatment through the endocardium. Such physician considerations may include small incision length, increased mobility during implantation and quicker recovery time. In another example, the physician may decide to deploy or inject the microcapsules using a transapical approach via a minithoracotomy for the most effective technique to reach the desired targeted region of interest in the left ventricle. Physician considerations may include injecting and/or deploying using larger sheath diameters, shorter sheath lengths, larger injection needles and/or its direct and straight access. Table 4 highlights some of the potential physician considerations when favoring one access technique over another.

TABLE 4

A Comparison of Transfemoral and Transapical Access Techniques

| Descriptions | Transfemoral (TF) | Transapical (TA) |
| --- | --- | --- |
| Access | Femoral artery | Left ventricular apex |
| Access mode | Retrograde | Antegrade |
| Incision length [cm] | 1-2 | ~5 |
| Distance to aortic valve [cm] | ~70-100 | ~7-10 |
| Wire insertion | Through the aortic arch, retrograde | Through the aortic arch, antegrade |
| Wire positioning | Arbitrary, across iliac vessels and aortic arch, irregularities, slack | Coaxial, straight |
| Valve insertion | Through the aortic arch, retrograde | No touch aorta |
| Valve orientation | Arbitrary | Commissural (anatomical) alignment possible |
| Valve implantation | Some mobility during implantation | Little mobility, stepwise and controlled implantation usually feasible |
| Application system retrieval | Across the aortic arch, relatively long distance | Direct and straight |
| Access closure | Complication rates as high as 10% | Very low complication rate, ~1% |
| Recovery Time | Usually 1-3 days | Usually 3-7 days |
| Sheath Diameters | Smaller diameters-limited by stretching of femoral artery and advancement | Larger sheath diameters |

If desired, a software platform may be provided that makes such considerations available to the physician. The software platform (i.e., available or downloadable via mobile, desktop, laptop and/or tablet) may allow the physician and/or staff to enter in the diagnostic results (including underlying image data), the risk factors, weight, height, demographic characteristics, symptomatic or non-symptomatic characteristics of the patient, the targeted coronary artery and/or the targeted region of interest location to generate the recommended access techniques and/or dosing agent that may be best suited or most advantageous for the angiogenic-based therapy for a specific patient. Furthermore, when the physician selects the recommended or desired access technique, the software platform may provide specific procedural steps and suggested imaging to assist with the execution of the angiogenic-based therapy. The software platform may be updated by the treating physician after the procedure has been completed to provide annotations, corrections, and/or amendments to the procedural steps.

Figure 36:
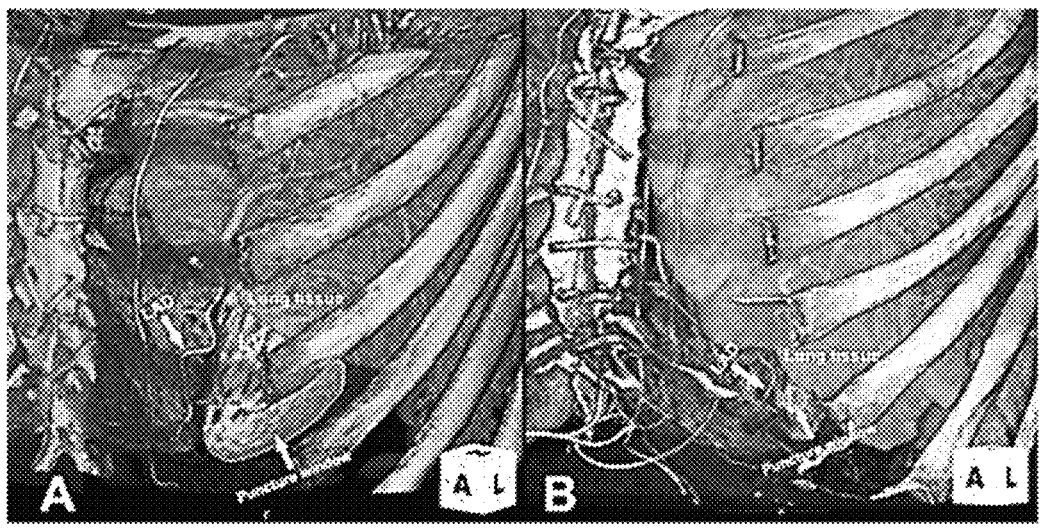
FIG. 36 depicts one embodiment of 3D/4D computed tomographic angiographic (CTA) images highlighting tissue structures.

In another embodiment, the physician's selection of a recommended or desired access technique may prompt the physician to have the patient undergo further imaging to determine a safe puncture window. FIG. 36 illustrates one embodiment of 3D/4D computed tomographic angiographic (CTA) images that highlight an optimal entry point from the chest wall into the LV cavity (i.e., for a mini-thorocotomy). The patient may undergo CTA (i.e., 256-slice CT scanner, Philips, Healthcare, Cleveland, Ohio) by using helical scan mode with retrospective electrocardiogram-gated multiphase reconstruction (16 phases with 6.25% interval increments from RR interval) before the procedure is performed. The image data may be used for 3D/4D volume rendering reconstruction for selecting the optimal entry point from the chest wall into the LV cavity. Other structures may be highlighted, including cardiac apex, papillary muscles, and/or coronary arteries in relation to the chest wall, and the extension of lung tissue over the LV cavity. After the target entry point is selected and measurements obtained, standard markings may be placed on the skin of the patient. The results from the 3D/4D CTA images may reveal poor access due to obstruction of one or more structures, and the physician may decide to change, modify or alter the access technique to avoid complications.

Developing such a preoperative plan may provide the safest, most effective way to inject and/or deploy the aqueous and/or implant angiogenic-based therapy for the patient. Furthermore, it may assist with reducing the overall common complications, such as potential pericardial effusions, laceration of the coronary, pleural, intercostal vessels and/or perforation of the heart causing cardiac tamponade during the selected access technique.

Executing the Preoperative Plan—Treatment Administration

After creating the preoperative plan, the physician can execute the preoperative plan steps. The execution of the preoperative plan may include inserting a steerable catheter into a heart chamber, monitoring the distal end of the catheter tip within the heart on a visual display, contacting at least one layer of cardiac tissue, coronary artery, coronary microvasculature and/or atherosclerotic plaque, creating a channel in the heart tissue or engaging at least one layer of heart tissue and/or administering the angiogenic-based therapy.

In one embodiment, a physician may choose an optimal access technique based on the patient and/or the assigned angiogenic-based therapy treatment group. The physician may employ standard preparations known in the art. The physician may access the heart under direct visualization. The physician may use one or more imaging modalities to assist with advancement to the proper targeted region of interest in the heart. The targeted region of interest may include infarcted tissue, non-infarcted or non-diseased tissue, atherosclerotic plaque, intracoronary vasculature, intracoronary microvasculature, the endocardium (inside the chamber of the left ventricle of the heart) and/or epicardially (outside the heart), and/or combinations thereof. Moreover, the physician may desirably image a targeted region of interest that includes proper functioning coronary arteries and/or microvasculature (no clinical presentation of IHD). This data may be quantitatively and qualitatively analyzed to compare to the diseased regions of interest for a better understanding of the severity of the disease.

Figure 38A:
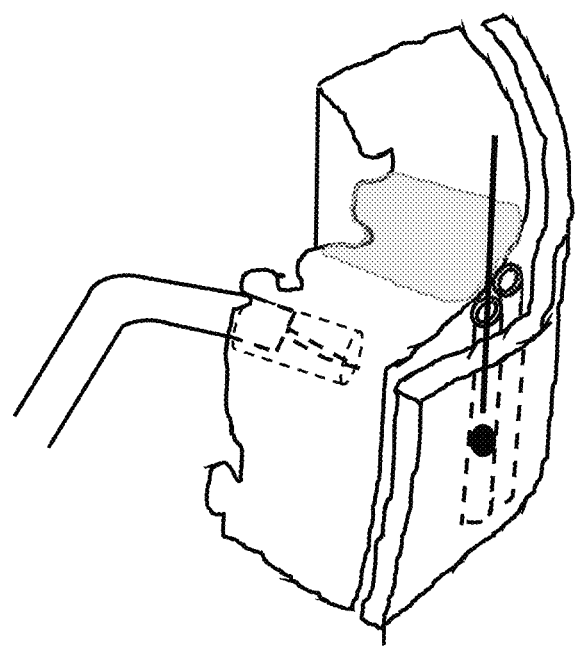
FIGS. 38A through 38D depict a magnified prospective view of endocardial channel creation steps for administration of angiogenic-based therapy.
Figure 38B:
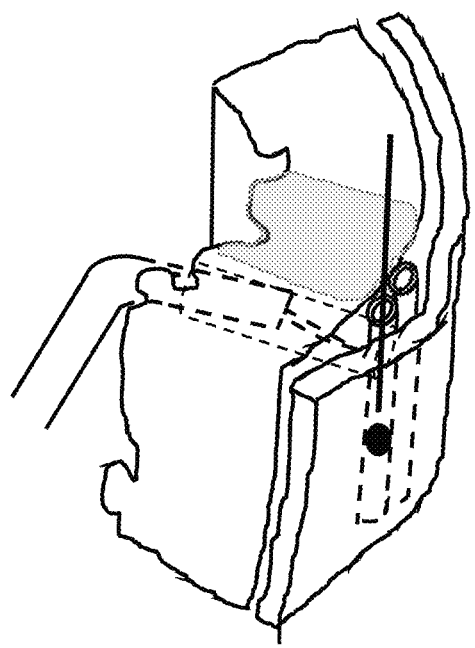

If desired, the various angiogenic-based treatments described herein could be specific combined with artificially designed nanostructures constructed out of nucleic acids such as DNA for targeted delivery, which may further incorporate a DNA-based computing system (i.e., artificial nucleic acid nanodevices) that enables targeted drug delivery to a desired tissue or tissues based upon directly sensing its surrounding environment. Such devices could make use of DNA solely as a structural material and/or a chemical constituent, and would not necessarily seek to use the DNA's biological role as the carrier of genetic information. Nucleic acid logic circuits could potentially be incorporated in a system that releases a therapeutic drug (and/or one of more of a plurality of drugs contained in the delivery vehicle) in response to a stimulus, such as a specific detected mRNA. Alternatively, a DNA "box" of other similar structure could incorporate a controllable "lid" or opening (i.e., synthesized using the DNA origami method) which desirably encapsulates a therapeutic agent in its closed state, and then opens to release the agent in response to a desired external stimulus Example 1—Revascularization Once the physician has reached the targeted region of interest in the heart, the physician may create at least one channel in at least one layer of cardiac tissue. The physician may desirably advance a guide catheter wire (or it may include the IVUS catheter or pressure wire) to the region of interest as a location or reference marker (which may allow a decrease in the volume of contrast used) (see FIG. 38A). Then the physician may press a portion of the catheter against the endocardial surface and/or epicardial surface prior to orienting and/or adjusting the DDS or LVEMM catheter to obtain the trajectory and depth of the one or more channels (see FIG. 38B). The physician may activate the DDS or LVEMM catheter to create the channel(s) and/or perform micro adjustments to achieve the proper depth and trajectory of the channel.

Channel creation may be performed by a plurality of methods, such as thermal ablation technology, chemical ablation and/or any mechanical technologies. Thermal ablation may directly alter the local temperature of the lesion, either with heating or cooling, causing either direct or indirect cell death. Direct or indirect cell death may be done by tissue vaporization, chipping, burning, or other erosive process that is performed via microwave, high-intensity focused ultrasound, laser or radiofrequency ablation and/or cyroblation processes. Alternatively, if the physician chose to employ a chemical ablation, any chemical ablative agents, such as absolute ethanol, typically rely on direct toxicity to produce tissue necrosis. Also, should the physician decide to employ a mechanical technology, the mechanical methods may include a "drill-like" attachment, or a needle-like injection attachment to the DDS and/or LVEMM catheter. The mechanical mechanism may advance independently of the catheter tip or may be advanced by the physician. The channel creation may be conducted under real-time imaging guidance.

Figure 38C:
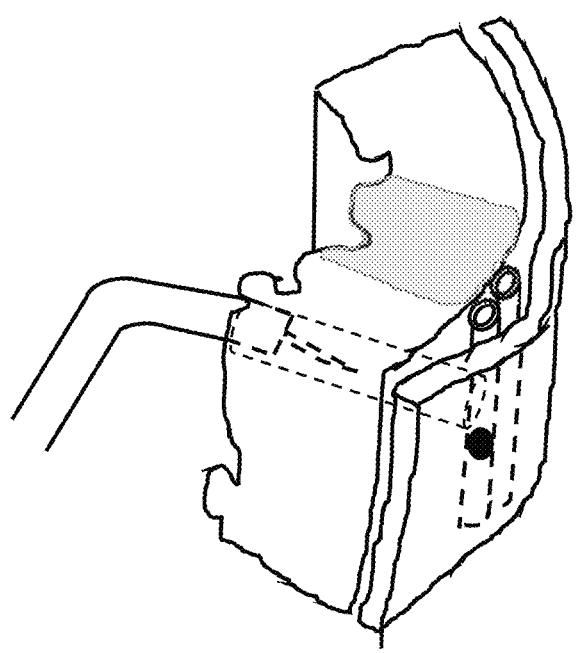
Figure 38D:
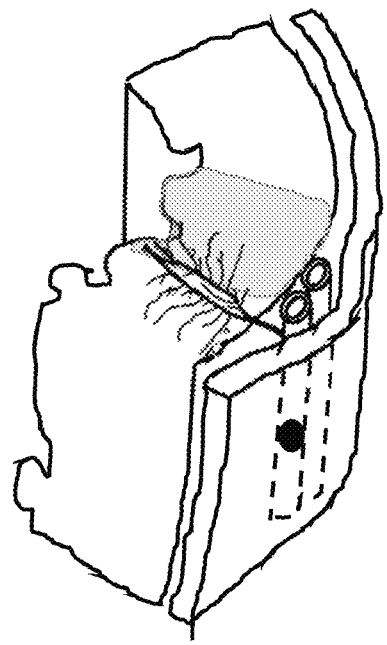

After the channel has been created, the physician may decide to gradually release the angiogenic-based therapy by slowly withdrawing and/or rotating the DDS catheter (see FIG. 38C). The slow withdrawal may allow the angiogenic-based therapy to diffuse through the proper cardiac tissue layers (and/or for the therapy to be deposited within the created channel). Alternatively, the physician may decide to administer the angiogenic-based therapy during the channel creation. Furthermore, it may be desirable that the angiogenic-based therapy includes radiopacity, such as discussed herein, for enhancing visualization and ensuring proper depth and trajectory. Depending on the treatment plan, the physician may reposition the DDS within the heart to create multiple channels and/or ensure appropriate coverage of the targeted region of interest.

Figure 39A:
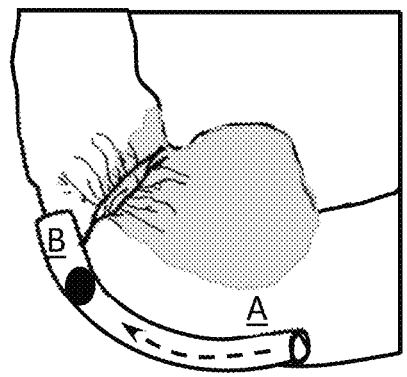
FIGS. 39A through 39F depict a magnified view of targeted or localized administration of an exemplary angiogenic-based therapy.

FIGS. 39A through 39F illustrate various embodiments for angiogenic-based therapy treatments. FIG. 39A illustrates a patient with an atherosclerotic lesion (black circle) that caused an endocardial infarct (grey area). The atherosclerotic lesion may partially occlude or fully occlude the coronary vessel, impairing the coronary vessel from normal autoregulation operation. The coronary vessel may have normal coronary perfusion and contractility in a specific region (A) and may have difficulty sending blood flow, vasodilating signals and/or chemicals to the affected region (B). As a result, the microvasculature in the affected region (B) may not dilate to compensate for increase blood perfusion (increased oxygen demand). The imbalance of supply and demand can cause ischemia and develop into an infarct.

Figure 39B:
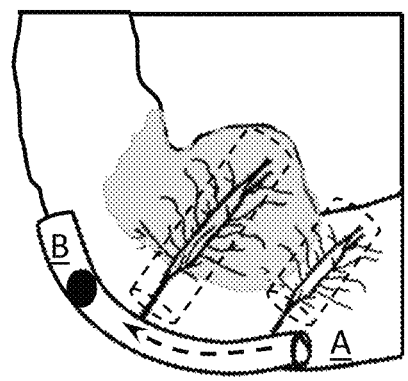
Figure 39C:
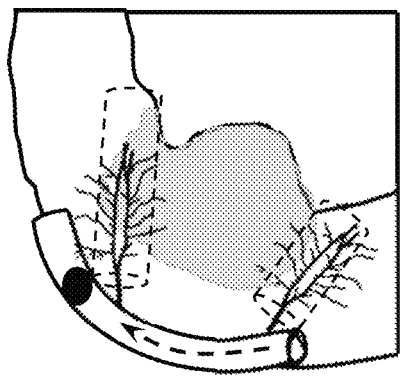
Figure 39D:
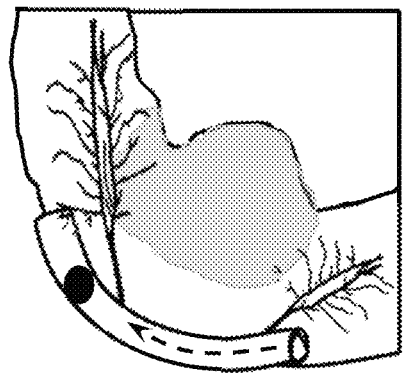

FIG. 39B illustrates one embodiment of a revascularization treatment that bypasses an atherosclerotic lesion to create a new collateral microvascular network. The physician may create one or more channels in the normal coronary perfusion and contractility region (A) bypassing the affected region (B). The angiogenic-based therapy can be administered within the infarct or adjacent to the infarct. As a result, placement of the new collateral microvascular network will desirably respond to the normal coronary artery autoregulation response to properly distribute blood flow, the vasodilating signals and/or chemicals to the one or more new microvascular networks. Optionally, if an atherosclerotic plaque is present, the physician may choose to characterize the plaque for potential stabilization treatments and/or remove the occlusion using standard procedures known in the art. FIGS. 39C and 39D illustrates alternate embodiments of revascularization treatments. The physician may decide to treat the perimeter or border of the infarct, treat adjacent cardiac tissue that may be non-infarcted, treat infarcted tissue, and/or any combination thereof.

Figure 39E:
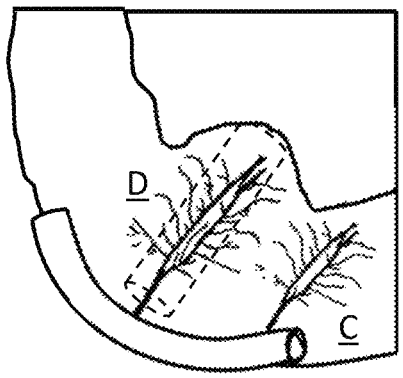
Figure 39F:
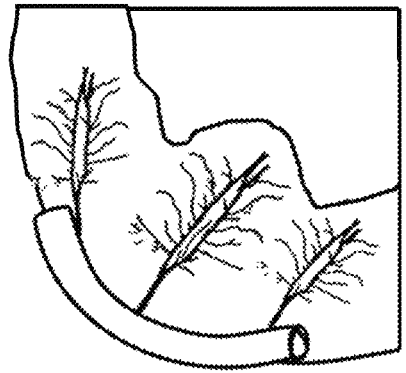

FIGS. 39E and 39F illustrate various embodiments of revascularization treatments that bypass the affected microvasculature network (C) to create a new collateral microvascular network (D). FIG. 39E illustrates a patient with microvascular disease (or small vessel disease) and no atherosclerotic lesions. As previously discussed herein, patients with MVD contain various particularities within the microvasculature that can affect the resistance of the overall coronary perfusion or blood flow (C). Without a coronary atherosclerotic lesion, the coronary artery exhibits proper autoregulation response, and delivers the relevant vasodilating signals and/or chemicals to the microvasculature. However, the particularities observed in the microvasculature can prevent the affected microvasculature (C) from responding to the vasodilation. The imbalance of supply versus demand can cause ischemia and potential develop into an infarct.

As a result, the physician may bypass the affected microvasculature (C) to create one or more channels. The physician can administer the angiogenic-based therapy to create a new collateral microvascular network (D). The new microvascular network will desirably be free of particularities and thus, able to respond adequately to the demand of increased perfusion and oxygen. FIG. 39F illustrates additional channels and new collateral microvascular networks.

Example 2—"At-Risk" Treatments

In other embodiment, the physician may employ invasive techniques for assessing endothelial function and administering the angiogenic-based therapy. Such invasive techniques may include intracoronary and intrabrachial infusion of vasoactive agents. Intracoronary infusion may allow for direct quantification of endothelial function in the coronary arteries and CMVD, since it allows both the evaluation of dose-response relations of endothelial agonists and antagonists, as well as assessing the basal endothelial function by the infusion of nitric oxide synthase (NOS) inhibitors. Intracoronary infusion may be performed under angiographic guidance and measurements. The physician may infuse with at least one vasoactive substance, including acetylcholine, bradykinin, serotonin, or substance P to vasoconstrict the underlying smooth muscle cells. A Doppler tipped guidewire may be placed in the proximal segment of a coronary artery or respective location near or adjacent to the coronary microvasculature using a 6 French Judkins Doppler infusion catheter. The Doppler flow velocity should be continuously recorded. Acetylcholine can be infused in the coronary artery through the Judkins catheter at increasing rates (for example, 1, 3, 10, and 30 mg/min) while normal saline is co-infused with acetylcholine as a vehicle, and the total infusion rate is kept constant by the use of an arterial infusion pump. Each dose is infused for 1-2 minutes. Coronary artery diameter, volumetric coronary blood flow and/or Coronary blood flow velocity can be measured by an on-line spectral analyzer and recorded on tape. Endothelial function is finally evaluated by analyzing the dose-response curves. Coronary arteries with normal endothelium dilate in a dose dependent way, while in the presence of endothelial dysfunction, acetylcholine may lead to a decreased vasodilatory response or even vasoconstriction of the coronary artery. Co-infusion of NG-monomethyl-L-arginine (L-NMMA), an NOS inhibitor, blocks the vasodilatory effect of acetylcholine. The vasodilatory effect of acetylcholine or other vasodilators is usually compared with the response to glyceryl trinitrate, an exogenous source of NO leading to endothelium independent dilation of the vessel.

The coronary artery diameter, volumetric coronary blood flow and/or coronary blood flow velocity of "at-risk" patients may be compared to healthy patients (patients with normal coronary angiograms and no major and/or minor risk factors). Such healthy patient measurements may be accessed from a database library and/or the physician may compare to the specific patient's previous healthy measurements. For example, acetylcholine infusion into the coronary arteries should produce a significant increase in coronary blood flow in healthy patients, and a lower magnitude increase in "at-risk" patients. Such lower magnitude of blood flow may suggest that the vasodilator paradoxically constricts the coronary artery indicating endothelial dysfunction.

Once the physician identifies a lower magnitude of coronary blood flow (i.e., hypoperfusion), the physician may desirably administer angiogenic-based therapy to the region of interest as discussed herein.

Alternatively, the physician may employ another invasive technique known as intrabrachial infusion of vasoactive agents. The technique of intracoronary infusion of vasoactive agents can also be applied in the brachial artery, which is easily accessible and its cannulation has fewer potential dangers and complications. However, instead of measuring coronary diameter, coronary blood flow, and/or coronary volumetric blood flow, the physician may measure blood pressure, heart rate, and/or forearm blood flow (FBF) via gauge-strain plethysmography.

In another embodiment, the physician may employ non-invasive techniques to assess endothelial function in patients. These non-invasive techniques include high resolution ultrasound (HRUS) under dependent flow mediated vasodilation and/or gauge-strain plethysmography under reactive hyperaemia. These techniques are easily applied in humans and other mammals, and can be used as the main diagnostic test for identification of early onset atherosclerosis and/or used as screening tests, where the physician recommends subsequent invasive tests for confirming early onset atherosclerosis. They are usually applied to the arm or forearm and evaluate endothelial function in the brachial artery or the resistance vessels of the upper arm.

HRUS allows the physician to measure brachial baseline blood flow and brachial blood flow after physical ischemia induced by an ischemia cuff. Peripheral arteries, especially the brachial artery, respond to physical and chemical stimuli by adjusting vascular tone and regulating blood flow. Increased blood flow in peripheral arteries leads to increased shear stress stimuli, increased NO production, and vasodilation. The vasodilatory response of the brachial artery to increased shear stress is called flow mediated dilation (FMD), and reflects the ability of vascular endothelium to produce NO.

In one example, the brachial artery is imaged above the antecubital fossa in the longitudinal plane, by using a linear array transducer (with frequency 7-12 MHz) attached to a high quality mainframe ultrasound system. The diameter of the brachial artery is initially determined at rest, and blood flow is estimated by time averaging the pulsed Doppler velocity signal obtained from a mid-artery sample volume. The diameter of the brachial artery is determined manually with electronic calipers or automatically using edge detection software. To decrease the variability of the measurements, the brachial artery diameter could be determined by the average derived from multiple diameter measurements along a segment of the vessel. After baseline brachial artery diameter determination, ischemia can be induced by inflating a cuff placed at the distal forearm, at a pressure 50 mm Hg greater than the systolic blood pressure. Alternatively, the ischemia cuff can be placed at the upper arm instead of the forearm, resulting in a greater hyperaemic flow and higher brachial artery vasodilation after its release.

The release of the ischemia cuff after five minutes leads to an increase in forearm blood blow (FBF), resulting in a vasodilatory effect on the brachial artery. The maximum blood flow velocity is detected by analyzing mid artery pulsed Doppler signal immediately after or up to 15 seconds after cuff release, while the maximum diameter of the brachial artery is determined approximately 60 seconds after release or 45-60 seconds after the peak hyperaemic flow. Additional information may be offered by the evaluation of the "area under the curve" of the diameter versus time from ischemic cuff release. It is important to measure the diameter of the brachial artery at the same period of the cardiac cycle, to avoid any effect of arterial compliance on the measurements. Therefore, simultaneous ECG recordings are desired to achieve the most reliable results.

FMD may be calculated as the percentage change of the brachial artery diameter from rest to the diameter 60 seconds after ischemia cuff release. All the determinations can be carried out on tape by two independent observers, since the brachial artery is continuously monitored from 30 seconds before to 120 seconds after ischemia cuff release. The comparison of FMD with endothelium dependent dilation in the brachial artery, produced after glyceryl trinitrate administration, often helps to elucidate changes in smooth muscle function or arterial compliance that may affect the observed changes in FMD.

Alternatively, the physician may use another use non-invasive evaluation of endothelial function in the brachial artery through application of gauge-strain plethysmography. This technique is the evaluation of the changes in FBF during reactive hyperaemia. It is the percentage change of flow from baseline to the maximum flow during reactive hyperaemia following a five minute ischemia of the distal forearm. Furthermore, the evaluation of the maximum hyperaemic flow and the overall time-flow curve during reactive hyperaemia may also offer significant information in evaluating endothelial function.

Once the physician calculates the percentage change in FBF and the percentage change of the diameter of the brachial artery, the physician may optionally recommend that the patient undergo invasive endothelial function testing, IMR analysis and/or LVEMM analysis. However, the physician may use the results from the non-invasive methods to place the patient in the prophylactic angiogenic-based therapy treatment group. The physician can create his preoperative plan to access the region of interest and desirably administer angiogenic-based therapy as discussed herein.

HEADINGS

The headings provided herein are merely for the reader's convenience, and should not be construed as limiting the scope of the various disclosures or sections thereunder, nor should they preclude the application of such disclosures to various other embodiments or sections described herein.

INCORPORATION BY REFERENCE

The entire disclosure of each of the publications, patent documents, and other references referred to herein is incorporated herein by reference in its entirety for all purposes to the same extent as if each individual source were individually denoted as being incorporated by reference.

EQUIVALENTS

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention. The invention may be embodied in other specific forms without departing from the spirit or essential characteristics thereof. The foregoing embodiments are therefore to be considered in all respects illustrative rather than limiting on the invention described herein. Scope of the invention is thus intended to include all changes that come within the meaning and range of equivalency of the claims provided herein.

What is claimed is:

1. A method of treating an ischemic region of cardiac tissue of a heart of a subject, the method comprising the steps of:
    obtaining non-invasive image data of the subject, the non-invasive image data including a region of cardiac tissue,
    analyzing the image data to preoperatively identify at least one ischemic region of cardiac tissue,
    preoperatively identifying a first injection site within a first area of cardiac tissue proximate to the ischemic region of cardiac tissue, wherein the first injection site is proximate the ischemic region of cardiac tissue,
    operatively administering a therapeutically effective amount of a first composition comprising at least one angiogenic factor to the first injection site, wherein the angiogenic factor is fibroblast growth factor-1 (FGF-1) and is provided in a dose of between about 2 and 20 micrograms per kilogram that reaches a $C_{max}$ in less than 1 hour and that at least one of: prevents relocation of myofibrils, glycogen loss, or mitochondrial swelling, and wherein the administration of the angiogenic factor induces growth of cardiac blood vessels and cardiac angiogenesis within the first area of cardiac tissue proximate to the ischemic region of cardiac tissue.

2. The method of claim 1, further comprising the step of preoperatively identifying a second injection site within a second area of cardiac tissue, wherein the first injection site is adjacent to the ischemic region of cardiac tissue and the second injection site is outside of the ischemic region of cardiac tissue.

3. The method of claim 1, wherein the step of operatively administering the therapeutically effective amount of the first composition comprises injecting the therapeutically effective amount of the first composition into the first area of cardiac tissue from a location outside of the heart.

4. A method of treating a patient having ischemic cardiac tissue resulting from diminished microvascular blood flow, comprising:
    obtaining non-invasive image data of cardiac tissue of the patient,
    analyzing the image data to identify the ischemic cardiac tissue;
    obtaining a composition comprising a carrier combined with an angiogenic growth factor, wherein the angiogenic factor is fibroblast growth factor-1 (FGF-1) and is provided in a dose of between about 2 and 20 micrograms per kilogram that reaches a $C_{max}$ in less than 1 hour and that at least one of: prevents relocation of myofibrils, glycogen loss, or mitochondrial swelling and wherein the carrier is selected from at least one of hyaluronic acid, collagen gel, alginate gel, gelatin-resorcin-formalin adhesive, mussel-based adhesive, dihydroxyphenylalanine-based adhesive, chitosan, transglutaminase, poly(amino acid)-based adhesive, cellulose-based adhesive, polysaccharide-based adhesive, synthetic acrylate-based adhesives, platelet rich plasma (PRP) gel, platelet poor plasma (PPP) gel, and clot, wherein the carrier and FGF-1 are in an aqueous solution,
    applying the composition to the anatomical structure of the patient into the ischemic cardiac tissue, thereby inducing cardiac angiogenesis proximate to the composition.

5. The method of claim 4, wherein at least a portion of the composition is applied outside of the ischemic cardiac tissue.

6. The method of claim 4, wherein at least a first portion of the composition is applied within the ischemic cardiac tissue and at least a second portion of the composition is applied outside of the ischemic cardiac tissue.

7. The method of claim 4, further comprising accessing the anatomical structure via a percutaneous path through an inner surface of a heart of the patient.

8. The method of claim 4, further comprising accessing the anatomical structure via an outer surface of a heart of the patient.

9. The method of claim 4, wherein the carrier solution is capable of adhering to an anatomical structure of the patient.

10. The method of claim 4, wherein the composition is contained within a biodegradable membrane.

11. A method of treating a region of cardiac tissue in a subject, the method comprising the steps of:
    obtaining preoperative non-invasive image data of the subject, the preoperative noninvasive image data including a region of cardiac tissue, analyzing the preoperative non-invasive image data to preoperatively identify at least one at-risk region of cardiac tissue, preoperatively identifying at least one abnormality within a blood vessel supply to the at-risk region of cardiac tissue, operatively administering a therapeutically effective amount of a first composition comprising fibroblast growth factor-1 (FGF-1)) and is provided in a dose of between about 2 and 20 micrograms per kilogram that reaches a $C_{max}$ in less than 1 hour and that at least one of: prevents relocation of myofibrils, glycogen loss, or mitochondrial swelling into the at least one abnormality, wherein the FGF-1 induces growth of supplemental cardiac blood vessels proximate to the abnormality.

12. The method of claim 11, wherein the step of administration of the angiogenic factor induces growth of blood vessels proximate to the abnormality, wherein at least a portion of the blood vessel supply to the at-risk region of cardiac tissue is redirected through the supplemental blood vessels.

13. The method of claim 11, wherein the abnormality is located within the at-risk region of cardiac tissue.

14. The method of claim 11, wherein the abnormality is located within the region of cardiac tissue.

15. The method of claim 11, further comprising the steps of obtaining postoperative non-invasive image data of the subject, the post-operative noninvasive, image data including the at-risk region of cardiac tissue, analyzing the post-operative non-invasive image data to identify any improvement in the blood vessel supply to the at-risk region of cardiac tissue.

* * * * *